United States Patent
Takaki et al.

[11] Patent Number: 6,057,412
[45] Date of Patent: May 2, 2000

[54] AMPHIPATHIC COMPOUND HAVING SUCCINIC ACID SKELETON

[75] Inventors: Toshihiko Takaki; Masaru Tanabe, both of Yokohama; Hiroshi Itoh, Kamakura; Masayuki Yanagi; Shoko Oyanagi, both of Yokohama; Hiroyoshi Watanabe, Osakasayama, all of Japan

[73] Assignee: Mitsui Chemicals, Inc., Japan

[21] Appl. No.: 09/118,273

[22] Filed: Jul. 17, 1998

Related U.S. Application Data

[62] Division of application No. 08/658,254, Jun. 4, 1996, Pat. No. 5,872,287.

[30] Foreign Application Priority Data

| Jun. 9, 1995 | [JP] | Japan | 7-143038 |
|---|---|---|---|
| Aug. 4, 1995 | [JP] | Japan | 7-199590 |
| Aug. 4, 1995 | [JP] | Japan | 7-199591 |
| Aug. 9, 1995 | [JP] | Japan | 7-203093 |
| Aug. 15, 1995 | [JP] | Japan | 7-207958 |
| Aug. 31, 1995 | [JP] | Japan | 7-223093 |
| Dec. 7, 1995 | [JP] | Japan | 7-318946 |

[51] Int. Cl.$^7$ ................................. C08F 18/14
[52] U.S. Cl. ............. 526/321; 526/240; 526/304; 526/306; 526/310; 526/312; 526/320; 526/323; 526/323.1; 526/328
[58] Field of Search ..................... 526/304, 310, 526/312, 328, 240, 321, 323, 323.1, 320, 306

[56] References Cited

U.S. PATENT DOCUMENTS

| 2,749,361 | 6/1956 | Yale . |
| 3,956,225 | 5/1976 | Murato et al. . |
| 3,960,935 | 6/1976 | Samour . |
| 4,611,087 | 9/1986 | Yamashita et al. . |

FOREIGN PATENT DOCUMENTS

| 0402476 | 12/1990 | European Pat. Off. . |
| 4325338 | 2/1995 | Germany . |
| 63-235595 | 9/1988 | Japan . |
| 5-125681 | 5/1993 | Japan . |
| WO94/00508 | 1/1994 | WIPO . |

*Primary Examiner*—Fred Zitomer
*Attorney, Agent, or Firm*—Burns, Doane, Swecker & Mathis, L.L.P.

[57] ABSTRACT

An amphipathic compound represented by any of the following Formulas:

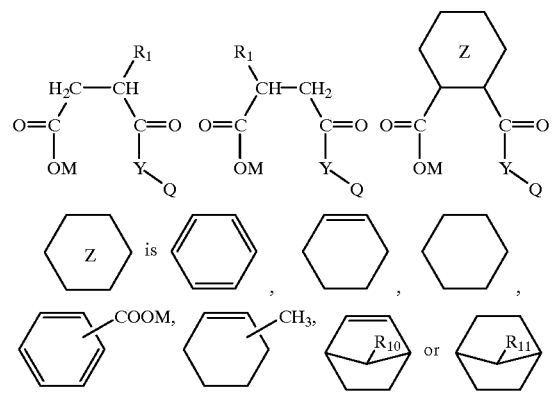

($R_1$ is a linear or branched, saturated hydrocarbon group having 6 to 48 carbon atoms, or a linear or branched, unsaturated hydrocarbon group containing 1 to 12 unsaturated double bond and having 6 to 48 carbon atoms; Y is NH, N—($CH_2$—CH=$CH_2$), or O; Q is —$CH_2$—C($R_2$)=$CH_2$ or —$R_4$—O—CO—C($R_2$)=$CH_2$; and M is alkali metal, an ammonium group, or —($CH_2CH_2O)_m$H), a copolymer of the amphipatic compound with a copolymerizable ethylenically unsaturated compound and, a paper making additive containing a water soluble or dispersible high molecular compound as an active ingredient and processes for producing these high molecular compounds.

10 Claims, 10 Drawing Sheets

AMPHIPATHIC COMPOUND HAVING SUCCINIC ACID SKELETON

This application is a divisional, of application Ser. No. 08/658,254, filed Jun. 4, 1996, U.S. Pat. No. 5,872,287.

BACKGROUND OF THE INVENTION (1) Field of the Invention

The present invention relates to an amphipathic compound, a high molecular compound using the same, and a process for producing the same.

Since the amphipathic compound of the present invention has at least one double bond in a molecule and is capable of polymerizing with various ethylenically unsaturated compounds, it is a useful compound as a raw material for a synthetic resin. Further, the amphipathic compound of the present invention is a compound which is classified as a reactive surfactant, and a high molecular compound obtained by copolymerizing the amphipathic compound of the present invention with an ethylenically unsaturated compound is used for plasticizers, heat resistant resins, lubricants, antistatic agents, paints, adhesives, dispersants, and additives for cement. A copolymer of the amphipathic compound of the present invention with a hydrophilic ethylenically unsaturated compound is soluble or dispersible in water and useful as a high molecular type surfactant. In particular, the copolymer with (meth)acrylamide has a high utility value as a novel paper making additive, which can improve sizing performance and paper reinforcing performance at the same time.

(2) Description of the Related Art Japanese Patent Laid-open SHO 63-235595 and HEI 5-125681 disclose alkenyl succinic acid semi-ester and a reaction product of alkyl or alkenyl succinic acid with an alkylene oxide adduct of polyhydric alcohol. However, the amphipathic compound of the present invention is a novel compound which has not so far been reported. Further, the copolymer of the amphipathic compound of the present invention with an ethylenically unsaturated compound is also a novel compound which has not so far been reported.

SUMMARY OF THE INVENTION

An object of the present invention is to provide (1) a novel amphipathic compound having a succinic acid derivative skeleton with a polymerizable unsaturated bond, (2) a novel amphipathic compound having phthalic acid and its derivative skeletons, (3) a high molecular compound obtained by copolymerizing the amphipathic compound having a succinic acid derivative skeleton with a copolymerizable ethylenically unsaturated compound, (4) a high molecular compound obtained by copolymerizing the amphipathic compound having phthalic acid and its derivative skeletons with a copolymerizable ethylenically unsaturated compound, (5) a water soluble or dispersible high molecular compound obtained by copolymerizing the amphipathic compound having a succinic acid derivative skeleton with a hydrophilic ethylenically unsaturated compound, (6) a water soluble or dispersible high molecular compound obtained by copolymerizing the amphipathic compound having phthalic acid and its derivative skeletons with the copolymerizable, hydrophilic ethylenically unsaturated compound, and a paper making additive containing the water soluble or dispersible high molecular compounds of (5) and (6) as an active ingredient. Among them, particularly the copolymer with (meth)acrylamide is abbreviated as a PAM group sizing agent.

Further, an another object of the present invention is to provide (7) an emulsion having an ability to form a polymer film having excellent heat resistance and water resistance, in which the amphipathic compound of the present invention is used as an emulsifier, (8) a process for producing an amphipathic high molecular compound having a high molecular weight and a low viscosity by copolymerizing the amphipathic compound of the present invention with a hydrophilic ethylenically unsaturated compound in the presence of a colloidizing agent, and (9) a process for producing an emulsion having a heteromorphic structure, obtained by polymerizing a hydrophobic ethylenically unsaturated compound in the presence of the amphipathic compound of the present invention.

That is, the present invention relates to:

1) an amphipathic compound having a succinic acid skeleton represented by any of the following Formulas (1) to (4):

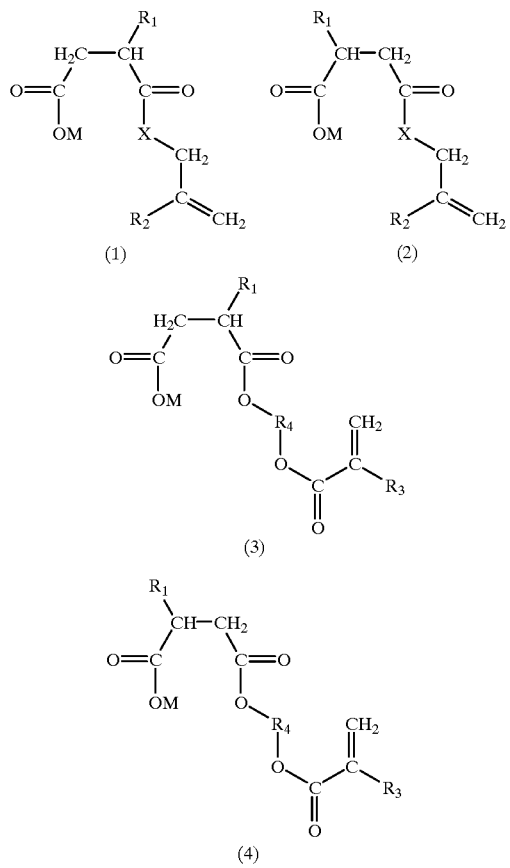

wherein $R_1$ is a linear or branched saturated hydrocarbon group having 6 to 48 carbon atoms, or a linear or branched unsaturated hydrocarbon group containing 1 to 12 unsaturated double bonds and having 6 to 48 carbon atoms; $R_2$ and $R_3$ are independently a hydrogen atom or a methyl group; $R_4$ is a linear or branched saturated hydrocarbon group having 2 to 6 carbon atoms; M is a hydrogen atom, an alkali metal, or an ammonium group; and X is NH or N—($CH_2$—CH=$CH_2$);

2) an amphipathic compound having a succinic acid skeleton represented by any of the following Formulas (5) to (8):

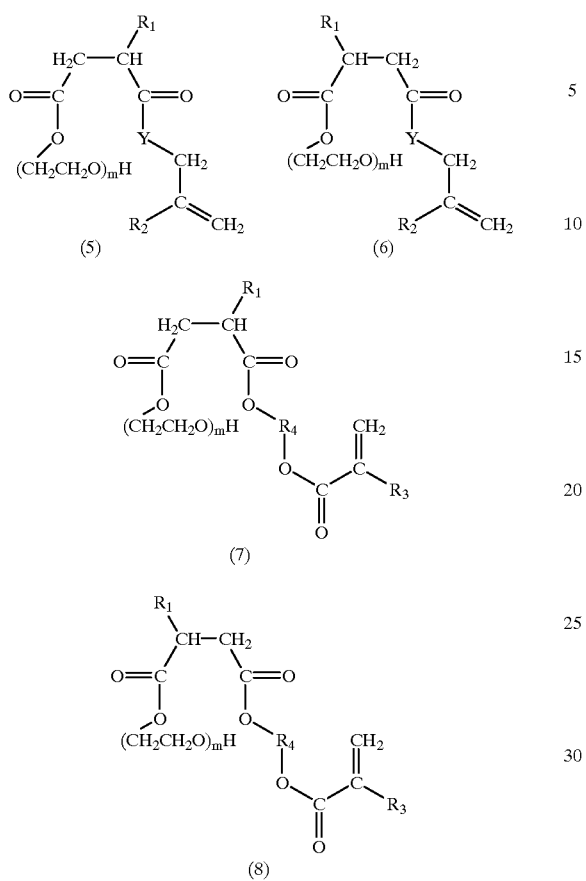

wherein $R_1$ is a linear or branched saturated hydrocarbon group having 6 to 48 carbon atoms, or a linear or branched unsaturated hydrocarbon group containing 1 to 12 unsaturated double bonds and having 6 to 48 carbon atoms; $R_2$ and $R_3$ are independently a hydrogen atom or a methyl group; $R_4$ is a linear or branched saturated hydrocarbon group having 2 to 6 carbon atoms; Y is NH, N—(CH$_2$—CH=CH$_2$), or O; and m is an integer of 1 to 100;

3) an amphipathic compound in which $R_1$ in Formulas (1) to (4) of 1) is represented by any of the following Formulas (9) to (13):

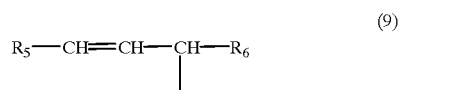

wherein $R_5$ and $R_6$ are independently a hydrogen atom, or a linear alkyl group or alkenyl group of $C_1$ to $C_{23}$, provided that a carbon number of $(R_5+R_6)$ falls in a range of 3 to 45;

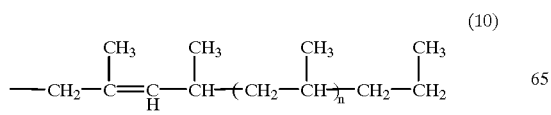

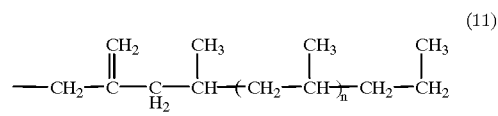

wherein n is an integer of 0 of 6;

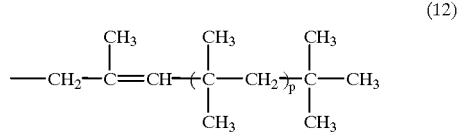

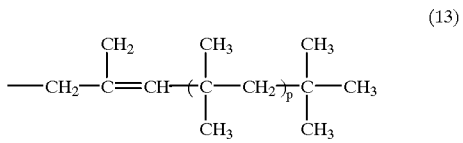

wherein p is an integer of 0 to 6;

4) an amphipathic compound in which $R_1$ in Formulas (5) to (8) of 2) is represented by any of the following Formulas (9) to (13):

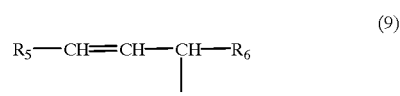

wherein $R_5$ and $R_6$ are independently a hydrogen atom, or a linear alkyl group or alkenyl group of $C_1$ to $C_{23}$, provided that a carbon number of $(R_5+R_6)$ falls in a range of 3 to 45;

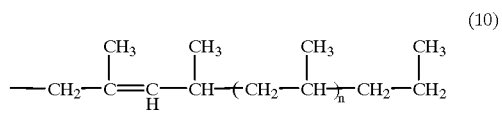

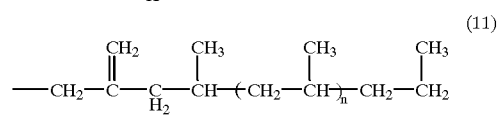

wherein n is an integer of 0 of 6;

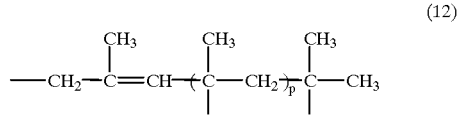

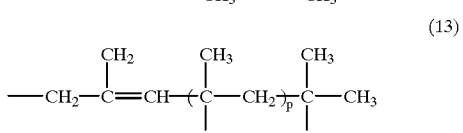

wherein p is an integer of 0 to 6;

5) an amphipathic compound having any of phthalic acid or tetrahydrophthalic acid, hexahydrophthalic acid, norbornenedicarboxylic acid, and norbornanedicarboxylic acid structures represented by following Formulas (14) to (17):

(14)

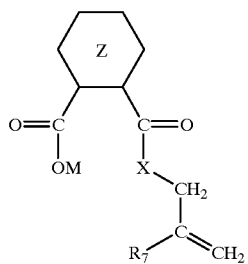

(15)

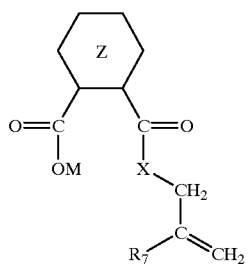

(16)

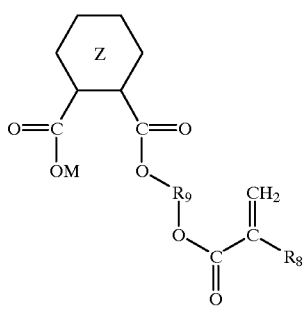

(17)

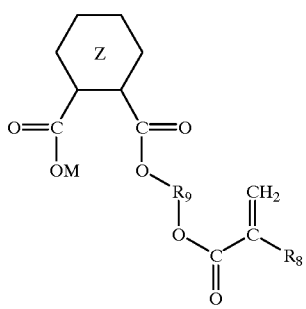

Z is wherein $R_7$ and $R_8$ are independently a hydrogen atom or a methyl group; $R_9$ is a linear or branched saturated hydrocarbon group having 2 to 6 carbon atoms; $R_{10}$ and $R_{11}$ are independently a hydrogen atom or a methyl group; M is a hydrogen atom, an alkali metal, or an ammonium group; and X is NH or N—($CH_2$—CH=$CH_2$);

6) a high molecular compound obtained by copolymerizing 0.1 to 90.0 weight % of an amphipathic compound having a succinic acid skeleton represented by any of Formulas (18) to (21) or a mixture thereof with 10.0 to 99.9 weight % of a copolymerizable ethylenically unsaturated compound:

(18)

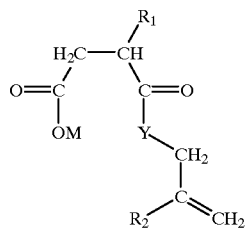

(19)

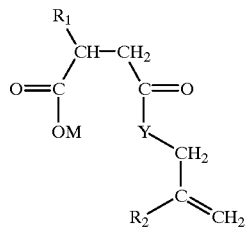

(20)

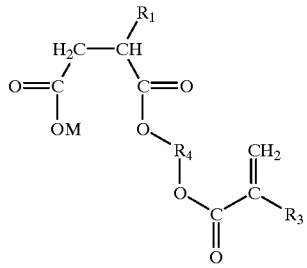

(21)

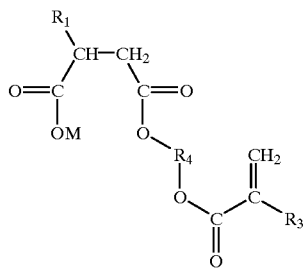

wherein $R_1$ is a linear or branched saturated hydrocarbon group having 6 to 48 carbon atoms, or a linear or branched unsaturated hydrocarbon group containing 1 to 12 unsaturated double bonds and having 6 to 48 carbon atoms; $R_2$ and $R_3$ are independently a hydrogen atom or a methyl group; $R_4$ is a linear or branched saturated hydrocarbon group having 2 to 6 carbon atoms; M is a hydrogen atom, an alkali metal, or an ammonium group; and Y is NH, N—($CH_2$—CH=$CH_2$), or O;

7) a water soluble or dispersible amphipathic high molecular compound obtained by copolymerizing 0.1 to 90.0 weight % of the compound represented by any of Formulas (18) to (21) as described in 6) or a mixture thereof with 10.0 to 99.9 weight % of a hydrophilic ethylenically unsaturated compound;

8) a paper making additive containing the water soluble or dispersible amphipathic high molecular compound as described in 7) as an active ingredient;

9) a high molecular compound obtained by copolymerizing 0.1 to 90.0 weight % of the compound represented by any of Formulas (5) to (8) as described in 2) or a mixture thereof with 10.0 to 99.9 weight % of a copolymerizable ethylenically unsaturated compound;

10) a water soluble or dispersible amphipathic high molecular compound obtained by copolymerizing 0.1 to 90.0 weight % of the compound represented by any of Formulas (5) to (8) as described in 2) or a mixture thereof with 10.0 to 99.9 weight % of a hydrophilic ethylenically unsaturated compound;

11) a paper making additive containing the water soluble or dispersible amphipathic high molecular compound as described in 10) as an active ingredient;

12) a high molecular compound having phthalic acid or tetrahydrophthalic acid, hexahydrophthalic acid, norbornenedicarboxylic acid, and norbornanedicarboxylic acid structures on side chains which is obtained by copolymerizing 0.1 to 90.0 weight % of a compound represented by any of Formulas (22) to (25) or a mixture thereof with 10.0 to 99.9 weight % of a copolymerizable ethylenically unsaturated compound:

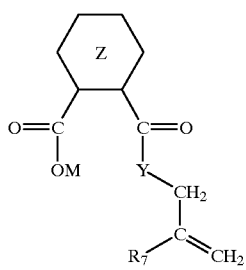

(22)

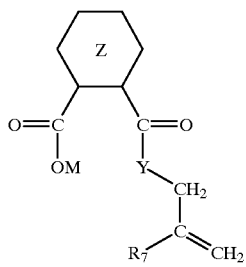

(23)

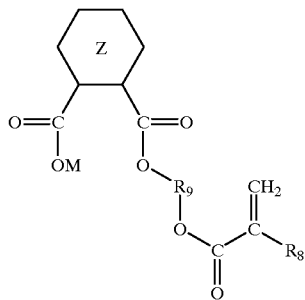

(24)

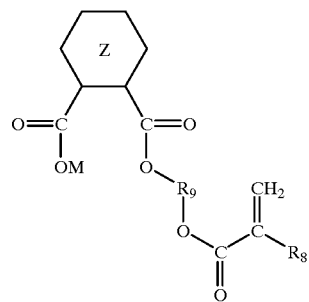

(25)

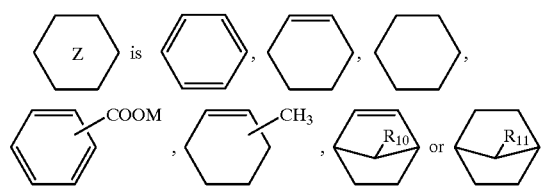

wherein $R_7$ and $R_8$ are independently a hydrogen atom or a methyl group; $R_9$ is a linear or branched saturated hydrocarbon group having 2 to 6 carbon atoms; $R_{10}$ and $R_{11}$ are independently a hydrogen atom or a methyl group; M is a hydrogen atom, an alkali metal, or an ammonium group; and Y is NH, N—($CH_2$—CH=$CH_2$), or O;

13) a water soluble or dispersible amphipathic high molecular compound obtained by copolymerizing 0.1 to 90.0 weight % of the compound represented by Formulas (22) to (25) as described in 12) or a mixture thereof with 10.Q to 99.9 weight % of a hydrophilic ethylenically unsaturated compound;

14) a paper making additive containing the water soluble or dispersible amphipathic high molecular compound as described in 13) as an active ingredient;

15) a reactive surfactant represented by any of Formulas (5) to (8), any of Formulas (18) to (21), or any of Formulas (22) to (25):

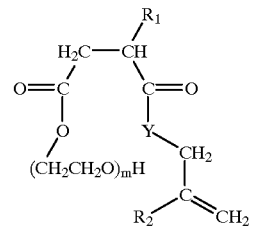

(5)

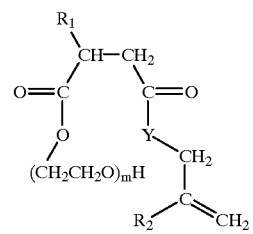

(6)

-continued

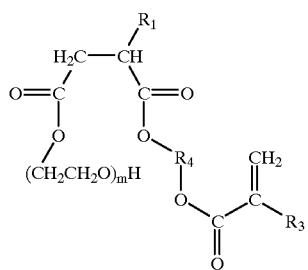
(7)

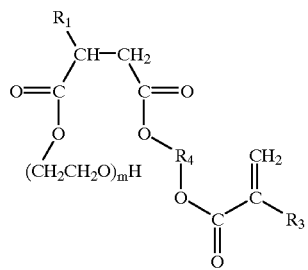
(8)

wherein $R_1$ is a linear or branched saturated hydrocarbon group having 6 to 48 carbon atoms, or a linear or branched unsaturated hydrocarbon group containing 1 to 12 unsaturated double bonds and having 6 to 48 carbon atoms; $R_2$ and $R_3$ are independently a hydrogen atom or a methyl group; $R_4$ is a linear or branched saturated hydrocarbon group having 2 to 6 carbon atoms; Y is NH, N—($CH_2$—CH=$CH_2$), or O; and m is an integer of 1 to 100;

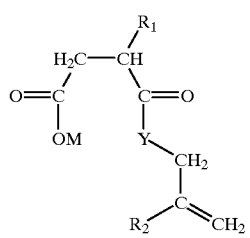
(18)

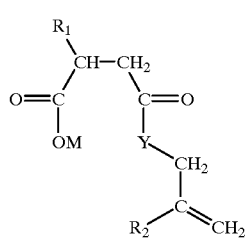
(19)

-continued

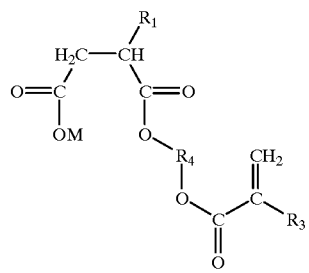
(20)

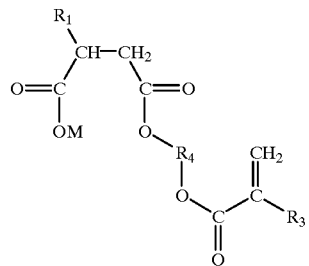
(21)

wherein $R_1$ is a linear or branched saturated hydrocarbon group having 6 to 48 carbon atoms, or a linear or branched unsaturated hydrocarbon group containing 1 to 12 unsaturated double bonds and having 6 to 48 carbon atoms; $R_2$ and $R_3$ are independently a hydrogen atom or a methyl group; $R_4$ is a linear or branched saturated hydrocarbon group having 2 to 6 carbon atoms; M is a hydrogen atom, an alkali metal, or an ammonium group; and Y is NH, N—($CH_2$—CH=$CH_2$), or O;

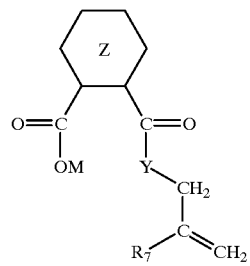
(22)

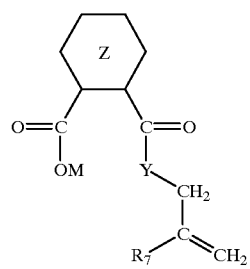
(23)

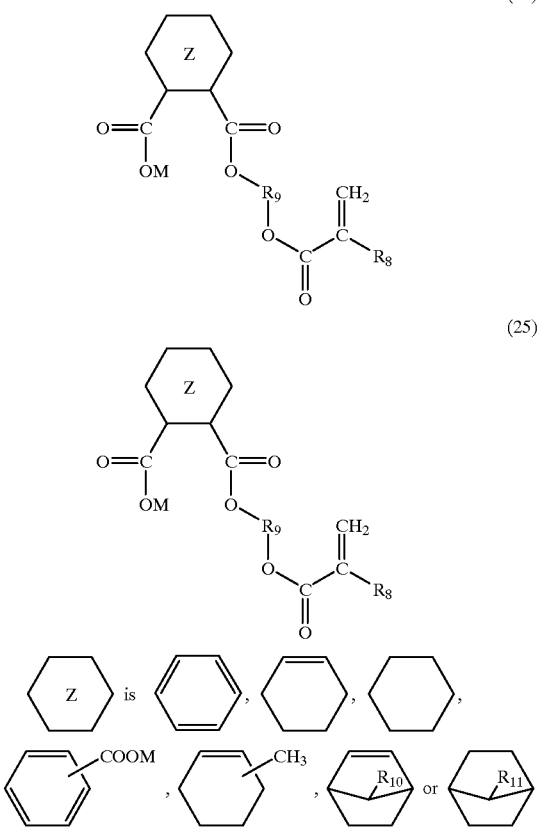

wherein $R_7$ and $R_8$ are independently a hydrogen atom or a methyl group; $R_9$ is a linear or branched saturated hydrocarbon group having 2 to 6 carbon atoms; $R_{10}$ and $R_{11}$ are independently a hydrogen atom or a methyl group; M is a hydrogen atom, an alkali metal, or an ammonium group; and Y is NH, N—($CH_2$—CH=$CH_2$) or O;

16) a water-dispersing type resin composition obtained by emulsion-polymerizing 0.1 to 20 weight % of the reactive surfactant as described in 15) with 80 to 99.9 weight % of an ethylenically unsaturated compound;

17) a high molecular surfactant obtained by copolymerizing 0.1 to 50 weight % of the reactive surfactant as described in 15) with 50 to 99.9 weight % of a hydrophilic ethylenically unsaturated compound;

18) a water-dispersing type resin composition obtained by emulsion-polymerizing an ethylenically unsaturated compound in the presence of the high molecular surfactant as described in 17);

19) a process for producing an amphipathic high molecular compound, characterized in that the reactive surfactant as described in 15) is copolymerized with a hydrophilic, nonionic unsaturated compound in an aqueous medium in the presence of a colloidizing agent;

20) a process for producing an amphipathic high molecular compound as described in 19), wherein the reactive surfactant of 0.1 to 90 weight % as described in 15) is copolymerized with the hydrophilic, nonionic ethylenically unsaturated compound of 10 to 99.9 weight % in the aqueous medium in the presence of the colloidizing agent of 0.1 to 10 moles per mole of the reactive surfactant;

21) a process for producing an amphipathic high molecular compound as described in 19) or 20), wherein the colloidizing agent comprises a combination of at least one selected from inorganic acid, organic acid, inorganic base, and organic base;

22) a process for producing an amphipathic high molecular compound as described in 19), wherein the reactive surf actant has at least one carboxyl group in the molecule;

23) a process for producing an amphipathic high molecular compound as described in 22), wherein the 10 to 99.9 weight % of hydrophilic, nonionic ethylenically unsaturated compound is copolymerized with 0.1 to 90 weight % of the reactive surfactant having at least one carboxyl group in the molecule in the aqueous medium in the presence of the colloidizing agent of 0.1 to 10 moles per mole of the reactive surfactant;

24) a process for producing an amphipathic high molecular compound as described in 23), wherein the colloidizing agent comprises a combination of at least one selected from inorganic acid, organic acid, inorganic base, and organic base; and 25) a water dispersible type resin composition obtained by emulsion-polymerizing an ethylenically unsaturated compound in the presence of the amphipathic high molecular compound as described in 17).

DETAILED DESCRIPTION OF THE PREFERRED EMBODIMENTS

Figure 1:
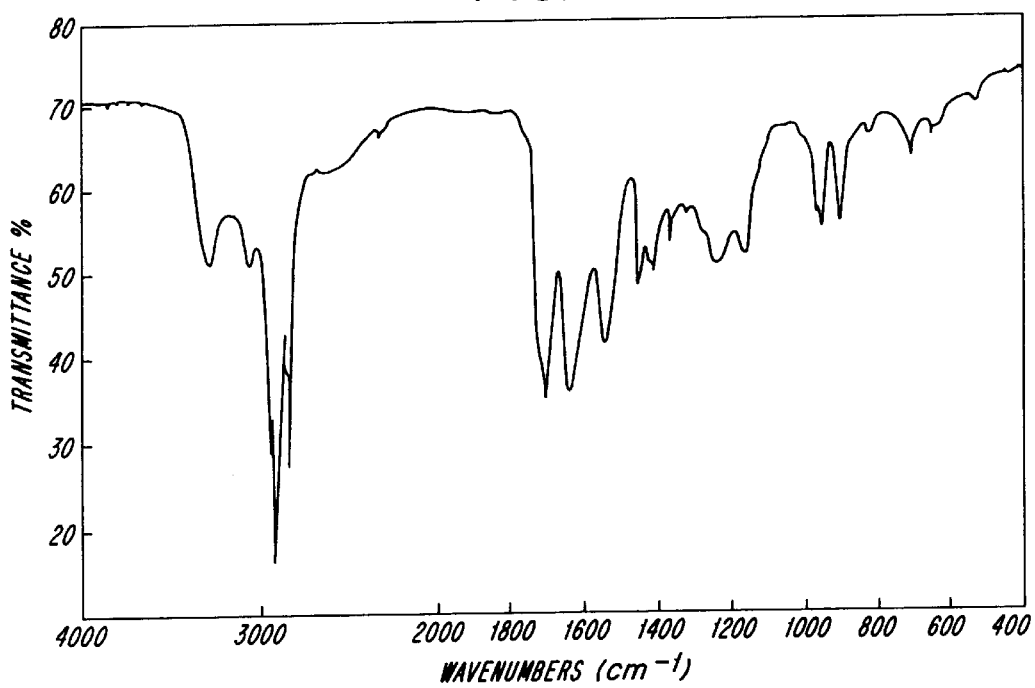
FIG. 1 is an Infrared rays (IR) absorption spectrum of the compound obtained in Example 1.

The amphipathic compound used in the present invention is classified into (1) to (4); that is, (1) an allyl compound having a succinamide structure substituted with a hydrophobic group in the skeleton; (2) an allyl or vinyl compound having a succinic acid ester structure substituted with a hydrophobic group in the skeleton; (3) an ethoxylate compound obtained by reacting an allyl or vinyl compound having a succinamide or succinic acid ester structure substituted with a hydrophobic group in the skeleton with ethylene oxide (hereinafter abbreviated as EO); and (4) an allyl compound having an amide or ester structure of phthalic acid and derivative thereof, or a mixture of at least two compounds selected from them. Among them, the compound groups excluding the allyl compound having a succinic acid ester structure described in (2) and the compound having an ester structure of a phthalic acid derivative described in (4) are the novel compounds of the present invention. The derivatives of phthalic acid as described in the present specification include tetrahydrophthalic acid derivatives, hexahydrophthalic acid, and dicarboxylic acid derivatives having norbornene and norbornane structures (endomethylenetetrahydrophthalic acid and endomethylenehexahydrophthalic acid, respectively).

(1) The allyl compound having a succinamide structure substituted with a hydrophobic group in the skeleton is produced by the reaction of a compound (hereinafter abbreviated as ASA) obtained by reacting between oligomers of olefins produced from ethylene, propylene, isobutene and butadiene and maleic anhydride, with allylamine (MA), diallylamine (DA) or methallylamine (hereinafter, the reaction products with ASA shall be abbreviated as ASA-MA and ASA-DA).

The examples of ASA are compounds obtained by known techniques, such as ① addition products of maleic anhydride to linear or branched α-olefins having 6 to 48 carbon atoms including 1-hexene, 1-octene, 1-decene, 1-dodecene, 1-tetradecene, 1-hexadecene, 1-octadecene, and 1-docosene, or a mixture thereof, ② reaction products of internal olefins obtained by isomerizing linear or branched α-olefins having 6 to 48 carbon atoms or a mixture thereof in the presence of a catalyst with maleic anhydride, and ③ reaction products of internal olefins obtained by subjecting linear or branched α-paraffins having 6 to 48 carbon atoms or a mixture thereof to dehydrogenation with maleic anhydride. They may be a mixture of the compounds having a different number of carbon atoms or having double bonds in different positions in internal olefins. Further, there may be used saturated hydrocarbons obtained by hydrogenating olefins after the reaction with maleic anhydride. Hereinafter abbreviated are a reaction product of an oligomer of ethylene with maleic anhydride as ESA, a reaction product of an oligomer of propylene with maleic anhydride as PSA, and a reaction product of an oligomer of isobutene with maleic anhydride as BSA. In general, a raw material for ESA is an oligomer produced by a process in which ethylene is subjected to oligomerization at high temperatures and high pressure with a Ziegler catalyst such as triethylaluminum, or an isomer thereof. Raw materials for PSA and BSA are oligomers obtained by polymerizing propylene or isobutene in the presence of an acid catalyst such as solid phosphoric acid and liquid phosphoric acid or a Friedel-Crafts catalyst such as aluminum chloride, or isomers thereof. The polymers are obtained in the form of olefin mixtures having distributions in the carbon numbers. Oligomers obtained by fractional distillation under atmospheric pressure or a reduced pressure are used if necessary, and those having 6 to 48 carbon atoms are suitable. If the carbon number of the oligomers is less than 6 or exceeds 48, the amphipathic character as a reactive surfactant such as ASA-MA and ASA-DA is interfered, and therefore such oligomers do not meet the objects of the present invention.

The reaction of ASA with allylamine, diallylamine and methallylamine is usually carried out by adding dropwise allylamine or diallylamine to an organic solvent solution of ASA while stirring. The organic solvents usable as a reaction solvent may be any ones as long as they dissolve both ASA and allylamines, and the examples thereof include acetone, 2-butanone, benzene, toluene, xylene, pentane, hexane, cyclohexane, DMF, DMSO, THF, diethyl ether, dioxane, dichloromethane, dichloroethane, and chloroform. Alcohol solvents such as methanol, ethanol, isopropanol, methyl cellosolve, ethyl cellosolve, 2-ethylhexanol and cyclohexanol cause partial esterification with succinic anhydride in some cases. However, since succinic anhydride is highly reactive with allylamines, and in general, ester is formed only in a small amount, alcohol solvents can be employed as well as for uses in which mixing of esters does not exert great influences on the physical properties of the resins. ASA which is liquid at room temperatures, such as ASA having a small number of carbon atoms and ASA using an internal olefin as a raw material can be reacted in a non-solvent system. In the case where a reaction solvent has to be removed, like a case where ASA-MA or ASA-DA is used in an aqueous system, the reaction is carried out preferably in the non-solvent system.

With respect to the use amount of allylamine, diallylamine or methallylamine, the equimolar amount based on a succinic anhydride group of ASA is reacted. An amount less than the equimolar causes unreacted ASA to remain, and amount exceeding the equimolar causes allylamines to form salts with a carboxyl group of ASA-DM or ASA-DA. Accordingly, both are not preferred. Since allylamines are highly volatile, a closed type reaction vessel is preferably used. When the reaction is carried out in an open system, volatilized allylamines have to be trapped in a cooler. In such case, allylamines are added in advance in such an excess amount corresponding to the amount of allylamines to be trapped that the reaction is completed. The reaction is carried out at atmospheric pressure or under pressure in a temperature range of 0 to 150° C., preferably 5 to 130° C., and more preferably 10 to 100° C. for 30 minutes to 10 hours, whereby intended ASA-MA or ASA-DA can be obtained at a high yield. The reaction is an exothermic reaction, and the reaction temperature is controlled, if necessary, by heating or cooling. The temperature does not have to be maintained constant during the reaction, and the reaction temperature may be changed for the purpose of controlling the reaction rate or adjusting the viscosity of the reaction liquid.

Both the raw material and the product of the allyl compound (1) of the present invention having a succinamide structure substituted with a hydrophobic group in the skeleton have polymerizable double bonds, and therefore it is effective to use, if necessary, a polymerization inhibitor in the production process. The polymerization inhibitor includes phenols such as hydroquinone, hydroquinone monomethyl ether, hydroxyquinoline, methoxyphenol, and p-tert-butylcatechol, nitro compounds such as nitrobenzol and nitropropane, nitroso compounds such as N-nitrosodiphenylamine and cupferron, amines such as phenothiazine, p-phenylenediamine, N-diphenyl-p-phenylenediamine, and diphenylamine, stable radicals such as diphenylpicrylhydrazyl, galvinoxyl, pheldazyl, tri-p-nitrophenylmethyl, and di-p-fluorophenylamine, nitrous acid compounds such as sodium nitrite, ethyl nitrite, and isopropyl nitrite, and in addition thereto, sulfur, copper salts, and thiourea compounds. The polymerization inhibitor is not restricted to the compounds exemplified above, and they may be used alone or in combination of two or more kinds thereof if necessary. The amount thereof is varied depending on the polymerization inhibitors to be used, and it falls usually in a range of 1 ppm to 300 weight %, preferably 50 ppm to 5 weight % based on allylamines of the raw material.

The allyl compound (1) thus produced having a succinamide structure substituted with a hydrophobic group in the skeleton can be used in the form of the reaction solution after carrying out operations such as removal of excess allylamines, but it can be separated, if necessary, by simple operations such as removal of the solvent. When the intended product having a high purity is required depending on uses, the allyl compounds which are solids at room temperatures such as those of which hydrophobic groups are α-olefins can be recrystallized in a solvent such as methanol, ethanol, isopropanol, acetone, toluene, benzene, xylene, and styrene. The allyl compounds which are liquid at room temperatures can be subjected to refining treatment with a column by conventional methods.

The allyl compound (1) of the present invention having a succiniamide structure substituted with a hydrophobic group in the skeleton can be produced as well by amidation of succinic acid substituted with a hydrophobic group which is a hydrolysis product of ASA with allylamines, but it is more preferred in terms of the reactivity to use ASA as the raw material.

The allyl or vinyl compound (2) having a succinic acid ester structure substituted with a hydrophobic group in the skeleton is produced by the reaction of ASA with unsaturated alcohols, that is, allyl alcohol (AL), methallyl alcohol, 2-hydroxyethyl methacrylate (HM), 2-hydroxyethyl acrylate (HA), 2-hydroxypropyl methacrylate, 2-hydroxypropyl acrylate, 3-hydroxypropyl methacrylate, 3-hydroxypropyl acrylate, 2-hydroxybutyl methacrylate, 2-hydroxybutyl acrylate, 3-hydroxybutyl methacrylate, 3-hydroxybutyl acrylate, 4-hydroxybutyl methacrylate, 4-hydroxybutyl acrylate, 4-hydroxypentyl methacrylate and 4-hydroxypentyl acrylate (the reaction products with ASA shall be hereinafter abbreviated as ASA-AL, ASA-HM and ASA-HA).

The reaction of ASA with unsaturated alcohols is usually carried out by adding dropwise unsaturated alcohols to an organic solvent solution of ASA while stirring. The organic solvents usable as a reaction solvent may be any ones as long as they dissolve both ASA and unsaturated alcohols, and the examples thereof include acetone, 2-butanone, benzene, toluene, xylene, pentane, hexane, cyclohexane, DMF, DMSO, THF, diethyl ether, dioxane, dichloromethane, dichloroethane, and chloroform. Alcohol solvents such as methanol, ethanol, isopropanol, methyl cellosolve, ethyl cellosolve, 2-ethylhexanol and cyclohexanol cause partial esterification with succinic anhydride in some cases and therefore are not preferred. ASA which is liquid at room temperatures, such as ASA having a few carbon atoms and ASA using an internal olefin as a raw material can be reacted in a non-solvent system. In the case where a reaction solvent has to be removed, like a case where ASA-AL, ASA-HA or ASA-HM is used in an aqueous system, the reaction is carried out preferably in the non-solvent system.

The reaction proceeds without catalysts, but the catalysts are preferably used in order to accelerate the reaction. The catalysts used in the present reaction are not specifically restricted, and the catalysts used for esterification can be used as well. To be concrete, the examples thereof include mineral acids such as sulfuric acid, hydrochloric acid and phosphoric acid; catalysts obtained by carrying them on inorganic carriers such as silica; organic acids such as p-tolenesulfonic acid, methanesulfonic acid and benezenesulfonic acid; solid acids such as acid ion exchange resin, and in addition thereto, zinc chloride, sodium acetate, and pyridine. They can be used singly or in combination of two or more kinds thereof. The amount thereof can not definitely be specified since it is varied depending on the catalysts to be used. Usually, it falls in a range of 0.001 to 300 weight %, preferably 0.01 to 30 weight % based on the weight of ASA of the raw material.

Both the raw material and the product of the allyl or vinyl compound (2) used in the present invention having a succinic acid ester structure substituted with a hydrophobic group in the skeleton have polymerizable double bonds, and therefore it is effective to use, if necessary, a polymerization inhibitor in the production process. In particular, hydroxyalkyl (meth)acrylates such as HA and HM which are vinyl compounds are highly polymerizable, and therefore polymerization inhibitors are preferably used for the reaction. The same compounds as those used in producing the allyl compound (1) having a succinamide structure substituted with a hydrophobic group in the skeleton can be used as the polymerization inhibitor. The amount thereof is varied depending on the polymerization inhibitors. Usually, it falls in a range of 1 ppm to 300 weight %, preferably 50 ppm to 5 weight % based on the weight of unsaturated alcohols of the raw materials.

The unsaturated alcohols are reacted in an equimolar amount based on a succinic acid group of ASA (that is, a hydroxyl group of 1 mole per mole of acid anhydride in this case). An amount less than equimolar causes unreacted ASA to remain. An amount exceeding equimolar causes the unsaturated alcohols to remain and further provides the risk that the hydroxyl groups of the unsaturated alcohols react with the carboxyl groups of ASA-HA or ASA-HM in the presence of catalysts to form diester compounds. Accordingly, both are not preferred.

The reaction is carried out at atmospheric pressure or under pressure in a temperature range of 0 to 150° C., preferably 5 to 130° C., and more preferably 10 to 100° C. for 30 minutes to 20 hours, whereby intended ASA-AL, ASA-HA or ASA-HM can be obtained at a high yield. The reaction is an exothermic reaction, and the reaction temperature is controlled, if necessary, by heating or cooling. The temperature does not have to be maintained constant during the reaction, and the reaction temperature may be changed for the purpose of controlling the reaction rate or adjusting the viscosity of the reaction liquid.

The allyl or vinyl compound (2) thus produced having a succinic acid ester structure substituted with a hydrophobic group in the skeleton can be used in the form of the reaction solution after carrying out operations such as removal of excess unsaturated alcohols, but it can be separated, if necessary, by simple operations such as removal of the solvent. When the intended product having a high purity is required depending on uses, the compounds which are solids at room temperatures can be recrystallized in a solvent such as methanol, ethanol, isopropanol, acetone, toluene, benzene, xylene, and styrene. The allyl compounds which are liquid at room temperatures can be subjected to refining treatment with a column by conventional methods.

The allyl or vinyl compound (2) used in the present invention having a succinic acid ester structure substituted with a hydrophobic group in the skeleton can be produced as well by esterification of a succinic acid derivative which is a hydrolysis product of ASA with unsaturated alcohols, but it is more preferred in terms of the reactivity to use ASA as the raw material.

The amphipathic compounds (1) and (2) described above have carboxyl groups as hydrophilic groups in the molecules, and neutralization with alkali makes them dispersible or soluble in water. Among the amphipathic compounds (1), the raw materials of the allyl compounds, such as ASA, having a succinamide structure substituted with a hydrophobic group of an internal olefin in the skeleton have a low viscosity and are liquid compounds, and the reaction can be carried out in a non-solvent system. However, since the compound itself produced by the reaction has a high viscosity, the viscosity of the reaction solution increases after the reaction, and therefore handling is difficult in some cases. Storing this product at room temperatures for long time or subjecting it to heat treatment allows the imidization easily to form an N-allylsuccinimide compound and therefore causes the amphipathic property to be lost in some cases. Accordingly, in the case where this compound is used in an aqueous solution system, since the advantages in handling that not only the imidization can be suppressed but also the viscosity can be reduced and that the solubility in water in the use is improved as well are involved, the reaction solution is preferably neutralized with alkalis such as sodium hydroxide, potassium hydroxide and ammonia, or an alkaline aqueous solution to turn the products into various salts and diluted. The examples of the salts include salts of alkali metals such as sodium, potassium and cesium, salts of alkaline earth metals such as calcium and magnesium, salts of organic bases such as trimethylamine, dimethylamine, triethylamine, diethylamine, and pyridine, and ammonium salts. However, this compound is used without neutralization in the case where the polymerization is carried out in a non-aqueous solvent system or in uses where the imidization is positively utilized. The allyl or vinyl compound (2), which is an amphipathic compound causing no imidization and having a relatively low viscosity, having a succinic acid ester structure substituted with a hydrophobic group of an internal olefin in the skeleton is neutralized immediately before using, in the case where it is used in the form of a salt in an aqueous solution. A pH value at which the compound is dispersible or soluble in water is varied depending on the kind and chain length of hydrophobic groups. For example, in the case of branched type ESA having 18 carbon atoms, the pH condition is 8 or more, and the homogeneous polymerization with hydrophilic monomers using water as the solvent is possible. The emulsion-polymerization can be carried out in the presence of surfactants even in a pH condition in which the compound is insoluble in water, and the polymerization is possible as well in a solvent dissolving both reactive surfactants and hydrophilic monomers.

The ethoxylate compound (3) obtained by reacting the allyl or vinyl compound having a succinamide or succinic acid ester structure substituted with a hydrophobic group in the skeleton with EO is obtained by reacting the compound (1) or (2) with EO in the presence of an acid or base catalyst. The ethoxylate is expressed by adding EOA and an average addition mole number (n) to the abbreviation of the precursor compound, for example, like ASA-AL-EOA (10). In the present invention, the ethoxylate is prepared by adding EO of 1 to 100 moles, preferably 2 to 80 moles to the allyl or vinyl compound having a succinamide or succinic acid ester structure substituted with a hydrophobic group in the skeleton.

Base catalysts or acid catalysts can be used as a catalyst for the EO addition reaction. The examples of the base catalysts include sodium hydroxide, potassium hydroxide and cesium hydroxide, and the examples of the acid catalysts include boron trifluoride ethyl ether complex. The catalysts are used in such an amount that when, for example, alkali metal hydroxide is used as the base catalyst, the concentration of the catalyst contained in the product after EO addition is 0.01 to 2 wt %, preferably 0.05 to 1 wt % in terms of the alkali metal hydroxide. The catalyst may remain in the product after finishing the reaction, but it is preferably neutralized with acid to adjust the pH to 4 to 10, preferably 5 to 9. The examples of the acid used for the neutralization include inorganic acids such as phosphoric acid and sulfuric acid as well as organic acids such as acetic acid and oxalic acid.

In a method for adding EO, the reaction is usually carried out by feeding EO to a mixture of the allyl or vinyl compound having a succinamide or succinic acid ester structure substituted with a hydrophobic group in the skeleton and the catalyst, and the reaction may be carried out as well, if necessary, in the presence of solvents. Any solvents can be used as the solvent suitable to the EO addition reaction as long as they do not have active hydrogens. The preferred examples thereof include aromatic hydrocarbons such as benzene and toluene, aliphatic hydrocarbons such as cyclohexane and pentane, and aprotic polar solvents such as N,N-dimethyl-2-imidazolidinone and dimethylsulfolane.

The EO addition reaction is carried out at a reaction temperature falling in a range of 50 to 200° C., preferably 70 to 150° C. The reaction is carried out at a reaction pressure falling in a range of 1 to 100 kg/cm$^2$, preferably 2 to 50 kg/cm$^2$. The reaction time is settled so that the almost all amount of EO fed is consumed in the reaction, and it is usually 0.5 to 100 hours, preferably 1 to 50 hours.

Both the raw material and the product of the ethoxylate compound (3) used in the present invention, obtained by reacting the allyl or vinyl compound having a succinamide or succinic acid ester structure substituted with a hydrophobic group in the skeleton with EO have polymerizable double bonds, and therefore it is effective to use, if necessary, a polymerization inhibitor in the production process. In particular, the derivatives of hydroxyalkyl (meth) acrylates such as ASA-HA and ASA-HM which are vinyl compounds are highly polymerizable, and therefore polymerization inhibitors are preferably used for the reaction. The same compounds as those used in producing the allyl compound (1) having a succinamide structure substituted with a hydrophobic group in the skeleton can be used as the polymerization inhibitor. The amount thereof is varied depending on the polymerization inhibitors. Usually, it falls in a range of 1 ppm to 300 weight %, preferably 50 ppm to 5 weight % based on the weight of the allyl or vinyl compound having a succinamide or succinic acid ester structure substituted with a hydrophobic group in the skeleton, which is the raw material.

The reaction can be carried out in any of a batch system, a semi-continuous system and a continuous system. When the reaction is carried out in a batch system, a reactor is charged with the allyl or vinyl compound having a succinamide or succinic acid ester structure substituted with a hydrophobic group in the skeleton, the catalyst, and if necessary, the solvent, and the reaction is carried out while feeding EO continuously or semi-continuously. On the other hand, when the reaction is carried out in a continuous system, the reaction is carried out while feeding continuously the allyl or vinyl compound having a succinamide or succinic acid ester structure substituted with a hydrophobic group in the skeleton, EO, the catalyst, and if necessary, the solvent to the reactor. The product does not have to be specifically refined and can be the finished product as it is. However, in the case where the solvent is used, the finished product can be obtained after separating the solvent by operations such as distillation.

Since this compound group has a polyethylene oxide group (hereinafter abbreviated as a PEO group) as a hydrophilic group, the solubility in water in a condition of a fixed temperature depends on the addition mole number of EO to the hydrophobic groups. The EO addition mole number giving the water solubility is varied depending on the kind and the carbon number of the hydrophobic group, and in the case of branched type ESA-AL having 18 carbon atoms, n is 11 or more in the conditions of 20° C. in pure water. Accordingly, some compounds of an ASA-AL-EOA type give water solubility even in a neutral or acid condition of pH 8 or less, and therefore the polymerization is possible in an aqueous solvent in a homogeneous system without a restriction of the pH condition.

Since ASA is an asymmetric compound, two position isomers are involved in the preceding amphipathic compounds (1) to (3) having succinic acid substituted with a hydrophobic group as a base skeleton, and a mixture of two kinds of the isomers is formed in ordinary reaction conditions. The presence of the respective isomers can be proved by detecting two kinds of corresponding carboxylic acid amide groups or carboxylic acid ester groups by means of $^1$H-NMR and $^{13}$C-NMR analytical methods. Allylamines or unsaturated alcohols are liable to form amide or ester bonds with carbons with which no hydrophobic groups are combined, and in the case of, for example, allylamines, such tendency is notably observed in diallylamine rather than allylamine, and a hydrophobic group having many carbon atoms. These existential ratios are considered to depend on a chain length of a hydrophobic group of ASA, and reaction conditions such as a reaction solvent, a reaction temperature, and a reaction concentration, but it is no problem to use both isomers without separating for ordinary uses.

The allyl compound (4) having an amide structure of phthalic acid and a derivative thereof is produced by reacting carboxylic anhydride used as a raw material, such as phthalic anhydride, tetrahydrophthalic anhydride, hexahydrophthalic anhydride, endomethylenetetrahydrophthalic anhydride, methylendomethylenetetrahydrophthalic anhydride, trimellitic anhydride, pyromellitic anhydride, chlorendic anhydride, and methyltetrahydrophthalic anhydride with allylamine (MA), diallylamine (DA) or methallylamine.

The reaction of carboxylic anhydride with allylamine, diallylamine or methallylamine is usually carried out by adding dropwise allylamine or diallylamine to an organic solvent solution of carboxylic anhydride while stirring. The organic solvents usable as a reaction solvent may be any ones as long as they dissolve both carboxylic anhydrides and allylamines, and the examples thereof include acetone, 2-butanone, benzene, toluene, xylene, pentane, hexane, cyclohexane, DMF, DMSO, THF, diethyl ether, dioxane, dichloromethane, dichloroethane, and chloroform. Alcohol solvents such as methanol, ethanol, isopropanol, methyl cellosolve, ethyl cellosolve, 2-ethylhexanol, and cyclohexanol cause partially esterification with carboxylic anhydride in some cases. However, since carboxylic anhydride is highly reactive with allylamines, and in general, ester is formed only in a small amount, alcohol solvents can be employed as well for uses in which mixing of esters do not exert great influences on the physical properties of the resins. Carboxylic anhydrides which are liquid at room temperatures can be reacted in a non-solvent system. In the case where the reaction solvent has to be removed, like a case where the reaction product is used in an aqueous system, the reaction is carried out preferably in the non-solvent system.

With respect to the amount of allylamine, diallylamine or methallylamine, an equimolar amount based on a carboxylic anhydride group is reacted. An amount less than equimolar causes carboxylic anhydride to remain, and an amount exceeding equimolar causes allylamines to form salts with the carboxyl groups of the reaction product. Accordingly, both are not preferred. Since allylamines are highly volatile, a closed type reaction vessel is preferably used. When the reaction is carried out in an open system, volatilized allylamines have to be trapped in a cooler. In such case, allylamines are added in advance in such an excess amount corresponding to the amount of allylamines to be trapped that the reaction is completed. The reaction is carried out at atmospheric pressure or under applying pressure in a temperature range of 0 to 150° C., preferably 5 to 130° C., and more preferably 10 to 100° C. for 30 minutes to 10 hours, whereby the reaction product can be obtained at a high yield. The reaction is an exothermic reaction, and the reaction temperature is controlled, if necessary, by heating or cooling. The temperature does not have to be maintained constant during the reaction, and the reaction temperature may be changed for the purpose of controlling the reaction rate or adjusting the viscosity of the reaction liquid.

Both the raw material and the product of the allyl compound (4) used in the present invention having an amide structure of phthalic acid or a derivative thereof have polymerizable double bonds, and therefore it is effective to use, if necessary, a polymerization inhibitor in the production process. The same compounds as those used in producing the allyl compound (1) having a succinamide structure substituted with a hydrophobic group in the skeleton can be used as the polymerization inhibitor. The use amount thereof is varied depending on the polymerization inhibitors to be used, and it falls usually in a range of 1 ppm to 300 weight %, preferably 50 ppm to 5 weight % based on the weight of phthalic acid or a derivative thereof which is the raw material.

The allyl compound (4) thus produced having an amide structure of phthalic acid and a derivative thereof in the skeleton can be used in the form of the reaction solution after carrying out operations such as removal of excess allylamines, but it can be separated, if necessary, in the form of a solid by a conventional method. The intended matter thus obtained can be used for various uses after providing simple operations such as removal of the solvent. When the product having a high purity is required depending on uses, the compounds can be recrystallized in a solvent such as methanol, ethanol, isopropanol, acetone, toluene, benzene, xylene, and styrene.

Further, the allyl compound (4) thus obtained having an amide structure of phthalic acid and a derivative thereof in the skeleton can be converted to various salts by neutralizing carboxylic acids with various bases for various purposes like providing water solubility. The examples of the bases include salts of alkali metals such as sodium, potassium and cesium, salts of alkaline earth metals such as calcium and magnesium, salts of organic bases such as trimethylamine, dimethylamine, triethylamine, diethylamine, and pyridine, and ammonia. However, in the case where this compound is polymerized in a non-aqueous solvent or in uses where imidization is positively utilized, it is used without neutralizing.

The allyl compound (4) of the present invention having an amide structure of phthalic acid and a derivative thereof in the skeleton can be produced as well by amidation of a hydrolysis product of a carboxylic anhydride group with allylamines, but carboxylic anhydride is preferably used as the raw material in terms of the reactivity.

The allyl or vinyl compound (4) of the present invention having an ester structure of a phthalic acid and a derivative thereof in the skeleton is a known compound and is produced by processes specified in the related arts. In general, it can be produced by the reaction of carboxylic anhydride with unsaturated alcohols as is the case with the allyl or vinyl compound (2) of the present invention having a succinic acid ester structure substituted with a hydrophobic group in the skeleton.

The novel amphipathic compound groups of the present invention are useful compounds used in many fields in the forms of modifiers for resins, additives, dispersants, and reactive surfactants.

The amphipathic compound used in the present invention has a polymerizable double bond and can be copolymerized with various ethylenically unsaturated compounds. The copolymer of the amphipathic compound used in the present invention with the ethylenically unsaturated compound is a novel polymer. The polymer includes (I) a water soluble or dispersible amphipathic high molecular compound produced by copolymerizing the amphipathic compound with a hydrophilic ethylenically unsaturated compound, (II) an emulsion produced by making use of the amphipatic compound as the reactive surfactant for emulsion-polymerization with a hydrophobic ethylenically unsaturated compound, (III) an amphipathic high molecular compound produced by copolymerizing the amphipathic compound with a hydrophilic nonionic ethylenically unsaturated compound in the presence of a colloidizing agent, and (IV) an emulsion produced by using the amphipathic high molecular compound (I) or (III) as a dispersant.

The ethylenically unsaturated compound used in the present invention is classified as follows, and the examples of the respective compounds to be used shall be given in advance. The ethylenically unsaturated compound includes a hydrophilic ethylenically unsaturated compound and a hydrophobic ethylenically unsaturated compound.

The hydrophilic ethylenically unsaturated compound is classified into a nonionic ethylenically unsaturated compound and an ionic ethylenically unsaturated compound, and the hydrophilic ethylenically unsaturated compound is at least one compound selected from each group.

The hydrophilic nonionic ethylenically unsaturated compound is classified into an unsaturated carboxylic acid amide compound, a hydrophilic nonionic vinyl compound, and a hydrophilic nonionic allyl compound, and the hydrophilic nonionic ethylenically unsaturated compound is at least one compound selected from each group.

The examples of the unsaturated carboxylic acid amide compound include acrylamide, methacrylamide, diacetoneacrylamide, N-methylacrylamide, N-methylmethacrylamide, N,N-dimethylacrylamide, N,N-dimethylmethacrylamide, N-ethylacrylamide, N-ethylmethacrylamide, N,N-diethylacrylamide, N,N-diethylmethacrylamide, N-propylacrylamide, N-acryloylpyrrolidine, N-acryloylpiperidine, N-acryloylmorpholine, N,N-di-n-propylacrylamide, N-n-butylacrylamide, N-n-hexylacrylamide, N-n-hexylmethacrylamide, N-n-octylacrylamide, N-n-octylmethacrylamide, N-tert-octylacrylamide, N-dodecylacrylamide, N-n-dodecylmethacrylamide, N,N-diglycidylacrylamide, N,N-diglycidylmethacrylamide, N-(4-glycidoxybutyl)acrylamide, N-(4-glycidoxybutyl) methacrylamide, N-(5-glycidoxypentyl)acrylamide, N-(6-glycidoxyhexyl)acrylamide, methylenebisacrylamide, N,N'-ethylenebisacrylamide, N,N'-hexamethylenebisacrylamide, and N-methylolacrylamide.

The hydrophilic nonionic vinyl compound includes N-vinyl-2-pyrrolidone, N-vinylformamide, N-vinylacetamide, N-vinyloxazolidone, N-vinyl-5-methyloxazolidone, N-vinylsuccinimide, 2-hydroxyethyl acrylate, 2-hydroxyethyl methacrylate, 3-hydroxypropyl acrylate, 3-hydroxypropyl methacrylate, 2-hydroxypropyl acrylate, and 2-hydroxypropyl methacrylate. Further, the hydrophilic nonionic allyl compound includes allyl alcohol and methallyl alcohol.

The hydrophilic ionic ethylenically unsaturated compound is classified into an unsaturated carboxylic acid compound, an ionic vinyl compound and an ionic allyl compound, and the hydrophilic ionic ethylenically unsaturated compound is at least one compound selected from each group.

The examples of the unsaturated carboxylic acid compound include acids such as acrylic acid, methacrylic acid, crotonic acid, angelic acid, tiglic acid, 2-pentenoic acid, β-methylcrotonic acid, β-methyltiglic acid, α-methyl-2-pentenoic acid, β-methyl-2-pentenoic acid, maleic acid, fumaric acid, maleic anhydride, itaconic acid, citraconic acid, mesaconic acid, glutaconic acid, α-dihydromuconic acid, 2,3-dimethylmaleic acid, 2-methylglutaconic acid, 3-methylglutaconic acid, 2-methyl-α-dihydromuconic acid and 2,3-dimethyl-α-dihydromuconic acid, and alkali metal salts, ammonium salts and organic amine salts thereof.

The ionic vinyl compound includes sulfonic acids such as vinylsulfonic acid, styrenesulfonic acid, 2-acrylamide-2-phenylpropanesulfonic acid, 2-acrylamide-2-methylpropanesulfonic acid and 2-sulfoethylacrylate, and alkali metal salts, ammonium salts and organic amine salts thereof, cationic vinyl compounds such as N,N-dimethylaminoethylacrylate (DA), N,N-dimethylaminoethylmethacrylate (DM), N,N-dimethylaminopropylacrylamide (DMAPAA) and N,N-dimethylaminopropylmethacrylamide (DMAPMA), and vinyl compounds obtained by quaternarizing DA, DM, DMAPAA and DMAPMA with dimethyl sulfate, halogenated alkyls such as methyl chloride and methyl bromide, allyl chloride, halogenated benzyls such as benzyl chloride and benzyl bromide, epihalohydrins such as epichlorohydrin and epibromohydrin, and epoxides such as propylene oxide and styrene oxide.

The ionic allyl compound includes allylamines such as allylamine, N-methylallylamine, 2-methylallylamine, diallylamine, and dimethyldiallylammonium chloride, and salts thereof, allylsulfonic acids such as allylsulfonic acid and methallylsulfonic acid, and salts thereof.

The hydrophobic ethylenically unsaturated compound is at least one compound selected from the group consisting of aromatic vinyl compounds, cyanized vinyl compounds, diene compounds, unsaturated carboxylic acid ester compounds, vinyl alkyl ether compounds, other ethylenically unsaturated compounds and hydrophobic allyl compounds.

The aromatic vinyl compound includes styrene, α-methylstyrene, α-chlorostyrene, p-tert-butylstyrene, p-methylstyrene, p-chlorostyrene, o-chlorostyrene, 2,5-dichlorostyrene, 3,4-dichlorostyrene and divinylbenzene.

The cyanized vinyl compound includes acrylonitrile, methacrylonitrile and α-chloro-acrylonitrile.

The diene compound includes diolefin compounds such as butadiene, isoprene, allene and 2-chloro-1,3-butadiene, and chloroprene.

The unsaturated carboxylic acid ester compound includes methyl acrylate, methyl methacrylate, ethyl acrylate, ethyl methacrylate, propyl acrylate, propyl methacrylate, butyl acrylate, butyl methacrylate, lauryl acrylate, lauryl methacrylate, benzyl acrylate, benzyl methacrylate, cyclohexyl acrylate, cyclohexyl methacrylate, glycidyl acrylate, glycidyl methacrylate, (di)methyl maleate, (di)ethyl maleate, (di)butyl maleate, (di)methyl fumarate, (di)ethyl fumarate, (di)butyl fumarate, (di)methyl itaconate, (di)ethyl itaconate, (di)butyl itaconate, ethyleneglycol diacrylate, ethyleneglycol dimethacrylate, diethyleneglycol diacrylate, diethyleneglycol dimethacrylate, triethyleneglycol diacrylate, triethyleneglycol dimethacrylate, tetraethyleneglycol dimethacrylate, polyethyleneglycol (meth)acrylate, 1,3-butanediol dimethacrylate, 1,4-butanediol diacrylate, 1,6-hexanediol acrylate, methoxypolyethyleneglycol (meth) acrylate, ethoxypolyethyleneglycol (meth)acrylate, propoxypolyethyleneglycol (meth)acrylate, isopropoxypolyethyleneglycol (meth)acrylate, phenoxypolyethyleneglycol (meth)acrylate, and unsaturated carboxylic acid ester compounds of epoxy acrylates and urethane acrylates.

The vinyl alkyl ether compound includes vinyl methyl ether, vinyl ethyl ether, vinyl isopropyl ether, vinyl n-propyl ether, vinyl isobutyl ether, vinyl 2-ethylhexyl ether and vinyl n-octadecyl ether.

The other ethylenically unsaturated compounds include vinyl acetate, vinyl propionate, vinyl chloride, vinylidene chloride, α-olefins (ethylene, propylene and butene, etc.), divinyl esters such as divinyl adipate and divinyl sebacate, maleimide, N-phenylmaleimide and N-cyclohexylmaleimide.

Further, the hydrophobic allyl compounds include diallyl isophthalate, diallyl terephthalate, diethyleneglycol diallylcarbonate and triallylcyanurate.

Polymerization initiators used in the present invention include water soluble initiators and oil soluble initiators, and the examples of the respective initiators shall be given in advance.

The water soluble polymerization initiators of peroxides include, for example, ammonium persulfate, potassium persulfate, hydrogen peroxide, and tert-butyl peroxide. In this case, they can be used either singly or in the form of redox initiators by combining with reducing agents. There can be used as the reducing agents, for example, sulfites, hydrogensulfites, salts of low valency metals of iron, copper and cobalt, etc., hypophosphorous acid, hypophosphites, organic amines such as N,N,N',N'-tetramethylethylenediamine and reducing sugars such as aldose and ketose. The azo compound initiators include 2,2'-azobis-2-amidinopropane hydrochloride, 2,2'-azobis-2,4-dimethylvaleronitrile, 4,4'-azobis-4-cyanovaleic acid and salts thereof. Further, the polymerization initiators described above may be used in combination of two or more kinds thereof.

The addition amount of the polymerization initiators falls in a range of 0.0001 to 10 weight %, preferably 0.01 to 8 weight % based on the weight of monomers. In the case of the redox initiators, the addition amount of the reducing agents is 0.1 to 100 %, preferably 0.2 to 80 % based on moles of the polymerization initiators.

The oil soluble initiators of the peroxides include benzoyl peroxide, dichlorobenzoyl peroxide, dicumyl peroxide, di-tert-butyl-peroxide, 1,1,3,3-tetramethylbutyl peroxide, 2,5-dimethylhexane-2,5-dihydroperoxide, cumene hydroperoxide, tert-butyl perbenzoate, tert-butyl peracetate, tert-butyl perphenylacetate, tert-butyl peroxylaurate and cumyl perpivalate. The azo compound initiators include azobisisobutyronitrile, 2,2'-azobis(4-methoxy-2,4-dimethylvaleronitrile), 2,2'-azobis(2,4-dimethylvaleronitrile), 2,2'-azobisisobutyronitrile, 1,1'-azobis (cyclohexane-1-carbonitrile), 2-phenylazo-4-methoxy-2,4-dimethylvaleronitrile, 2,2'-azobis(2,4,4-trimethylpentane), 2,2'-azobis(2-methylpropane) and dimethyl 2,2'-azobis(2-methylpropionate). Further, the polymerization initiators described above can be used in combination of two or more kinds thereof.

The addition amount of the polymerization initiators falls in a range of 0.0001 to 10 weight %, preferably 0.01 to 8 weight % based on the weight of monomers.

In the polymerization reaction of the present invention, chain transfer agents and if necessary, pH controllers may be added for the purpose of controlling the molecular weight or the polymerization rate, and the examples of the respective compounds shall be given in advance.

The chain transfer agents include water soluble chain transfer agents and oil soluble chain transfer agents. The water soluble chain transfer agents include isopropyl alcohol, α-thioglycerol, mercaptosuccinic acid, thioglycolic acid, triethylamine and sodium hypophosphite. They are suitably used singly or in a mixture of two or more kinds thereof. The oil soluble chain transfer agents include mercaptans such as hexylmercaptan octylmercaptan, dodecylmercaptan, tetradecylmercaptan, cetylmercaptan, and stearylmercaptan, xanthogene disulfides such as dimethylxanthogene disulfide, diethylxanthogene disulfide, and diisopropylxanthogene disulfide, thiuram disulfides such as tertamethylthiuram disulfide, tertaethylthiuram disulfide, and tertabutylthiuram disulfide, terpenoids such as terpinolene, α-methylstyrene dimer, 2-ethylhexyl thioglycolate, 3-phenyl-l-pentene, 1,4-cyclohexadiene, hydroquinone, t-butylcatechol, 2,6-di-tert-butyl-4-methylphenol, 2,6-xylenol, cysteamine, sulfur, and nitroso compounds. They can suitably be used singly or in a mixture of two or more kinds thereof. The pH controllers include inorganic acids such as hydrochloric acid, sulfuric acid, phosphoric acid, and boric acid, organic acids such as formic acid, acetic acid, succinic acid, citric acid, tartaric acid and L-ascorbic acid, inorganic bases such as sodium hydroxide, potassium hydroxide and ammonia, organic bases such as ethanolamine, trimethylamine and triethylamine, and salts such as sodium hydrogencarbonate, sodium carbonate, sodium acetate and sodium dihydrogenphosphate. Further, for the purposes of masking metal ions and controlling the polymerization rate, there may be used in combination, compounds such as sodium ethylenediaminetetraacetate (EDTA-Na), citric acid, tartaric acid, urea, thiourea, L-ascorbic acid, ethylenetrithiocarbonate, phenothiazine and nicotinic acid amide. The amounts of the pH controllers, the chain transfer agents, the metal masking agents and the polymerization rate controllers are varied depending on use. In general, the amount of the pH controllers falls in a range of 100 ppm to 10%, and the amounts of the chain transfer agents and the other additives fall in a range of 1.0 ppm to 5.0% each based on the weight of the monomers.

A method for polymerizing the amphipathic compound used in the present invention with the ethylenically unsaturated compound is not specifically restricted, and the polymerization can be carried out by known methods. Usually, the polymerization is carried out by maintaining prescribed temperatures in the presence of a radical polymerization initiator. The temperature does not have to be maintained at the same temperature during the polymerization and may suitably be changed as the polymerization goes on. The polymerization can be carried out while heating or cooling, if necessary. The polymerization temperature is varied depending on the kinds of the monomers and the polymerization initiators to be used. In the case of the single initiator, the polymerization temperature falls usually in a range of 30 to 200° C. On the other hand, in the case of the redox polymerization initiators, the temperature is lowered; when the redox polymerization is carried out in one lot, the temperature is usually −5 to 50° C.; and in the redox polymerization case where the components are added consecutively, the temperature is usually 30 to 90° C. When the amphipathic compounds having a succinamide skelton or phthalic amide skeleton are used in the acidic form (M in (1)–(4), (18)–(21) is a hydrogen atom), imide cyclization caused by dehydration may take place at high temperatures of 100° C. or higher, but no specific problems are involved in the case where the application to heat resistant resins is intended. An atmosphere in a polymerization vessel is not specifically restricted. For the purpose of carrying out rapidly the polymerization, the atmosphere is preferably substituted with inert gas such as nitrogen gas. The polymerization time is not specifically limited and is usually 1 to 40 hours.

Any solvents may be used as a polymerization solvent as long as they dissolve homogeneously the amphipathic compound and the ethylenically unsaturated compound used in the present invention. The examples of organic solvents include hexane, cyclohexane, decalin, tetralin, dioxane, carbon tetrachloride, benzene, toluene, xylene, cumene, ethylbenzene, carbon disulfide, chloroform, ethyl acetate, acetic acid, morpholine, tetrahydrofuran, pyridine, methyl ethyl ketone, acetone, alcohols such as methanol, ethanol, propanol, butanol, methyl cellosolve, ethyl cellosolve, butyl cellosolve and ethylene glycol, formamide, dimethylformamide, and dimethylsulfoxide. In particular, in uses where the solvents have to be removed after the polymerization, the copolymerization of the amphipatic compound with the ethylenically unsaturated compound which is compatible or miscible with the amphipathic compound used in the present invention is preferably carried out in a non-solvent system in some cases for the purpose of simplifying the process. The uses of the high molecular compound produced by polymerization in a non-aqueous system include plasticizers, heat resistant resins, antistatic resins, lubricants, paints, adhesives, dispersants, surfactants, and admixtures for cement.

The amphipathic compound used in the present invention has a particularly high utility value as a raw material used for producing water soluble or dispersible amphipathic compounds or water dispersible resins. The examples thereof shall concretely be explained in (I), (II), (III) and (IV).

(I) The amphipathic compound used in the present invention can be homogeneously copolymerized with the hydrophilic ethylenically unsaturated compound using water as the solvent on pH and temperature conditions that the amphipathic compound is water soluble, whereby the water soluble or dispersible amphipathic high molecular compound (I) can be produced. The amphipathic compound can be emulsion-polymerized in the presence of surfactants even on pH and temperature conditions that the amphipathic compound is insoluble in water. This amphipathic high molecular compound (I) can be produced by copolymerizing the amphipathic compound represented by any of Formulas (5) to (8), Formulas (18) to (21) and Formulas (22) to (25), or a mixture thereof with the hydrophilic ethylenically unsaturated compound in an aqueous solvent by known methods. Usually, the polymerization is carried out by maintaining the polymerizing solution at prescribed temperatures in the presence of a radical polymerization initiator. The temperature does not have to be maintained at the same temperature during the polymerization and may suitably be changed as the polymerization goes on. The polymerization is carried out while heating or cooling, if necessary. The polymerization temperature is varied depending on the kinds of the monomers and the polymerization initiators to be used. In the case of the single initiator, the polymerization temperature falls usually in a range of 30 to 100° C. On the other hand, in the case of the redox polymerization initiators, the temperature is lowered; when the redox polymerization is carried out in one lot, the temperature is usually −5 to 50° C.; and in the redox polymerization case where the components are added consecutively, the temperature is usually 30 to 90° C. An atmosphere in a polymerization vessel is not specifically restricted. For the purpose of carrying out rapidly the polymerization, the atmosphere is preferably substituted with inert gas such as nitrogen gas. The polymerization time is not specifically limited and is usually 1 to 40 hours.

Water is used for a polymerization solvent, and organic solvents such as methanol, ethanol, isopropanol, acetone, ethylene glycol, and propylene glycol may be used in combination. The amphipathic compound, the monomers, the solvent, the polymerization initiator, and the chain transfer agent which all are used for the polymerization may be charged into a reaction vessel in one lot at the time when the polymerization starts, or one or more components may be added singly or in the form of a mixture thereof with the solvent consecutively as the polymerization proceeds.

In producing the amphipathic high molecular compound (I) by copolymerizing the amphipathic compound with the hydrophilic ethylenically unsaturated compound, a hydrophobic ethylenically unsaturated compound may be used as a copolymerizable component for the purpose of increasing the hydrophobicity. In this case, an excess amount of the hydrophobic ethylenically unsaturated compound used causes a problem that the water dispersibility of the amphipathic high molecular compound substantially disappeared and that the particles of the hydrophobic resin dispersed only by the amphipathic compound as the emulsifier are formed. Accordingly, in general, the amount of the hydrophobic ethylenically unsaturated compound is preferably 30% or less based on the hydrophilic ethylenically unsaturated compound.

In general, the amphipathic high molecular compound (I) of the present invention thus obtained is suitably used for plasticizers, heat resistant resins, antistatic agents, lubricants, paints, adhesives, dispersants, thickeners, high molecular surfactants and admixtures for cement. In particular, it can preferably be used for a paper making additive containing the above compound as an effective ingredient. Among them, the amphipathic high molecular compound (I) of the present invention, which is soluble or dispersible in water, has a high utility value as a novel sizing agent which can improve paper reinforcing performance.

The amphipathic high molecular compound (I) of the present invention has a viscosity falling in a range of 0.01 to 500 poise at a concentration of 5 to 30 weight % at 25° C. Since the amphipathic high molecular compound (I) of the present invention is water dispersible in itself unlike ASA and other phthalic acid group compounds which are the starting materials, it does not have to be emulsified with surfactants and can be used as it is.

(II) The amphipathic compound used in the present invention is a useful compound as a reactive surfactant, and a water dispersible type resin composition (II) produced by emulsion-polymerizing the above reactive surfactant with the ethylenically unsaturated compound has an ability to form a polymer film which is particularly excellent in heat resistance and water resistance. That is, the water dispersible type resin composition (II) is obtained by emulsion-polymerizing the reactive surfactant represented by any of Formulas (5) to (8), Formulas (18) to (21) and Formulas (22) to (25), or a mixture thereof [A] of 0.1 to 50 weight % with the ethylenically unsaturated compound [B] of 50 to 99.9 weight %.

A hydrophobic ethylenically unsaturated compound is mainly used for the ethylenically unsaturated compound. However, a hydrophilic ethylenically unsaturated compound which is usually used for the purpose of improving the stability of polymers may be added in the polymerization. The amount thereof falls usually in a range of 0.1 to 20 weight % based on the weight of the hydrophobic ethylenically unsaturated compound.

The polymerized amounts of the reactive surfactant [A] and the emulsion-polymerizable ethylenically unsaturated compound [B] fall usually in a range of 0.1 to 20 weight % for [A] and 80 to 99.9 weight % for [B], preferably 0.5 to 10 weight % for [A] and 90 to 99.5 weight % for [B] based on the total weight of the whole monomers. An amount of [A] of less than 0.1 weight % lowers the emulsification stability of the resin composition of the present invention, and the amount exceeding 20 weight % reduces the water resistance of a dried film of the resin composition.

The water dispersible type resin composition (II) of the present invention can be produced by known emulsion-polymerization methods in the presence of a pH controller, a chain transfer agent, a metal masking agent, and a protective colloid agent according to necessity.

There can be used as the protective colloid agent, partially saponified polyvinyl alcohol, polyvinylpyrrolidone, carboxymethyl cellulose, methyl cellulose, hydroxyethyl cellulose, hydroxypropyl cellulose and acrylamide. In general, the amount of the protective colloid agent falls in a range of 0.1 to 20%, preferably 0.1 to 10% based on the whole amount of the monomers.

A method for emulsion-polymerizing the ethylenically unsaturated compound is not specifically restricted, and the polymerization can be carried out by known methods. Usually, the polymerization is carried out by maintaining the polymerizing solution at prescribed temperatures in the presence of a radical polymerization initiator. The temperature does not have to-be maintained at the same temperature during the polymerization and may suitably be changed as the polymerization goes on. The polymerization is carried out while heating or cooling, if necessary. The polymerization temperature is varied depending on the kinds of the monomers and the polymerization initiators to be used. In the case of the single initiator, the polymerization temperature falls usually in a range of 30 to 200° C. On the other hand, in the case of the redox polymerization initiators, the temperature is lowered; when the redox polymerization is carried out in one lot, the temperature is usually −5 to 50° C.; and in the redox polymerization case where the components are added consecutively, the temperature is usually 30 to 90° C. An atmosphere in a polymerization vessel is not specifically restricted. For the purpose of carrying out rapidly the polymerization, the atmosphere is preferably substituted with inert gas such as nitrogen gas. The polymerization time is not specifically limited and is usually 1 to 40 hours.

Water is used for a polymerization solvent, and organic solvents such as methanol, ethanol, isopropanol, acetone, ethylene glycol, and propylene glycol may be used in combination.

The reactive surfactant, the ethylenically unsaturated compound, the polymerization initiator, the solvent, and the chain transfer agent which are-used for the polymerization may be charged into a reaction vessel in one lot at the time when the polymerization starts, or one or more components may be added singly or in the form of a mixture thereof with the solvent, for example, an emulsion solution of the ethylenically unsaturated compound, consecutively as the polymerization proceeds.

The reactive surfactant of a type having a carboxyl group, represented by any of Formulas (18) to (21) and Formulas (22) to (25) is usually used in the form of a salt. In addition, possible is a method in which the reactive surfactant is dissolved in the hydrophobic ethylenically unsaturated compound or a mixture containing the hydrophobic ethylenically unsaturated compound without neutralizing the carboxyl group to carry out the emulsion-polymerization on a weak acidic to neutral condition. However, in this case the polymerization system is unstable, and coagulated matters are liable to be formed. Effective for preventing this are a method in which the polymerization is carried out while neutralizing by adding alkali to the polymerization system and a method in which known surfactants are used in combination. When alkali is not added, it is preferred from the viewpoint of stabilizing the emulsion to neutralize the carboxyl group by adding alkali after the emulsion-polymerization. However, in order to enhance the heat resistance, the emulsion may be used without neutralization.

The reactive surfactant contained in the emulsion thus obtained is usually in the form of a carboxylic acid salt and contributes to the stabilization of the emulsion. A polymer film produced from this emulsion is improved in water resistance as compared with the case where a non-polymerizable surfactant is used. If the film is subjected to acid treatment and then to heat treatment, the water resistance is further improved, and the heat resistance is enhanced as well. Acid used for the acid treatment is either or both of an inorganic acid such as hydrochloric acid, sulfuric acid and phosphoric acid and an organic acid such as formic acid, acetic acid and citric acid. The heat treatment temperature and time can suitably be changed depending on the film thickness and the polymer composition, and the heat treatment is usually carried out in the ranges of 80 to 150° C. and of some seconds to some ten minutes. The heat treatment is carried out in the air or an inert gas such as nitrogen and argon.

The water dispersible type resin composition (II) of the present invention may further contain, if necessary, additives such as preservatives, defoaming agents, cross-linking agents, viscosity controllers, film forming aids, plasticizers, antistatic agents, sticking agents, freezing stabilizers, pigments, fillers and dyes.

The water dispersible resin composition (II) of the present invention is used in the fields of plasticizers, heat resistant resins, antistatic resins, lubricants, paints, adhesives, additives for cement and paper making additives.

(III) The amphipathic high molecular compound can be synthesized by copolymerizing the reactive surfactant with the hydrophilic, nonionic ethylenically unsaturated compound. In such amphipathic high molecular compound, interaction works between the hydrophobic groups in an aqueous medium, and therefore a high molecular micelle structure is formed in such a low concentration range as 1% or less. However, on the condition of an increase in the molecular weight of the amphipathic high molecular compound or an increase in the solution concentration, hydrophobic group interaction comes to work between the molecules of the amphipathic high molecular compound, and therefore the solution viscosity increases markedly. Known is a technique in which the amphipathic high molecular compound is used as a thickener of an association type for improving rheology of aqueous paint and synthetic latex utilizing such property.

However, in the cases where the viscosity of the aqueous solution does not have to be increased, for example, in the case where the amphipathic high molecular compound is used for dispersing hydrophobic compounds as a high molecular surfactant, or in the case where it is used for paper making additives such as a sizing agent, such thickening effect as described above is not preferred in some cases. That is, in such uses, the amphipathic high molecular compound is transported or used preferably in the form of an aqueous solution. However, an increase in the molecular weight of the amphipathic high molecular compound results in higher solution viscosity, and to a large extent causing the fluidity to be lost, thereby making handling difficult. While the polymerization carried out in the lowered concentration produces the high molecular compound of a high molecular weight, there has been a problem that from the view point of production efficiency and the transportation efficiency, there exists a fixed upper limit in the molecular weight of the amphipathic high molecular compound which can be substantially produced, depending on the concentration of the amphipathic high molecular compound.

In the copolymerization of the reactive surfactant used in the present invention with the hydrophilic, nonionic ethylenically unsaturated compound, it has been found that the amphipathic high molecular compound having a higher molecular weight and a lower viscosity in an aqueous solution, as compared with those in conventional methods, can be produced by adding continuously or intermittently a compound (hereinafter referred to as a "colloidizing agent") having an ability to substantially lower the solubility of the reactive surfactant in water.

The present invention relates to a process for producing the amphipathic high molecular compound (III), characterized by that the reactive surfactant represented by Formulas (5) to (8), Formulas (18) to (21) and Formulas (22) to (25) is copolymerized with the hydrophilic, nonionic ethylenically unsaturated compound in the presence of the colloidizing agent.

That is, the amphipathic high molecular compound (III) can be produced by copolymerizing the above reactive surfactant of 0.1 to 90 weight % with the hydrophilic, nonionic ethylenically unsaturated compound of 10 to 99.9 weight % in the presence of the colloidizing agent of 0.1 to 10 moles per mole of the reactive surfactant.

The colloidizing agent is a compound having an ability to lower the solubility in water of the above reactive surfactant, and the examples of the colloidizing agent are classified into compound groups of inorganic acids, organic acids, inorganic bases, organic bases, and salts of the respective acids and bases described above. The colloidizing agents are used singly or in optional combination of two or more kinds thereof. The colloidizing agent is used in a range of 0.1 to 10 moles, preferably 0.2 to 5 moles per mole of the reactive surfactant.

The examples of inorganic acids include hydrochloric acid, nitric acid, sulfuric acid, phosphoric acid, and boric acid. The examples of the organic acids include carboxylic acid compounds such as formic acid, acetic acid, succinic acid, citric acid, tartaric acid, L-ascorbic acid, and unsaturated carboxylic acid compounds such as acrylic acid, methacrylic acid, crotonic acid, angelic acid, tiglic acid, 2-pentenoic acid, β-methylcrotonic acid, β-methyltiglic acid, α-methyl-2-pentenoic acid, β-methyl-2-pentenoic acid, maleic acid, fumaric acid, maleic anhydride, itaconic acid, citraconic acid, mesaconic acid, glutaconic acid, α-dihydromuconic acid, 2,3-dimethylmaleic acid, 2-methylglutaconic acid, 3-methylglutaconic acid, 2-methyl-α-dihydromuconic acid and 2,3-dimethyl-α-dihydromuconic acid, and unsaturated sulfonic acid compounds such as vinylsulfonic acid, styrenesulfonic acid, 2-acrylamide- 2-phenylpropanesulfonic acid, 2-acrylamide-2-methylpropanesulfonic acid, allylsulfonic acid and methallylsulfonic acid.

The examples of the inorganic bases include lithium hydroxide, sodium hydroxide, potassium hydroxide, sodium carbonate, sodium hydrogencarbonate and ammonia. The examples of the organic bases include hydrazine, ethylenediamine, ethanolamine, dimethylamine, diethylamine, trimethylamine, triethylamine and salts thereof, basic vinyl compounds such as N,N-dimethylamino ethylacrylate (DA), N,N-dimethylaminoethyl methacrylate (DM), N,N,-dimethylamino ethylacrylate, N,N-dimethylamino ethylmethacrylate, N,N-diethylaminoethyl acrylate, N,N-diethylaminoethyl methacrylate, N,N-dimethylaminopropylacrylamide (DMAPAA), N,N-dimethylaminopropylmethacrylamide (DMAPMA) and salts thereof, and allylamines such as allylamine, N-methylallylamine, 2-methylallylamine, and diallylamine and salts thereof. Further included are vinyl compounds obtained by quaternizing DA, DM, DMAPAA and DMAPMA with dimethyl sulfate, halogenated alkyls such as methyl chloride and methyl bromide, allyl chloride, halogenated benzyls such as benzyl chloride and benzyl bromide, epihalohydrins such as epichlorohydrin and epibromohydrin, and epoxides such as propylene oxide and styrene oxide, and dimethyldiallylammonium chloride.

The amphipathic high molecular compound (III) of the present invention can be produced by copolymerizing the reactive surfactant with the hydrophilic, nonionic ethylenically unsaturated compound in an aqueous medium by known methods while adding continuously or intermittently the above colloidizing agent. Usually, the polymerization is carried out by maintaining the polymerizing solution at prescribed temperatures in the presence of a radical polymerization initiator. The temperature does not have to be maintained at the same temperature during the polymerization and may suitably be changed as the polymerization goes on. The polymerization is carried out while heating or cooling, if necessary. The polymerization temperature is varied depending on the kinds of the ethylenically unsaturated compound and the polymerization initiators to be used. In the case of the single initiator, the polymerization temperature falls usually in a range of 30 to 100° C. On the other hand, in the case of a redox polymerization initiators, the temperature is lowered; when the redox polymerization is carried out in one lot, the temperature is usually −5 to 50° C.; and in the redox polymerization case where the components are added consecutively, the temperature is usually 30 to 90° C. An atmosphere in a polymerization vessel is not specifically restricted. For the purpose of carrying out rapidly the polymerization, the atmosphere is preferably substituted with inert gas such as nitrogen gas. The polymerization time is not specifically limited and is usually 1 to 40 hours.

Water is used as a polymerization solvent, and organic solvents such as methanol, ethanol, isopropanol, acetone, ethylene glycol, and propylene glycol may be used in combination.

The amphipathic high molecular compound (III) of the present invention can be produced by using a pH controller, a chain transfer agent, and a metal masking agent, if necessary.

The reactive surfactant, the ethylenically unsaturated compound, the solvent, the polymerization initiator, and the chain transfer agent which all are used for the polymerization may be charged into a reaction vessel in one lot at the time when the polymerization starts, or one or more components may be added singly or in the form of a mixture thereof with the solvent consecutively as the polymerization proceeds. The colloidizing agent may be blended with the addition solution but has to be so added separately that the reactive surfactant and the colloidizing agent are not contained in the same solution. Further, in the case of the reactive surfactant having a carboxyl group before the polymerization, a pH of the solution is adjusted to 7 or more with the a pH controller that the carboxyl group is turned into the alkali metal salt or ammonium salt. The colloidizing agent is usually added continuously or intermittently in 10 minutes to 40 hours, and the reactive surfactant has to be charged into the reaction vessel at least before finishing the addition of the colloidizing agent.

The amphipathic high molecular compound (III) of the present invention may further contain, if necessary, preservatives, defoaming agents, cross-linking agents, viscosity controllers, film forming aids, plasticizers, antistatic agents, sticking agents, freezing stabilizers, pigments, fillers, and dyes.

The amphipathic high molecular compound (III) thus obtained is characterized by a higher molecular weight and a viscosity reduced to a large extent in the same concentration as compared with those of the amphipathic high molecular compound (I), and it is used in the fields of plasticizers, heat resistant resins, antistatic agents, lubricants, paints, adhesives, admixtures of cement and paper making additives, and for uses in which high molecular surfactants are used.

(IV) Known is a technique in which functional groups are introduced on the surface of the particles of a high molecular emulsion to control reactivity and charging state on the surface of the emulsion and to improve a mechanical stability of the emulsion. Further, as a method in which highly hydrophilic functional groups are caused to be distributed on the surface phase of emulsion particles, known is a method in which a hydrophilic ethylenically unsaturated compound and a hydrophobic ethylenically unsaturated compound are copolymerized by soap-free emulsion polymerization. However, involved in this method is the problem that while heteromorphologic structure particles in which a highly hydrophilic ethylenically unsaturated compound unit is distributed on the surface phase thereof are naturally formed, the amount of the hydrophilic high molecular compound eluted in the aqueous phase in the polymerization process without staying on the particle surface can not be ignored, and therefore the intended particles can not efficiently be produced.

Further, known is a method in which particles having a heteromorphologic structure are produced with a hydrophilic high molecular compound used as a seed. It is known that in this case, a distribution in a hydrophobic high molecular compound after polymerization is affected to a large extent by the cross-linking degree of the seed particles and an increase in the cross-linking degree usually causes a hydrophobic high molecular phase to be distributed in the vicinity of the particle surface. On the other hand, there is the problem that in the case where a hydrophilic high molecular compound having a low cross-linking degree is used for the seed, the amount of the hydrophilic high molecular compound which is present free from particles can not be ignored.

The amphipathic high molecular compound (I) or (III) is useful as a high molecular type surfactant and has made it possible to efficiently produce the water dispersible type resin composition (IV), that is, the water dispersible particles having a heteromorphologic structure covered with a highly hydrophilic polymer, which have been insufficiently formed by conventional techniques, by emulsion-polymerizing a hydrophobic ethylenically unsaturated compound in the presence of the compound (I) or (III).

The hydrophobic ethylenically unsaturated compound is mainly used for the ethylenically unsaturated compound. However, a hydrophilic ethylenically unsaturated compound which is usually used for the purpose of improving the stability of polymers may be added in the polymerization. The amount thereof falls usually in a range of 0.1 to 20 weight % based on the weight of the hydrophobic ethylenically unsaturated compound.

The amphipathic high molecular compound [C] used in the present invention is the amphipathic high molecular compound (I) or (III) described above. With respect to the composition ratio of compound [C] to the ethylenically unsaturated compound [D], the compound [C] of less than 1 weight % based on the total weight of the compounds [C] and [D] in terms of solids lowers the emulsification stability of the resin composition of the present invention and therefore is not preferred. Accordingly, the ratio of [C] falls in a range of 1 to 99 weight % and that of [D] in a range of 99 to 1 weight %, preferably that of [C] in a range of 5 to 90 weight % and that of [D] in a range of 95 to 10 weight %.

The water dispersible type resin composition (IV) of the present invention can be produced by known emulsion-polymerization methods in the presence of a pH controller, a chain transfer agent, a protective colloid agent and a known surfactant, according to necessity. The compounds exemplified in the water dispersible type resin composition (II) can be used as the protective colloid agent. The use amount thereof falls usually in a range of 0.1 to 20%, preferably 0.1 to 10% based on the whole amount of the ethylenically unsaturated compounds.

A method for emulsion-polymerizing the ethylenically unsaturated compound is not specifically restricted, and the polymerization can be carried out by known methods. Usually, the polymerization is carried out by maintaining the polymerizing solution at prescribed temperatures in the presence of a radical polymerization initiator. The temperature does not have to be maintained at the same temperature during the polymerization and may suitably be changed as the polymerization goes on. The polymerization is carried out while heating or cooling, if necessary. The polymerization temperature is varied depending on the kinds of the ethylenically unsaturated compound and the polymerization initiators to be used. In the case of the single initiator, the polymerization temperature falls usually in a range of 30 to 200° C. On the other hand, in the case of a redox polymerization initiator, the temperature is lowered; when the redox polymerization is carried out in one lot, the temperature is usually −5 to 50° C.; and in the redox polymerization case where the components are added consecutively, the temperature is usually 30 to 90° C. An atmosphere in a polymerization vessel is not specifically restricted. For the purpose of carrying out rapidly the polymerization, the atmosphere is preferably substituted with inert gas such as nitrogen gas. The polymerization time is not specifically limited and is usually 1 to 40 hours.

Water is used as a polymerization solvent, and organic solvents such as methanol, ethanol, isopropanol, acetone, ethylene glycol, and propylene glycol may be used in combination.

The high molecular surfactant, the ethylenically unsaturated compound, the polymerization initiator, the solvent, and the chain transfer agent which all are used for the polymerization may be charged into a reaction vessel in one lot at the time when the polymerization starts, or one or more components may be added singly or in the form of a mixture thereof with the solvent, for example, an emulsion solution into which the ethylenically unsaturated compound is turned in the presence of the high molecular surfactant, consecutively as the polymerization proceeds.

The water dispersible type resin composition produced in the present invention is basically of spherical particles and composed of a hydrophobic polymer in the inner part and a hydrophilic polymer in the outer part. The above resin composition is characterized in that the hydrophilic polymer free from the particles is scarcely present. The high molecular surfactant of the present invention forms particles in a diluted aqueous solution, and the size thereof can be determined by a dynamic light scattering method. It is supported by the fact that the diameter of particles contained in the emulsion prepared by polymerizing the hydrophobic ethylenically unsaturated compound remains unchanged until the amount of the hydrophobic ethylenically unsaturated compound reaches some fixed amount based on the high molecular surfactant, but as the amount of the hydrophobic ethylenically unsaturated compound grows exceeding the above fixed amount, the diameter of the particles contained in the emulsion increases, and the particles having a particle diameter observed in the case of the high molecular surfactant alone cease to be present.

The water dispersible type resin composition (IV) of the present invention may further contain, if necessary, additives such as preservatives, defoaming agents, cross-linking agents, viscosity controllers, film forming aids, plasticizers, antistatic agents, sticking agents, freezing stabilizers, pigments, fillers and dyes.

The water dispersible type resin composition (IV) of the present invention is used in the fields of plasticizers, heat resistant resins, antistatic agents, lubricants, paints, adhesives, additives for cement, and paper making additives.

The amphipathic high molecular compounds (I) and (III) and the water dispersible type resin composition (IV) according to the present invention provide paper with a sizing property and enhance as well paper strength to a large extent by coating them on the surface of paper. The concentration of a coating solution in coating on paper falls in a range of 0.01 to 10.0%, preferably 0.10 to 8.0%. The coated amount thereof falls in a range of 0.001 to 5.0 g/m$^2$, preferably 0.005 to 1.0 g/m$^2$. Coating on paper is carried out by conventional methods such as impregnation, size press, gate roll coater, calendering, blade coater, and spraying. The drying temperature after coating may be temperatures at which water is evaporated and falls preferably in a range of from 80° C. to 180° C. Further, the amphipathic high molecular compounds (I) and (III) and the water dispersible type resin composition (IV) according to the present invention can improve still more the surface strength and the internal strength by combining with chemicals for surface coating such as starch, carboxymethyl cellulose, PVA and PAM group which have so far been known.

Further, the amphipathic high molecular compounds (I) and (III) and the water dispersible type resin composition (IV) according to the present invention can be used in combination with pigments, other sizing agents (ASA group, AKD group, rosin group and synthetic high molecular compounds), waterproofing agents, releasing agents, defoaming agents, and rust preventives. The examples of the pigments used include inorganic pigments such as clay, light calcium carbonate, heavy calcium carbonate, titanium oxide, aluminum hydroxide, satin white, barium sulfate, magnesium oxide, talc, silica and colloidal silica, and organic pigments such as polystyrene, SBR and phenol resins. They can be used singly or in combination of two or more kinds thereof. They can be used as well in combination with dispersants, viscosity controllers, water retention aids, dyes, fluorescent dyes, solvents, pH controllers, surfactants and preservatives.

Further, the amphipathic high molecular compounds (I) and (III) and the water dispersible type resin composition (IV) according to the present invention can be fixed on pulp by interaction with aluminum sulfate, aluminum chloride, sodium aluminate, Mannich Modifications and Hofmann modifications of polyethylenimine and polyacrylamide, polyalkylenepolyamine, and water soluble polymer having a cation group such as cationic starch, which are widely used as fixing agents for improving the consumption efficiency of sizing agents. They can be used as an internal sizing agent. When they are used as the internal sizing agent, the addition amount thereof is 0.01 to 4.0 weight %, preferably 0.05 to 2.0 weight % based on the weight of pulp, and they are added at the same place as conventional internal sizing agents such as a seed box and a machine chest.

EXAMPLES

The present invention will be explained below in detail with reference to examples but the present invention shall not be restricted to these examples. In the following examples, percentage is based on weight, and viscosity is a value measured with a B type viscometer at 25° C. Molecular weight was determined by GPC analysis, wherein Shodex OH-pak SB-80M+SB-804 (manufactured by Showa Denko Co., Ltd.) was used as a column, and Na$_2$HPO$_4$—KH$_2$PO$_4$ (50 mM) —NaNO$_3$ (0.1 M) (pH 6.5) was used for the eluent. NMR analysis was carried out with an NMR spectrum measuring apparatus A500 of 500 MHz (manufactured by JEOL Ltd.), wherein a sample was dissolved homogeneously in deuterated chloroform in a concentration of about 10 to 20% w/v, and the solution was put in an NMR spectrum measuring sample tube having an outer diameter of 5 mm to determine a $^1$H- and $^{13}$C-NMR spectrum. IR analysis was carried out with an infrared analytical apparatus FT/IR-8900 (JAPAN SPECTROSCOPIC Co., Ltd.) using an aperture plate of MS-5 or KBr tablet. Elemental analysis was carried out with a CHN analytical apparatus model 2400 (manufactured by Perkin-Elmer Co., Ltd.).

In the symbols put in front of the abbreviations of the compounds, L- represents ASA of an α-olefin type; B-represents ASA of an internal olefin type; and $C_n$ represents a carbon number.

B-C$_{16}$-ESA-MA

Example 1

A four neck separable flask of 1 l equipped with a stirrer, a reflux condenser, a thermometer and a dropping funnel was charged with B-C$_{16}$-ESA (C$_{16}$ type, Colopearl Z-100 manufactured by Seiko Chemical Industries Co., Ltd.) of 645.0 g, and allylamine of 114.2 g was added dropwise thereto through the dropping funnel in 90 minutes while stirring. The reaction temperature was controlled to 32 to 42° C. by a water bath during dropping, and stirring was further continued at 40° C. for 3 hours after dropping was finished, whereby an amber highly viscous liquid of 759.2 g was obtained. While B-$C_{16}$-ESA had a viscosity of 96 cp before the reaction, the reaction product (B-$C_{16}$-ESA-MA) had a viscosity of 52,300 cp.

Elemental analysis value ($C_{23}H_{41}NO_3$); Calculated value: C: 72.78%, H: 10.89%, N: 3.69%; Measured value : C: 73.42%, H: 11.12%, N: 3.41%.

IR analysis (FIG. 1) was carried out to find that the characteristic absorption bands (C=O stretching) of the acid anhydride group in the raw material B-$C_{16}$-ESA observed in 1780 $cm^{-1}$ and 1860 $cm^{-1}$ disappeared and that instead of them, there were observed an absorption band originating in carboxylic acid (C=O stretching) in 1700 $cm^{-1}$, and absorption bands originating in amide (C=O stretching and N—H deforming) in 1640 $cm^{-1}$ and 3300 $cm^{-1}$ (N—H stretching).

Figure 2A:
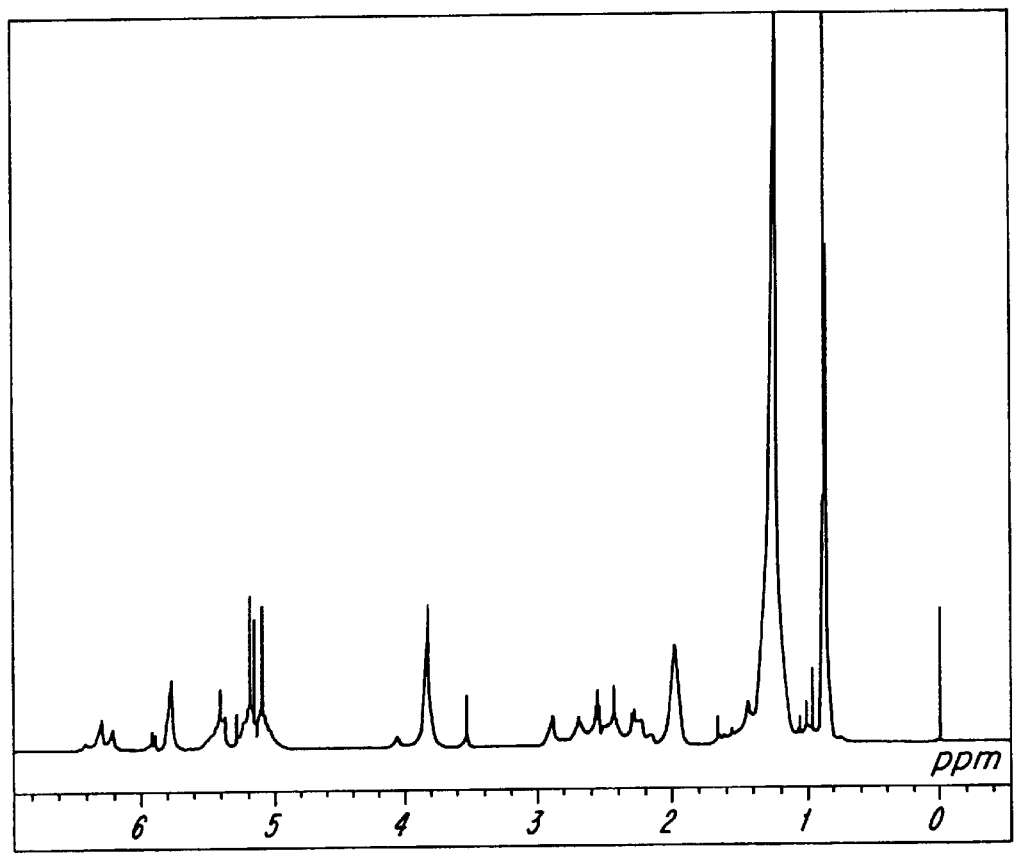
FIGS. 2a and 2b are $^1$H-NMR spectrum of the compound obtained in Example 1.
Figure 2B:
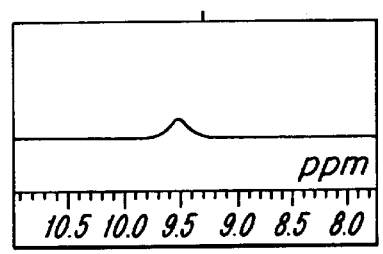
Figure 3A:
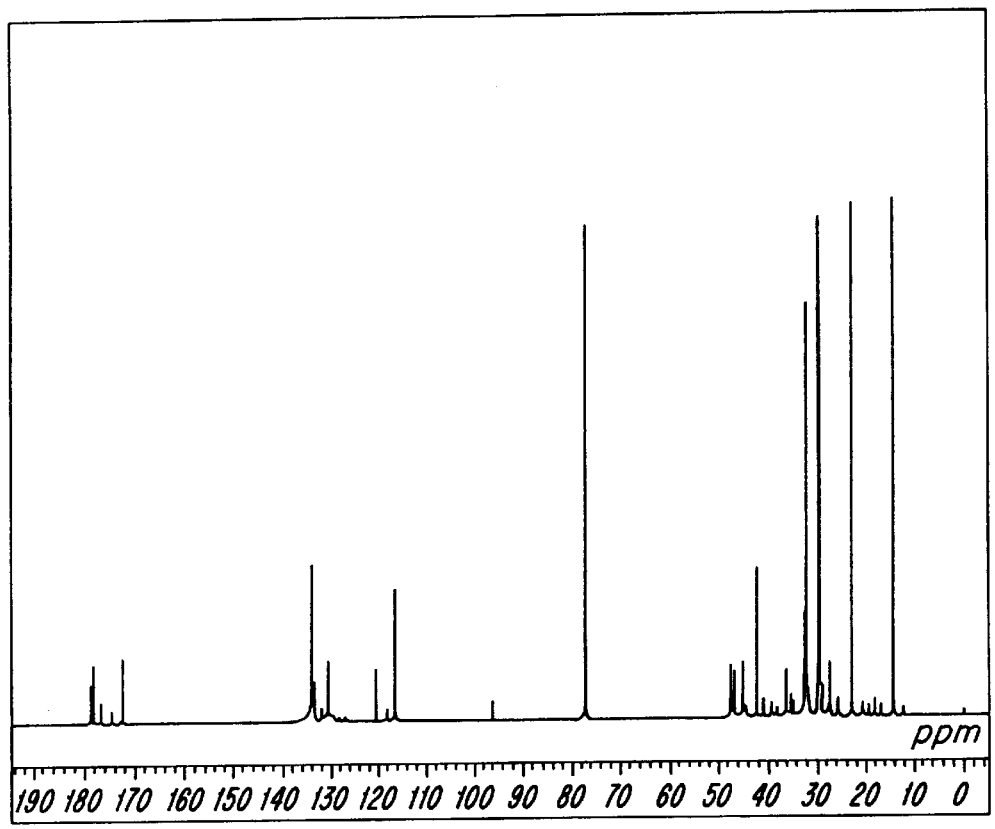
FIGS. 3a and 3b are $^{13}$C-NMR spectrum of the compound obtained in Example 1.
Figure 3B:
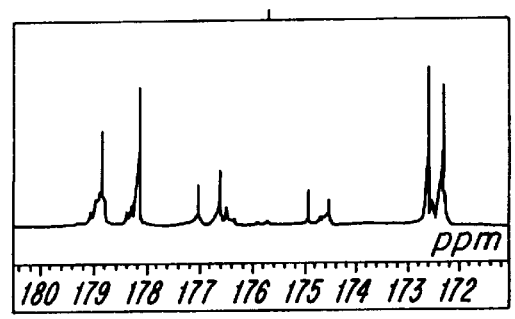

A $^1$H-NMR spectrum and a $^{13}$C-NMR spectrum of B-$C_{16}$-ESA-MA were shown in FIG. 2 and FIG. 3. The strength of a magnetic field in the axis of abscissas is shown by ppm unit on the basis (0 ppm) of tetramethylsilane. Used for the assignment of these NMR signals were various NMR determining methods such as DEPT (Distortionless Enhancement by Polarization Transfer), $^1$H-COSY (Correlation Spectroscopy), and C-H correlation COSY. In particular, carbonyl carbons were assigned by analyzing the $^{13}$C-NMR spectrum of B-$C_{16}$-ESA-MA in which the carboxyl group was esterified to methyl ester by diazomethane and a C-H correlation COSY spectrum of a long range.

As a result thereof, it was found that the signals seen in 172.3 and 172.6 ppm corresponded to the carbonyl carbon of an amide group of an isomer having the structure represented by Formula (2) out of two position isomers of B-$C_{16}$-ESA-MA and that the signals seen in 178.2 and 178.8 ppm corresponded to the carbonyl carbon of a carboxyl group of the same isomer. On the other hand, the signals seen in 174.5 and 174.9 ppm corresponded to the carbonyl carbon of an amide group of an isomer having the structure represented by Formula (1), and the signals seen in 176.6 and 177.0 ppm corresponded to the carbonyl carbon of a carboxyl group of the same isomer. Each two signals are observed in the respective carbonyl carbons, and this is considered due to the fact that two kinds of diastereoisomers are present since B-$C_{16}$-ESA-MA has two asymmetric carbons adjacent to each other in the molecule.

$^1$H-NMR (CDCl3): δ 0.88 (t, 6H, $CH_3$ of $R_1$ and $R_2$); 1.26 (m, 20H, $CH_2$ of $R_1$ and $R_2$); 1.99 (m, 2H, C*HCH=CHC$\underline{H}_2CH_2$); 2.25 (m, 1H, C*$\underline{H}$CH=CH), 2.28–2.71 (dd, 2H, COC*HC$\underline{H}_2$CO); 2.70 & 2.89 (m, 1H, COC*$\underline{H}$CH$_2$CO); 3.83 (m, 2H, NHC$\underline{H}_2$CH=CH$_2$); 4.97–5.25 (m, 1H, C*HC$\underline{H}$=CH); 5.09–5.19 (m, 2H, NHCH$_2$CH=C$\underline{H}_2$); 5.40 (m, 1H, C*HCH=C$\underline{H}$), 5.75–5.83 (m, 1H, NHCH$_2$C$\underline{H}$=CH$_2$); 6.21–6.40 (m, 1H, N$\underline{H}$CH$_2$CH=CH$_2$); 9.52 (brs, 1H, COO$\underline{H}$).

$^{13}$C-NMR (CDCl$_3$): δ 14.1 (q, 2CH$_3$); 22.7 (t, CH$_3$C$\underline{H}_2$CH$_2$); 29.1–29.8 (m, CH$_2$ of $R_1$ and $R_2$); 31.9 (t, CH$_3$CH$_2$$\underline{C}$H$_2$); 32.6 (t, C*HCH=CHC$\underline{H}_2$); 36.1 (t, COC*HC$\underline{H}_2$CO); 42.1 (t, NHC$\underline{H}_2$CH=CH$_2$); 44.9 (d, $\underline{C}$*HCH=CH); 46.7 & 47.5 (d, CO$\underline{C}$*HCH$_2$CO); 116.4 (t, NHCH$_2$CH=$\underline{C}$H$_2$); 130.2–130.8 (d, C*H$\underline{C}$H=CH); 133.2–133.7 (d, C*HCH=$\underline{C}$H); 133.9–134.2 (d, NHCH$_2$$\underline{C}$H=CH$_2$); 172.3 & 172.6 (s, $\underline{C}$OC*HCH$_2$CONH); 174.5 & 174.9 (s, COCH$_2$C*H$\underline{C}$ONH); 176.6 & 177.0 (s, $\underline{C}$OCH$_2$C*HCONH); 178.2 & 178.8 (s, $\underline{C}$OC*HCH$_2$CONH). Provided that C* represents an asymmetrical carbon.

B-$C_{16}$-ESA-MA obtained above was dissolved in water in the form of a carboxylic acid salt, and an aqueous solution (pH 8.96) prepared by dissolving homogeneously B-$C_{16}$-ESA-MA of 40.0 g, a 40% sodium hydroxide aqueous solution of 10.5 g, and distilled water of 349.5 g was used in the following examples.

B-$C_{16}$-ESA-DA

Example 2

A four neck separable flask of 1 l equipped with a stirrer, a reflux condenser, a thermometer and a dropping funnel was charged with B-$C_{16}$-ESA ($C_{16}$ type, Colopearl Z-100 manufactured By Seiko Chemical Industries Co., Ltd.) of 645.0 g, and diallylamine of 194.3 g was added dropwise thereto through the dropping funnel in 40 minutes while stirring. The reaction temperature was controlled to 20 to 30° C. by a water bath during dropping, and stirring was further continued at 30° C. for 3 hours after dropping was finished, whereby an amber highly viscous liquid of 839.3 g was obtained. B-$C_{16}$-ESA-DA had a viscosity of 1,980 cp.

Elemental analysis value ($C_{26}H_{45}NO_3$); Calculated value: C: 74.41%, H: 10.81%, N: 3.34%; Measured value: C: 74.42%, H: 11.10%, N: 3.10%.

Figure 4:
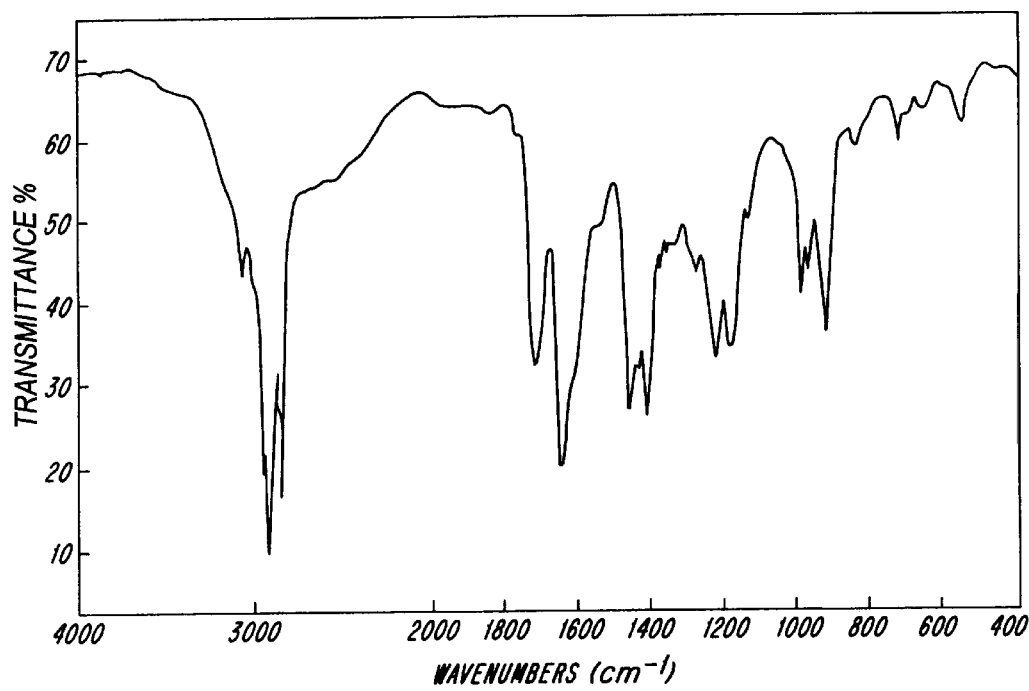
FIG. 4 is an IR absorption spectrum of the compound obtained in Example 2.
Figure 5A:
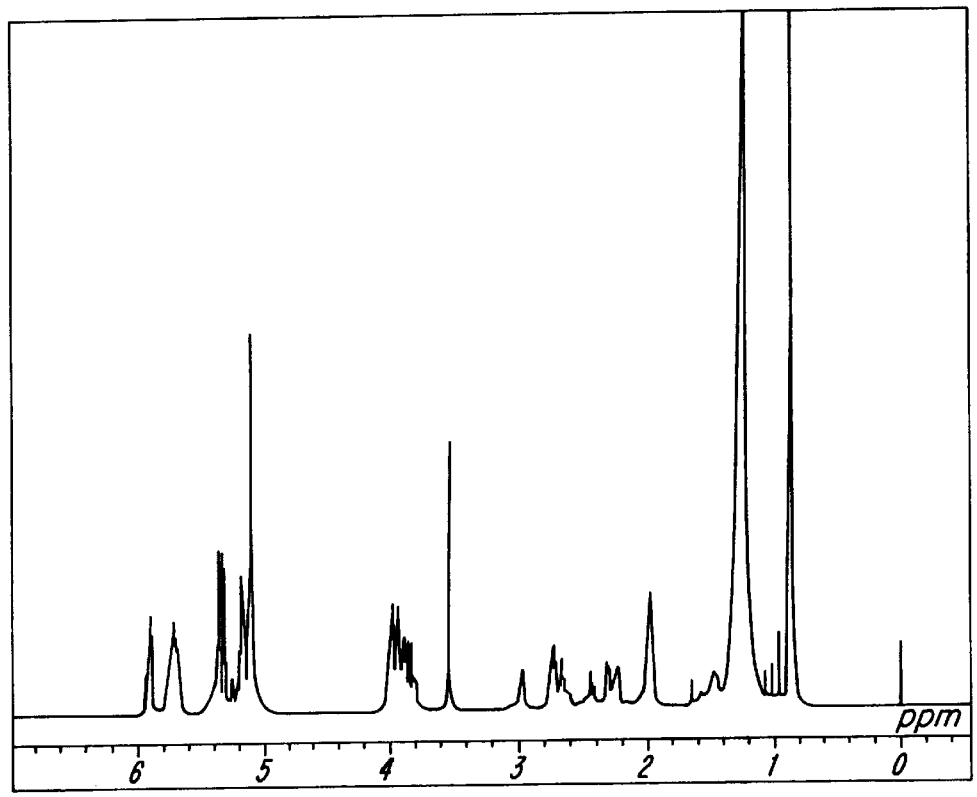
FIGS. 5a and 5b are $^1$H-NMR spectrum of the compound obtained in Example 2.
Figure 5B:
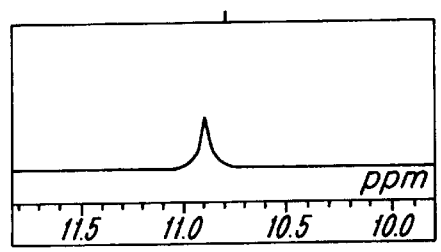
Figure 6A:
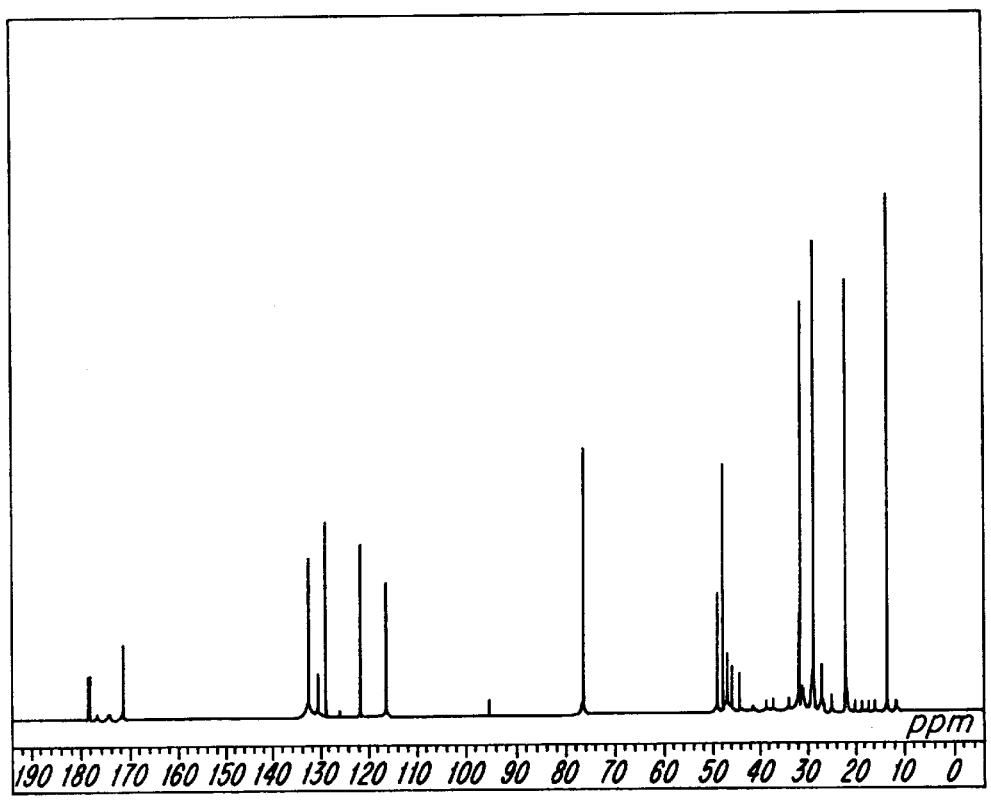
FIGS. 6a and 6b are $^{13}$C-NMR spectrum of the compound obtained in Example 2.
Figure 6B:
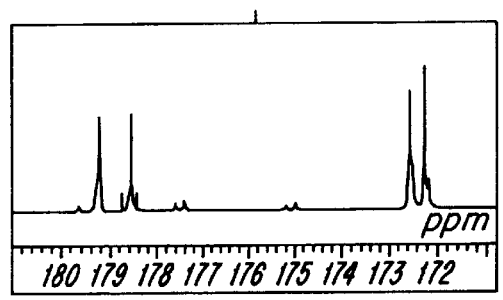

In IR analysis (FIG. 4), there were observed an absorption band originating in carboxylic acid (C=O stretching) in 1720 $cm^{-1}$, and an absorption band originating in amide (C=O stretching) in 1650 $cm^{-1}$.

A $^1$H-NMR spectrum and a $^{13}$C-NMR spectrum of B-$C_{16}$-ESA-DA were shown in FIGS. 5a and 5b and FIGS. 6a and 6b. As can be found from a carbonyl carbon range in the $^{13}$C-NMR spectrum, an amide group and a carboxyl group contained in the isomer having the structure represented by Formula (1) show very small signal strengths (175.0 & 175.2 ppm and 177.4 & 177.6 ppm) originating in the carbonyl carbons thereof. This reveals that the isomer having the structure represented by Formula (2) out of two kinds of position isomers occupy the most part in B-$C_{16}$-ESA-DA.

$^1$H-NMR (CDCl3): δ 0.88 (t, 6H, $CH_3$ of $R_1$ and $R_2$); 1.26 (m, 20H, $CH_2$ of $R_1$ and $R_2$); 1.98 (m, 2H, C*HCH=CHC$\underline{H}_2$CH$_2$); 2.24 (m, 1H, C*$\underline{H}$CH=CH), 2.29–2.78 (dd, 2H, COC*HC$\underline{H}_2$CO); 2.75 & 2.99 (m, 1H, COC*$\underline{H}$CH$_2$CO); 3.78–4.02 (m, 4H, 2NC$\underline{H}_2$CH=CH$_2$); 5.04–5.28 (m, 1H, C*HC$\underline{H}$=CH); 5.09–5.20 (m, 4H, 2NCH$_2$CH=C$\underline{H}_2$); 5.36–5.43 (m, 1H, C*HCH=C$\underline{H}$), 5.74 (m, 2H, 2NCH$_2$C$\underline{H}$=CH$_2$); 10.90 (s, 1H, COO$\underline{H}$).

$^{13}$C-NMR (CDCl$_3$): δ 14.1 (q, 2CH$_3$); 22.7 (t, CH$_3$C$\underline{H}_2$CH$_2$); 29.2–29.8 (m, CH$_2$ of $R_1$ and $R_2$); 31.9 (t, CH$_3$CH$_2$$\underline{C}$H$_2$); 32.6 (t, C*HCH=CHC$\underline{H}_2$); 32.8 (t, COC*HC$\underline{H}_2$CO); 45.1 (d, $\underline{C}$*HCH=CH); 46.5 & 47.3 (d, CO$\underline{C}$*HCH$_2$CO); 48.1 & 49.4 (t, 2N$\underline{C}$H$_2$CH=CH$_2$); 116.8–117.2 (t, 2NCH$_2$CH=$\underline{C}$H$_2$); 131.0–131.5 (d, C*H$\underline{C}$H=CH); 132.6–133.0 (d, C*HCH=$\underline{C}$H); 132.8–133.3 (d, 2NCH$_2$$\underline{C}$H=CH$_2$); 172.2 & 172.5 (s, COC*HCH$_2$$\underline{C}$ON); 175.0 & 175.2 (s, COCH$_2$C*H$\underline{C}$ON); 177.4 & 177.6 (s, $\underline{C}$OCH$_2$C*HCON); 178.5 & 179.2 (s, $\underline{C}$OC*HCH$_2$CON). Provided that C* represents an asymmetrical carbon.

B-$C_{16}$-ESA-DA obtained above was dissolved in water in the form of a carboxylic acid salt, and an aqueous solution (pH 9.02) prepared by dissolving homogeneously B-$C_{16}$-ESA-DA of 40.0 g, a 40% sodium hydroxide aqueous solution of 9.5 g, and distilled water of 350.5 g was used in the following examples.

B-C$_{18}$-ESA-MA

Example 3

A four neck separable flask of 2 l equipped with a stirrer, a reflux condenser, a thermometer and a dropping funnel was charged with B-C$_{18}$-ESA (C$_{18}$ type, Pabelas NP manufactured By Mitsubishi Oil Co., Ltd.) of 1402.2 g, and allylamine of 228.4 g was added dropwise thereto through the dropping funnel in 40 minutes while stirring. The reaction temperature was controlled to 20° C. at the beginning of dropping and 55° C. at the end of dropping by a water bath, and stirring was further continued at 40° C. for one hour after dropping was finished, whereby a reddish brown highly viscous liquid of 1,630.6 g was obtained. While B-C$_{18}$-ESA had a viscosity of 185 cp before the reaction, the reaction product (B-C$_{18}$-ESA-MA) had a viscosity of 83,900 cp.

Elemental analysis value (C$_{25}$H$_{45}$NO$_3$); Calculated value: C: 73.66%, H: 11.13%, N: 3.44%; Measured value : C: 73.88%, H: 11.53%, N: 4.03%.

IR analysis revealed that the characteristic absorption bands (C=O stretching) of the acid anhydride groups in the raw material B-C$_{18}$-ESA observed in 1780 cm$^{-1}$ and 1860 cm$^{-1}$ disappeared, and instead of them, there were observed an absorption band originating in carboxylic acid (C=O stretching) in 1700 cm$^{-1}$, and absorption bands originating in amide (C=O stretching and N—H deforming) in 1640 cm$^{-1}$ and 3300 cm$^{-1}$ (N—H stretching).

The structure of B-C$_{18}$-ESA-MA was confirmed by measuring a $^1$H-NMR spectrum and a $^{13}$C-NMR spectrum.

B-C$_{18}$-ESA-MA obtained above was dissolved in water in the form of a carboxylic acid salt, and a 80 weight % aqueous solution (pH 8.97, viscosity 3520 cp) prepared by adding a 40% sodium hydroxide aqueous solution of 186.2 g and distilled water of 54.7 g to B-C$_{18}$-ESA-MA of 759.1 g and dissolving them homogeneously was used in the following examples.

L-C$_8$ESA-MA

Example 4

A four neck separable flask of 100 ml equipped with a stirrer, a reflux condenser, a thermometer and a dropping funnel was charged with L-C$_8$-ESA (C$_8$ type, 2-octenylsuccinic anhydride manufactured By Tokyo Kasei Kogyo Co., Ltd.) of 25.1 g, and allylamine of 6.8 g was added dropwise thereto through the dropping funnel in 10 minutes while stirring. The reaction temperature was controlled to 30° C. by a water bath, and stirring was further continued at 30° C. for 5.5 hours after dropping was finished, whereby a pale yellow highly viscous liquid was obtained. The liquid was solidified by leaving for standing at room temperatures after the reaction.

Elemental analysis value (C$_{15}$H$_{25}$NO$_3$); Calculated value: C: 67.38%, H: 9.42%, N: 5.24%; Measured value : C: 67.47%, H: 9.42%, N: 5.66%.

The structure of L-C$_8$-ESA-MA was confirmed by measuring an IR spectrum, a $^1$H-NMR spectrum and a $^{13}$C-NMR spectrum.

L-C$_{10}$-ESA-MA

Example 5

L-C$_{10}$-ESA-MA was obtained by reacting equimolar allylamine in the same manner as in Example 4, except that L-C$_{10}$-ESA (C$_{10}$ type, 2-decenylsuccinic anhydride manufactured By Tokyo Kasei Kogyo Co., Ltd.) was used.

Elemental analysis value (C$_{17}$H$_{29}$NO$_3$); Calculated value: C: 69.12%, H: 9.89%, N: 4.74%; Measured value : C: 68.85%, H: 10.34%, N: 4.28%.

The structure of L-C$_{10}$-ESA-MA was confirmed by measuring an IR spectrum, a $^1$H-NMR spectrum and a $^{13}$C-NMR spectrum.

L-C$_{12}$-ESA-MA

Example 6

A four neck separable flask of 100 ml equipped with a stirrer, a reflux condenser, a thermometer and a dropping funnel was charged with L-C$_{12}$-ESA (C$_{12}$ type, 2-dodecenylsuccinic anhydride manufactured By Tokyo Kasei Kogyo Co., Ltd.) of 25.0 g, and acetone of 50 ml was added to dissolve it, followed by adding dropwise thereto allylamine of 5.4 g through the dropping funnel in 10 minutes while stirring. The reaction temperature was controlled to 25° C. by a water bath, and stirring was further continued at 25° C. for 5.5 hours after dropping was finished.

After distilling acetone off with an evaporator, the residue was recrystallized from acetone to obtain a white solid.

Elemental analysis value (C$_{19}$H$_{33}$NO$_3$); Calculated value: C: 70.55%, H: 10.28%, N: 4.33%; Measured value : C: 71.48%, H: 10.88%, N: 4.47%.

The structure of L-C$_{12}$-ESA-MA was confirmed by measuring an IR spectrum, a $^1$H-NMR spectrum and a $^{13}$C-NMR spectrum.

Examples 7 to 9

L-C$_{14}$-ESA-MA, L-C$_{16}$-ESA-MA and L-C$_{18}$-ESA-MA were obtained by reacting equimolar allylamine in the same manner as in Example 6, except that 2-tetradecenylsuccinic anhydride, 2-hexadecenylsuccinic anhydride and 2-octadecenylsuccinic anhydride were used, respectively.

L-C$_{14}$-ESA-MA (Example 7)

Elemental analysis value (C$_{21}$H$_{37}$NO$_3$); Calculated value: C: 71.75%, H: 10.61%, N: 3.98%; Measured value : C: 72.21%, H: 11.28%, N: 4.12%.

L-C$_{16}$-ESA-MA (Example 8)

Elemental analysis value (C$_{23}$H$_{41}$NO$_3$); Calculated value: C: 72.78%, H: 10.89%, N: 3.69%; Measured value : C: 73.33%, H: 11.52%, N: 3.67%.

L-C$_{18}$-ESA-MA (Example 9)

Elemental analysis value (C$_{25}$H$_{45}$NO$_3$); Calculated value: C: 73.66%, H: 11.13%, N: 3.44%; Measured value : C: 73.95%, H: 11.78%, N: 3.52%.

The structures of the three compounds described above were confirmed by measuring IR spectra, $^1$H-NMR spectra and $^{13}$C-NMR spectra.

L-C$_{12}$-PSA-MA

Example 10

A four neck separable flask of 1 l equipped with a stirrer, a reflux condenser, a thermometer and a dropping funnel was charged with L-C$_{12}$-PSA (C$_{12}$ type, MSP manufactured By Mitsubishi Oil Co., Ltd.) of 266.4 g, and allylamine of 57.1 g was added dropwise thereto through the dropping funnel in 30 minutes while stirring. The reaction temperature was controlled to 40° C. by a water bath during dropping, and stirring was further continued at 50° C. for 5 hours after dropping finished, whereby a dark brown highly viscous liquid of 323.5 g was obtained.

Elemental analysis value ($C_{19}H_{33}NO_3$); Calculated value: C: 70.55%, H: 10.28%, N: 4.33%; Measured value : C: 70.01%, H: 9.97%, N: 4.43%.

IR analysis revealed that the characteristic absorption bands (C=O stretching) of the acid anhydride groups in the raw material PSA observed in 1780 $cm^{-1}$ and 1860 $cm^{-1}$ disappeared and that instead of them, there were observed an absorption band originating in carboxylic acid (C=O stretching) in 1710 $cm^{-1}$, and absorption bands originating in amide (C=O stretching and N—H deforming) in 1640 $cm^{-1}$ and 3300 $cm^{-1}$ (N—H stretching).

The structure of L-$C_{12}$-PSA-MA was confirmed by measuring a $^1$H-NMR spectrum and a $^{13}$C-NMR spectrum.

L-$C_{12}$-PSA-MA obtained above was dissolved in water in the form of a carboxylic acid salt, and an aqueous solution (pH 8.99) prepared by adding a 40% sodium hydroxide aqueous solution of 12.4 g and distilled water of 347.6 g to L-$C_{12}$-PSA-MA of 40.0 g and dissolving them homogeneously was used in the following examples.

L-$C_{12}$-PSA-DA

Example 11

A four neck separable flask of 1 l equipped with a stirrer, a reflux condenser, a thermometer and a dropping funnel was charged with L-$C_{12}$-PSA ($C_{12}$ type, MSP manufactured By Mitsubishi Oil Co., Ltd.) of 266.4 g, and diallylamine of 97.2 g was added dropwise thereto through the dropping funnel in 15 minutes while stirring. The reaction temperature was controlled to 40° C. by a water bath during dropping, and stirring was further continued at 40° C. for 4 hours after dropping was finished, whereby a dark brown highly viscous liquid of 363.6 g was obtained.

Elemental analysis value ($C_{22}H_{37}NO_3$); Calculated value: C: 72.69%, H: 10.26%, N: 3.85%; Measured value: C: 72.29%, H: 10.30%, N: 4.04%.

Observed by IR analysis were an absorption band originating in carboxylic acid (C=O stretching) in 1720 $cm^{-1}$ and an absorption band originating in amide (C=O stretching) in 1650 $cm^{-1}$.

The structure of L-$C_{12}$-PSA-DA was confirmed by measuring a $^1$H-NMR spectrum and a $^{13}$C-NMR spectrum.

L-$C_{12}$-PSA-DA obtained above was dissolved in water in the form of a carboxylic acid salt, and an aqueous solution (pH 8.43) prepared by adding a 40% sodium hydroxide aqueous solution of 11.0 g and distilled water of 349.0 g to L-$C_{12}$-PSA-DA of 40.0 g and dissolving them homogeneously was used in the following examples.

L-$C_{24}$-BSA-MA

Example 12

A four neck separable flask of 1 l equipped with a stirrer, a ref lux condenser, a thermometer and a dropping funnel was charged with L-$C_{24}$-BSA ($C_{24}$ type, LV-7M manufactured By Nippon Petrochemicals Co., Ltd.) of 200.0 g, and acetone of 470.0 g was added to dissolve it, followed by adding dropwise thereto allylamine of 25.4 g through the dropping funnel in 30 minutes while stirring at 20° C. Stirring was continued at 20° C. for one hour after dropping finished and further for 2 hours after elevating the temperature to 40° C. The solvent contained in the reaction liquid was distilled off under reduced pressure, whereby a dark brown highly viscous liquid of 225.4 g was obtained.

Elemental analysis value ($C_{31}H_{57}NO_3$); Calculated value: C: 75.71%, H: 11.68 %, N: 2.85%; Measured value: C: 75.99%, H: 11.58%, N: 2.89%.

IR analysis revealed that the characteristic absorption bands (C=O stretching) of an acid anhydride group in the raw material L-$C_{24}$-BSA observed in 1780 $cm^{-1}$ and 1860 $cm^{-1}$ disappeared and that instead of them, there were observed an absorption band originating in carboxylic acid (C=O stretching) in 1705 $cm^{-1}$, and absorption bands originating in amide (C=O stretching and N—H deforming) in 1640 $cm^{-1}$ and 3300 $cm^{-1}$ (N—H stretching).

The structure of L-$C_{24}$-BSA-MA was confirmed by measuring a $^1$H-NMR spectrum and a $^{13}$C-NMR spectrum.

L-$C_{24}$-BSA-MA obtained above was dissolved in water in the form of a carboxylic acid salt, and an aqueous solution (pH 8.97) prepared by adding a 40% sodium hydroxide aqueous solution of 8.6 g and distilled water of 351.4 g to L-$C_{24}$-BSA-MA of 40.0 g and dissolving them homogeneously was used in the following examples.

L-$C_{24}$-BSA-DA

Example 13

A four neck separable flask of 1 l equipped with a stirrer, a reflux condenser, a thermometer and a dropping funnel was charged with L-$C_{24}$-BSA ($C_{24}$ type, LV-7M manufactured By Nippon Petrochemicals Co., Ltd.) of 200.0 g, and acetone of 470.0 g was added to dissolve it, followed by adding dropwise thereto diallylamine of 43.3 g through the dropping funnel in 37 minutes while stirring at 20° C. Stirring was continued at 20° C. for one hour after dropping finished and further for 2 hours after elevating the temperature to 40° C. The solvent contained in the reaction liquid was distilled off under reduced pressure, whereby a dark brown highly viscous liquid of 242.5 g was obtained.

Elemental analysis value ($C_{34}H_{61}NO_3$); Calculated value: C: 76.78%, H: 11.56%, N: 2.63%; Measured value : C: 77.29%, H: 12.05%, N: 2.80%.

Observed by IR analysis were an absorption band originating in carboxylic acid (C=O stretching) in 1710 $cm^{-1}$ and an absorption band originating in amide (C=O stretching) in 1650 $cm^{-1}$.

The structure of L-$C_{24}$-BSA-DA was confirmed by measuring a $^1$H-NMR spectrum and a $^{13}$C-NMR spectrum.

L-$C_{24}$-BSA-DA obtained above was dissolved in water in the form of a carboxylic acid salt, and an aqueous solution (pH 8.99) prepared by adding a 40% sodium hydroxide aqueous solution of 7.9 g and distilled water of 352.1 g to L-$C_{24}$-BSA-DA of 40.0 g and dissolving them homogeneously was used in the following examples.

B-$C_{16}$-ESA-AL

Reference Example 1

A four neck separable flask of 300 ml equipped with a stirrer, a ref lux condenser, a thermometer and a dropping funnel was charged with B-$C_{16}$-ESA ($C_{16}$ type, Colopearl Z-100 manufactured By Seiko Chemical Industries Co., Ltd.) of 100.0 g, and a mixed solution of allyl alcohol of 18.0 g and sulfuric acid of 0.31 g was added dropwise thereto through the dropping funnel in 30 minutes while stirring. The reaction temperature was controlled to 40° C. by a water bath during dropping, and stirring was further continued at 40° C. for 3 hours after dropping was finished, whereby an amber viscous liquid of 118.3 g was obtained. While B-$C_6$-ESA had a viscosity of 96 cp before the reaction, the reaction product (B-$C_{16}$-ESA-AL) had a viscosity of 197 cp.

Elemental analysis value ($C_{23}H_{40}O_4$); Calculated value: C: 72.59%, H: 10.59%; Measured value: C: 72.26%, H: 10.97%.

Figure 7:
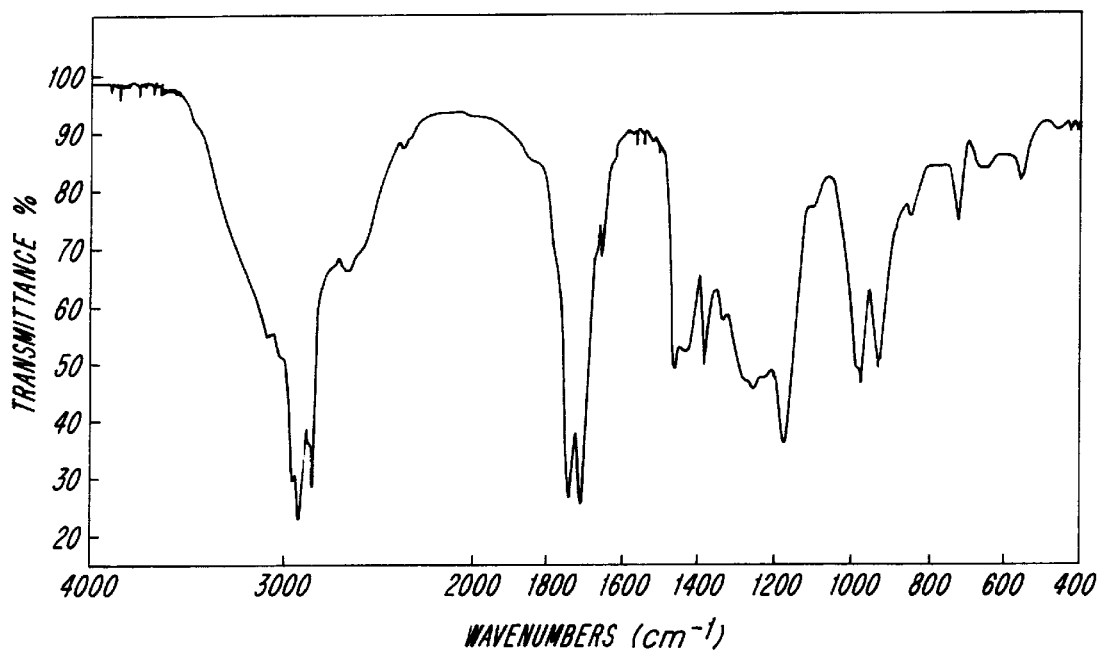
FIG. 7 is an IR absorption spectrum of the compound obtained in Reference Example 1.

IR analysis (FIG. 7) was carried out to find that the characteristic absorption bands (C=O stretching) of the acid anhydride groups in the raw material B-$C_{16}$-ESA observed in 1780 $cm^{-1}$ and 1860 $cm^{-1}$ disappeared and that instead of them, there were observed an absorption band originating in carboxylic acid (C=O stretching) in 1700 $cm^{-1}$ and an absorption band originating in ester (C=O stretching) in 1740 $cm^{-1}$.

Figure 8:
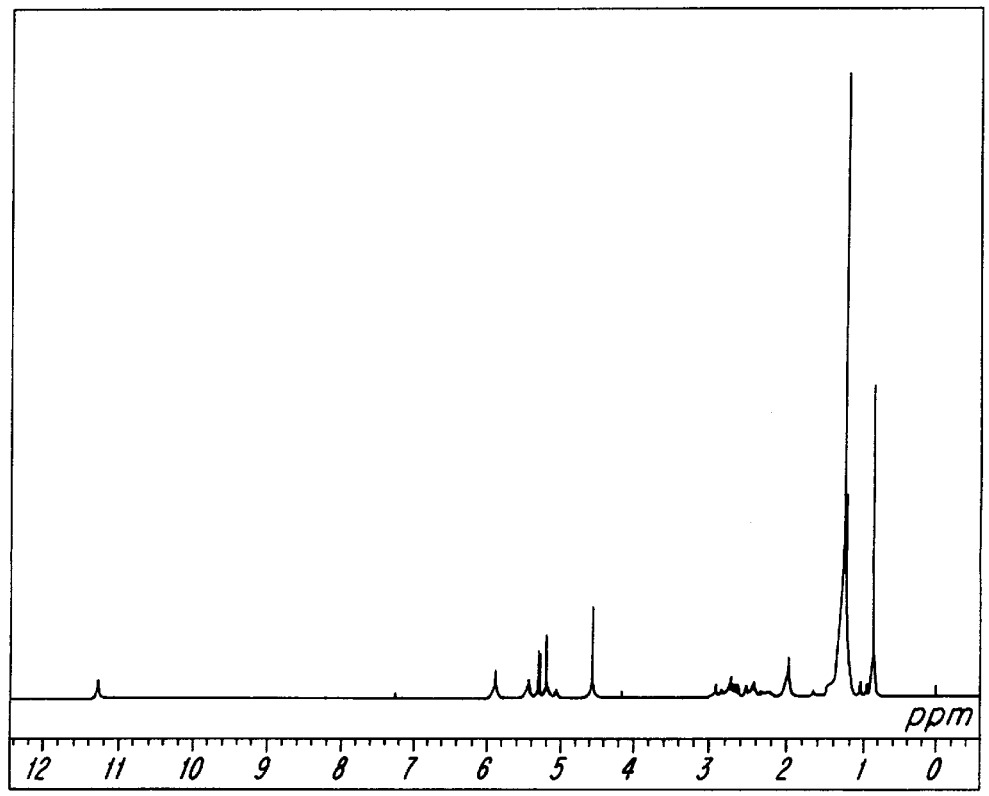
FIG. 8 is a $^1$H-NMR spectrum of the compound obtained in Reference Example 1.
Figure 9:
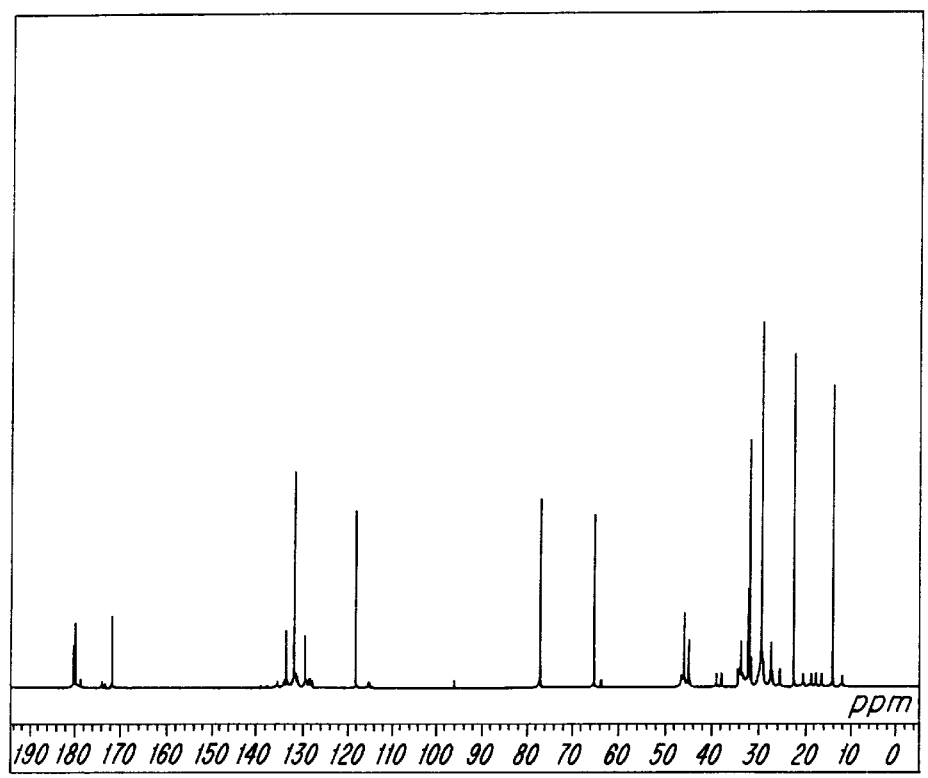
FIG. 9 is a $^{13}$C-NMR spectrum of the compound obtained in Reference Example 1.

A $^1$H-NMR spectrum and a $^{13}$C-NMR spectrum of B-$C_{16}$-ESA-AL were shown in FIG. 8 and FIG. 9. The strength of a magnetic field in the axis of abscissas is shown by ppm unit on the basis (0 ppm) of tetramethylsilane. Used for the assignment of these NMR signals were various NMR determining methods such as DEPT (Distortionless Enhancement by Polarization Transfer), $^1$H-COSY (Correlation Spectroscopy), and C-H correlation COSY.

$^1$H-NMR (CDCl$_{13}$): δ 0.88 (t, 6H, CH$_3$ of R$_1$ and R$_2$); 1.26 (m, 20H, CH$_2$ of R$_1$ and R$_2$); 1.99 (m, 2H, C*HCH=CHC$\underline{H}_2$CH$_2$); 2.25 & 2.32 (m, 1H, C* $\underline{H}$CH=CH), 2.40–2.78 (dd, 2H, COC*HC$\underline{H}_2$CO); 2.83 & 2.94 (m, 1H, COC*$\underline{H}$CH$_2$CO); 4.57 (t, 2H, OC $\underline{H}_2$CH=CH$_2$); 5.04–5.19 (m, 1H, C*HC$\underline{H}$=CH); 5.21–5.32 (m, 2H, OCH$_2$CH=C$\underline{H}_2$); 5.44 (m, 1H, C*HCH=C$\underline{H}$), 5.85–5.93 (m, 1H, OCH$_2$C$\underline{H}$=CH$_2$); 11.27 (s, 1H, COOH).

$^{13}$C-NMR (CDCl$_3$): δ 14.1 (q, 2CH$_3$); 22.7 (t, CH$_3$ $\underline{C}$H$_2$CH$_2$); 29.1–29.7 (m, CH$_2$ of R$_1$ and R$_2$); 32.0 (t, CH$_3$CH$_2$$\underline{C}$H$_2$); 32.6 (t, C*HCH=CH$\underline{C}$H$_2$); 33.2–33.8 (t, COC*H$\underline{C}$H$_2$CO); 44.6 & 44.8 (d, $\underline{C}$*HCH=CH); 45.7 & 46.0 (d, CO$\underline{C}$*HCH$_2$CO); 65.4 (t, O$\underline{C}$H$_2$CH=CH$_2$); 118.3 (t, OCH$_2$CH=$\underline{C}$H$_2$); 129.6 (d, C*H$\underline{C}$H=CH); 132.0 (d, OCH$_2$$\underline{C}$H=CH$_2$); 133.7 & 134.1 (d, C*HCH=$\underline{C}$H); 171.9 & 172.0 (s, COC*HCH$_2$$\underline{C}$O); 180.1 & 180.7 (s, $\underline{C}$OC*HCH$_2$CO). Provided that C* represents an asymmetrical carbon.

B-$C_{16}$-ESA-AL obtained above was dissolved in water in the form of a carboxylic acid salt, and an aqueous solution (pH 9.13) prepared by dissolving homogeneously B-$C_{16}$-ESA-AL of 40.0 g, a 40% sodium hydroxide aqueous solution of 11.4 g, and distilled water of 348.6 g was used in the following examples.

B-$C_{18}$-ESA-AL

Reference Example 2

A four neck separable flask of 1 l equipped with a stirrer, a reflux condenser, a thermometer and a dropping funnel was charged with B-$C_{18}$-ESA ($C_{18}$ type, Pabelas NP manufactured By Mitsubishi Oil Co., Ltd.) of 500.0 g, and a mixed solution of allyl alcohol of 82.8 g and sulfuric acid of 1.84 g was added dropwise thereto through the dropping funnel in 15 minutes while stirring. The reaction temperature was controlled to 40° C. by a water bath during dropping, and stirring was further continued at 40° C. for 5 hours after dropping was finished, whereby a reddish brown, transparent viscous liquid was obtained. While B-$C_{18}$-ESA had a viscosity of 185 cp before the reaction, the reaction product (B-$C_{18}$-ESA-AL) had a viscosity of 275 cp.

Elemental analysis value ($C_{25}H_{44}O_4$); Calculated value: C: 73.48%, H: 10.85%; Measured value: C: 72.72%, H: 11.12%;

The structure of B-$C_{18}$-ESA-AL was confirmed by measuring an IR spectrum, a $^1$H-NMR spectrum and a $^{13}$C-NMR spectrum.

B-$C_{18}$-ESA-AL obtained above was dissolved in water in the form of a carboxylic acid salt, and an aqueous solution (pH 9.13) prepared by dissolving homogeneously B-$C_{18}$-ESA-AL of 40.0 g, a 40% sodium hydroxide aqueous solution of 12.2 g and distilled water of 347.8 g was used in the following examples.

L-$C_{12}$-PSA-AL

Reference Example 3

A four neck separable flask of 300 ml equipped with a stirrer, a reflux condenser, a thermometer and a dropping funnel was charged with L-$C_{12}$-PSA ($C_{12}$ type, MSP manufactured By Mitsubishi Oil Co., Ltd.) of 100.0 g, and a mixed solution of allyl alcohol of 21.8 g and sulfuric acid of 0.37 g was added dropwise thereto through the dropping funnel in 30 minutes while stirring. The reaction temperature was controlled to 40° C. by a water bath during dropping, and stirring was further continued at 40° C. for 3 hours after dropping was finished, whereby an amber highly viscous liquid of 122.1 g was obtained. While L-$C_{12}$-PSA had a viscosity of 370 cp before the reaction, the reaction product (L-$C_{12}$-PSA-AL) had a viscosity of 1,020 cp.

Elemental analysis value ($C_{19}H_{32}O_4$); Calculated value: C: 70.33 %, H: 9.94%; Measured value: C: 69.95%, H: 10.31%.

The structure of L-$C_{12}$-PSA-AL was confirmed by measuring an IR spectrum, a $^1$H-NMR spectrum and a $^{13}$C-NMR spectrum.

L-$C_{12}$-PSA-AL obtained above was dissolved in water in the form of a carboxylic acid salt, and an aqueous solution (pH 8.22) prepared by dissolving homogeneously L-$C_{12}$-PSA-AL of 40.0 g, a 40 % sodium hydroxide aqueous solution of 12.4 g and distilled water of 347.6-g was used in the following examples.

L-$C_{24}$-BSA-AL

Reference Example 4

A four neck separable flask of 300 ml equipped with a stirrer, a reflux condenser, a thermometer and a dropping funnel was charged with L-$C_{24}$-BSA ($C_{24}$ type, LV-7M manufactured By Nippon Petrochemicals Co., Ltd.) of 100.0 g, and a mixed solution of allyl alcohol of 12.9 g and sulfuric acid of 0.22 g was added dropwise thereto through the dropping funnel in 30 minutes while stirring. The reaction temperature was controlled to 40° C. by a water bath during dropping, and stirring was further continued at 40° C. for 4 hours after dropping was finished, whereby an amber highly viscous liquid of 113.1 g was obtained. While L-$C_{24}$-BSA had a viscosity of 4,020 cp before the reaction, the reaction product (L-$C_{24}$-BSA-AL) had a viscosity of 3,070 cp.

Elemental analysis value ($C_{31}H_{56}O_4$); Calculated value: C: 75.56%, H: 11.45%; Measured value: C: 75.47%, H: 12.12%.

The structure of L-$C_{24}$-BSA-AL was confirmed by measuring an IR spectrum, a $^1$H-NMR spectrum and a $^{13}$C-NMR spectrum.

A yellow cloudy aqueous solution (pH 8.73) prepared by mixing L-$C_{24}$-BSA-AL of 40.0 g, a 40 % sodium hydroxide aqueous solution of 7.9 g and distilled water of 352.1 g with stirring was used in the following examples.

B-$C_{16}$-ESA-HM

Example 14

A four neck separable flask of 300 ml equipped with a stirrer, a reflux condenser, a thermometer and a dropping funnel was charged with B-$C_{16}$-ESA ($C_{16}$ type, Colopearl Z-100 manufactured By Seiko Chemical Industries Co., Ltd.) of 100.0 g and sulfuric acid of 0.37 g, and a mixed solution of 2-hydroxyethyl methacrylate (hereinafter abbreviated as HM) of 40.4 g and hydroquinone monomethyl ether of 0.2 g was added dropwise thereto through the dropping funnel in 30 minutes while stirring. The reaction temperature was controlled to 40° C. by a water bath during dropping, and stirring was further continued at 40° C. for 8 hours after dropping was finished, followed by adding triethylamine of 0.73 g to neutralize sulfuric acid, whereby an amber highly viscous liquid of 141.7 g was obtained. While B-$C_{16}$-ESA had a viscosity of 96 cp before the reaction, the reaction product (B-$C_{16}$-ESA-HM) had a viscosity of 552 cp.

Elemental analysis value ($C_{26}H_{44}O_6$); Calculated value: C: 68.99%, H: 9.80%; Measured value: C: 68.65%, H: 10.02%.

Figure 10:
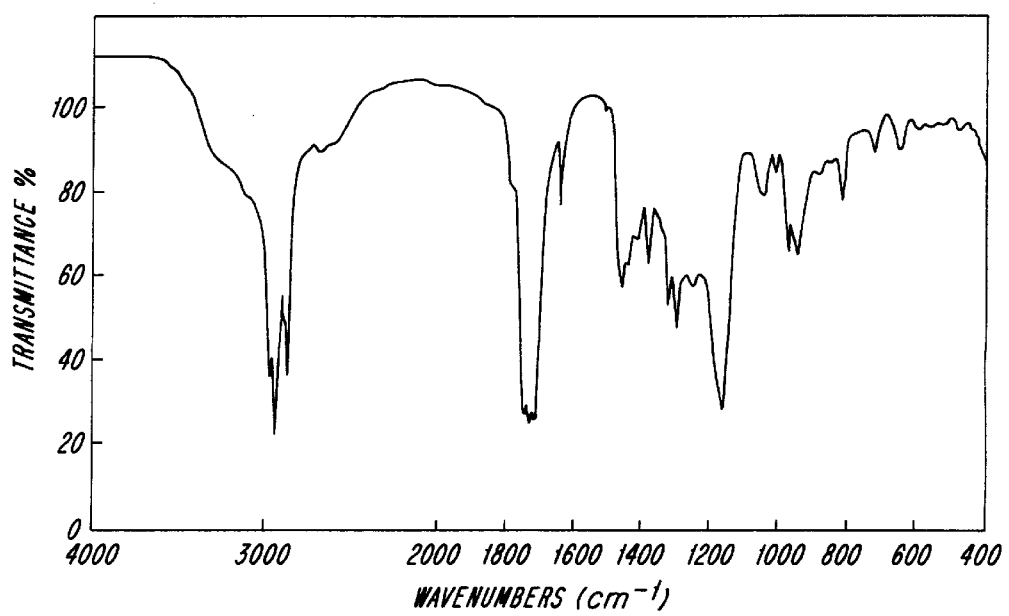
FIG. 10 is an IR absorption spectrum of the compound obtained in Example 14.

IR analysis (FIG. 10) was carried out to find that the characteristic absorption bands (C=O stretching) of an acid anhydride group in the raw material B-$C_{16}$-ESA observed in 1780 $cm^{-1}$ and 1860 $cm^{31\ 1}$ disappeared and that instead of them, there were observed an absorption band originating in carboxylic acid (C=O stretching) in 1710 $cm^{-1}$ and an absorption band originating in ester (C=O stretching) in 1740 $cm^{-1}$.

Figure 11:
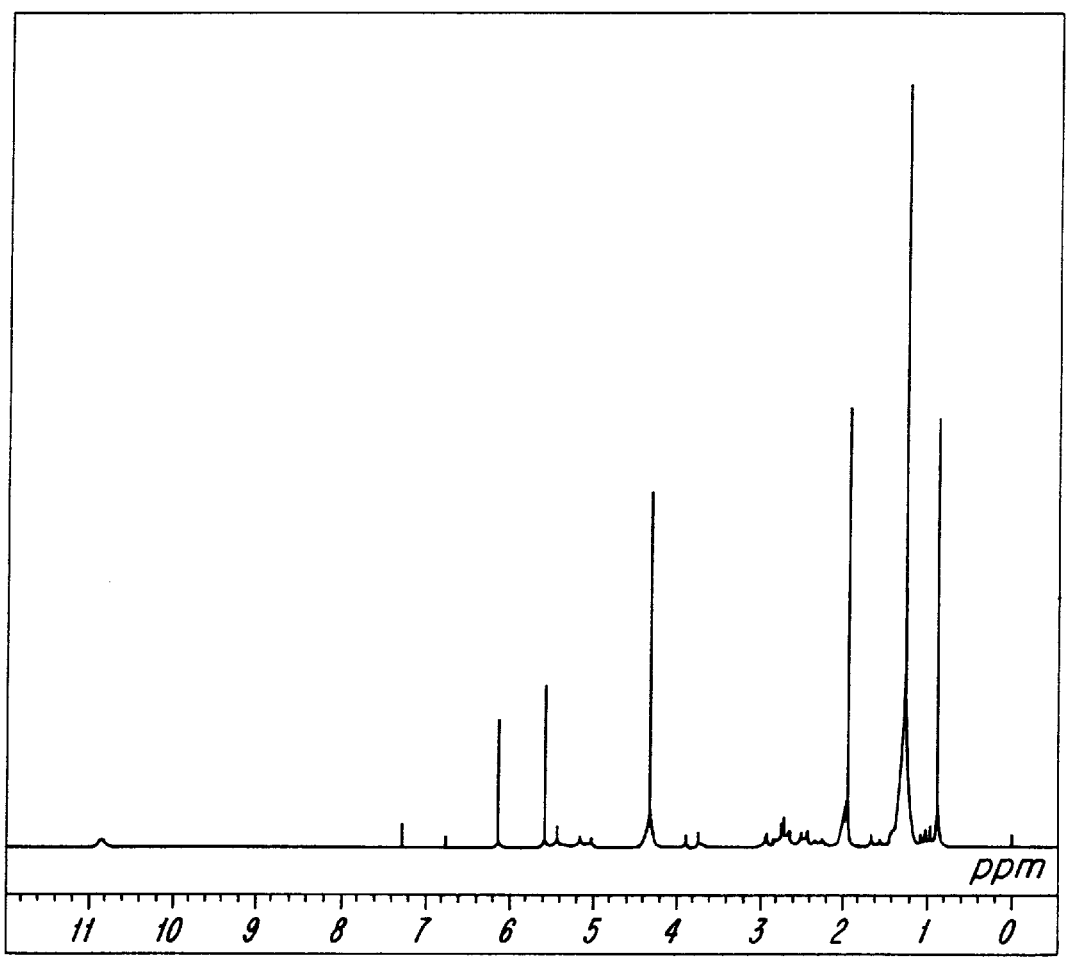
FIG. 11 is a $^1$H-NMR spectrum of the compound obtained in Example 14.
Figure 12:
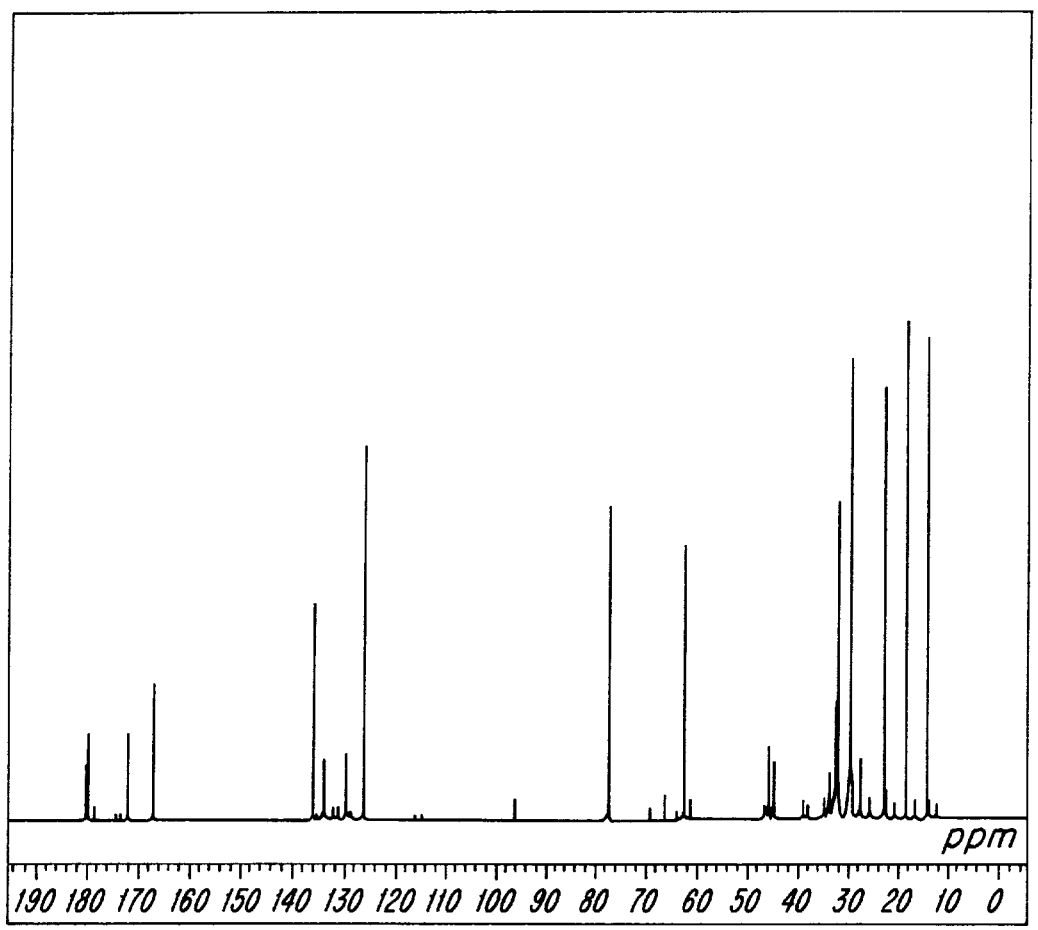
FIG. 12 is a $^{13}$C-NMR spectrum of the compound obtained in Example 14.

A $^1$H-NMR spectrum and a $^{13}$C-NMR spectrum of B-$C_{16}$-ESA-HM were shown in FIG. 11 and FIG. 12. The strength of a magnetic field in the axis of abscissas is shown by ppm unit on the basis (0 ppm) of tetramethylsilane.

An aqueous solution (pH 10.62) prepared by dissolving homogeneously B-$C_{16}$-ESA-HM of 20.0 g, a 40% sodium hydroxide aqueous solution of 4.4 g and distilled water of 175.6 g was used in the following examples.

B-$C_{18}$-ESA-AL-EOA (20)

Example 15

A stainless steel autoclave having a volume of 150 ml was charged with B-$C_{18}$-ESA-AL of 35.0 g (0.086 mole) and potassium hydroxide of 0.56 g as a catalyst and substituted with nitrogen after deaeration under reduced pressure. Then, the reactor was heated, and after the temperature reached 100° C., the pressure was reduced to 50 Torr to carry out dehydration. After finishing the dehydration, nitrogen was introduced into the reactor to an atmospheric pressure, and then EO of 75 g (1.70 mole) was fed into the reactor at a feed rate of 16.2 g/hour to carry out the reaction. During the reaction, the reaction temperature was maintained at 100 to 115° C., and the reaction pressure was maintained at 4.0 to 6.0 kg/$cm^2$. After finishing the reaction, the reaction solution was ripened at 115° C. for one hour. Then, the inner temperature was lowered to 70° C., and acetic acid of 0.59 ml was added as a neutralizing agent, whereby ethoxylate to which EO of 20 moles was added (hereinafter abbreviated as B-$C_{18}$-ESA-AL-EOA (20)) of 110.0 g was obtained.

Elemental analysis value ($C_{65}H_{124}O_{24}$); Calculated value: C: 60.54%, H: 9.69%; Measured value: C: 60.44%, H: 9.67%.

The structure of B-$C_{18}$-ESA-AL-EOA (20) was confirmed by measuring an IR spectrum, a $^1$H-NMR spectrum and a $^{13}$C-NMR spectrum.

B-$C_{18}$-ESA-AL-EOA (15)

Example 16

The reaction was carried out in the same manner as in Example 15, except that there were changed the charge amount of potassium hydroxide to 0.48 g and the feed amount of EO to 57 g (1.30 mole) (a feed rate of 21.3 g/hour) and that the reaction was carried out at reaction temperatures of 100 to 120° C. Further, acetic acid of 0.51 ml was added as a neutralizing agent, whereby ethoxylate to which EO of 15 moles was added (hereinafter abbreviated as B-$C_{18}$-ESA-AL-EOA (15)) of 92.0 g was obtained.

Elemental analysis value ($C_5H_{104}O_9$); Calculated value: C: 61.77%, H: 9.80%; Measured value: C: 59.91%, H: 9.53%.

The structure of B-$C_{18}$-ESA-AL-EOA (15) was confirmed by measuring an IR spectrum, a $^1$H-NMR spectrum and a $^{13}$C-NMR spectrum.

B-$C_{18}$-ESA-AL-EOA (10)

Example 17

The reaction was carried out in the same manner as in Example 15, except that there were changed the charge amount of potassium hydroxide to 0.26 g and the feed amount of EO to 38 g (0.86 mole) (a feed rate of 15.4 g/hour) and that the reaction was carried out at reaction temperatures of 100 to 120° C. Further, acetic acid of 0.41 ml was added as a neutralizing agent, whereby ethoxylate to which EO of 10 moles was added (hereinafter abbreviated as B-$C_{18}$-ESA-AL-EOA (10)) of 73.0 g was obtained.

Elemental analysis value ($C_{45}H_{84}O_{14}$); Calculated value: C: 63.65 %, H: 9.97%; Measured value: C: 62.67%, H: 9.73%.

The structure of B-$C_{18}$-ESA-AL-EOA (10) was confirmed by measuring an IR spectrum, a $^1$H-NMR spectrum and a $^{13}$C-NMR spectrum.

B-$C_{18}$-ESA-AL-EOA (5)

Example 18

The reaction was carried out in the same manner as in Example 15, except that there were changed the charge amount of potassium hydroxide to 0.13 g and the feed amount of EO to 20 g (0.45 mole) (a feed rate of 3.2 g/hour) and that the reaction was carried out at reaction temperatures of 100 to 120° C. Neutralization was not carried out, whereby ethoxylate to which EO of 5 moles was added (hereinafter abbreviated as B-$C_{18}$-ESA-AL-EOA (5)) of 55.0 g was obtained.

Elemental analysis value ($C_{35}H_{64}O_9$); Calculated value: C: 66.85%, H: 10.26%; Measured value: C: 67.30%, H: 10.23%.

The structure of B-$C_{18}$-ESA-AL-EOA (5) was confirmed by measuring an IR spectrum, a $^1$H-NMR spectrum and a $^{13}$C-NMR spectrum.

Example 19

The results of measuring the solubilities and the cloud points of B-$C_{18}$-ESA-AL-EOA (5), (10), (15) and (20) are summarized in Table 1.

TABLE 1

| | Water solubility | | | |
|---|---|---|---|---|
| | pH 5 or less | pH 6 to 8 | pH 9 or more | Cloud point (°C.) |
| B-$C_{18}$-ESA-AL | X | X | ⊚ | — |
| B—$C_{18}$-ESA-AL-EOA (5) | Δ | Δ | Δ | —[1] |
| B—$C_{18}$-ESA-AL-EOA (10) | Δ | Δ | Δ | —[1] |
| B—$C_{18}$-ESA-AL-EOA (15) | ⊚ | ⊚ | ⊚ | 34 |
| B—$C_{18}$-ESA-AL-EOA (20) | ⊚ | ⊚ | ⊚ | 57 |

[1] Cloud point was not observed at 5° C. or higher
[2] Water solubility judgment criteria:
⊚: very excellent
Δ: slightly opaque aqueous solution (dispersion)
X: not dissolved The novel amphipathic compound of the present invention prepared by adding EO to the allyl or vinyl compound having a succinamide structure or a succinic acid ester structure substituted with a hydrophobic group in the skeleton shows good water solubility in a neutral or acid range as well as in an alkaline range. Accordingly, the compound of the present invention can be used as a reactive surfactant. In addition, the polymerization conditions are not restricted when the compound of the present invention is copolymerized with various copolymerizable ethylenically unsaturated compounds, and therefore it can be applied to various fields.

Amphipathic High Molecular Compound (I)

B-$C_{16}$-ESA-MA/PAM

Example 20

A four neck flask of 300 ml equipped with a stirrer, a reflux condenser, a nitrogen introducing tube and a feed tube was charged with a 10% aqueous solution of B-$C_{16}$-ESA-MA obtained in Example 1 of 30.0 g, distilled water of 30.0 g and sodium hypophosphite of 0.15 g, and heated to 80° C. while stirring under nitrogen flow. A mixed solution (cooled by an ice bath) of a 40% acrylamide aqueous solution of 67.5 g, distilled water of 172.1 g, and ammonium persulfate (hereinafter referred to as APS) of 0.30 g was added dropwise to this solution with a microtube pump in 120 minutes. Further, stirring was continued at 80° C. for 180 minutes to obtain a homogeneous pale yellow aqueous solution. The aqueous solution thus obtained had a viscosity of 63.5 cp and a weight-average molecular weight of 221,000.

Example 21

A four neck flask of 300 ml equipped with a stirrer, a reflux condenser, a nitrogen-introducing tube and a feed tube was charged with a 10% aqueous solution of B-$C_{16}$-ESA-MA obtained in Example 1 of 60.0 g and sodium hypophosphite of 0.225 g, and heated to 80° C. while stirring under nitrogen flow. A mixed solution (cooled by an ice bath) of a 40% acrylamide aqueous solution of 60.0 g, distilled water of 179.5 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 107.0 cp and a weight-average molecular weight of 125,000.

B-$C_{16}$-ESA-DA/PAM

Example 22

A four neck flask of 300 ml equipped with a stirrer, a reflux condenser, a nitrogen introducing tube and a feed tube was charged with a 10 t aqueous solution of B-$C_{16}$-ESA-DA obtained in Example 2 of 30.0 g, distilled water of 30.0 g and sodium hypophosphite of 0.225 g, and heated to 80° C. while stirring under nitrogen flow. A mixed solution (cooled by an ice bath) of a 40% acrylamide aqueous solution of 67.5 g, distilled water of 172.0 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 15.3 cp and a weight-average molecular weight of 152,000.

Example 23

A four neck flask of 300 ml equipped with a stirrer, a reflux condenser, a nitrogen introducing tube and a feed tube was charged with a 10 % aqueous solution of B-$C_{16}$-ESA-DA obtained in Example 2 of 60.0 g and sodium hypophosphite of 0.30 g, and heated to 80° C. while stirring under nitrogen flow. A mixed solution (cooled on an ice bath) of a 40% acrylamide aqueous solution of 60.0 g, distilled water of 179.4 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 56.9 cp and a weight-average molecular weight of 174,000.

L-$C_{12}$-PSA-MA/PAM

Example 24

A four neck flask of 300 ml equipped with a stirrer, a reflux condenser, a nitrogen introducing tube and a feed tube was charged with a 10% aqueous solution of L-$C_{12}$-PSA-MA obtained in Example 10 of 60.0 g and sodium hypophosphite of 0.60 g, and heated to 80° C. while stirring under nitrogen flow. A mixed solution (cooled by an ice bath) of a 40% acrylamide aqueous solution of 135.0 g, distilled water of 103.8 g, and APS of 0.60 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 21.6%, a pH of 6.96, a viscosity of 697 cp and a weight-average molecular weight of 47,000.

Example 25

A four neck flask of 300 ml equipped with a stirrer, a reflux condenser, a nitrogen introducing tube and a feed tube was charged with a 10% aqueous solution of L-$C_{12}$-PSA-MA obtained in Example 10 of 120.0 g and sodium hypophosphite of 0.90 g, and heated to 80° C. while stirring under nitrogen flow. A mixed solution (cooled by an ice bath) of a 40% acrylamide aqueous solution of 120.0 g, distilled water of 58.2 g, and APS of 0.90 g was added dropwise to this solution with the microtube pump in 120 minutes. Further, stirring was continued at 80° C. for 180 minutes to obtain a homogeneous aqueous solution which was colored to thin yellow. The aqueous solution thus obtained had a non-volatile content of 21.4%, a pH of 7.30, a viscosity of 853 cp and a weight-average molecular weight of 9,100.

Example 26

A four neck flask of 300 ml equipped with a stirrer, a reflux condenser, a nitrogen introducing tube and a feed tube was charged with a 10% aqueous solution of L-$C_{12}$-PSA- MA obtained in Example 10 of 180.0 g and sodium hypophosphite of 1.20 g, and heated to 80° C. while stirring under nitrogen flow. A mixed solution (cooled by an ice bath) of a 40% acrylamide aqueous solution of 105.0 g, distilled water of 12.6 g, and APS of 1.20 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 21.4%, a pH of 7.38, a viscosity of 571 cp and a weight-average molecular weight of 5,000.

L-$C_{12}$-PSA-DA/PAM

Example 27

A four neck flask of 300 ml equipped with a stirrer, a reflux condenser, a nitrogen introducing tube and a feed tube was charged with a 10% aqueous solution of L-$C_{12}$-PSA-DA obtained in Example 11 of 30.0 g, distilled water of 89.7 g and sodium hypophosphite of 0.30 g, and heated to 80° C. while stirring under nitrogen flow. A mixed solution (cooled by an ice bath) of a 50% acrylamide aqueous solution of 54.0 g, distilled water of 125.7 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.8%, a pH of 6.43, a viscosity of 11.1 cp and a weight-average molecular weight of 25,000.

Example 28

A four neck flask of 300 ml equipped with a stirrer, a reflux condenser, a nitrogen introducing tube and a feed tube was charged with a 10% aqueous solution of L-$C_{12}$-PSA-DA obtained in Example 11 of 60.0 g, distilled water of 59.4 g and sodium hypophosphite of 0.60 g, and heated to 80° C. while stirring under nitrogen flow. A mixed solution (cooled by an ice bath) of a 50% acrylamide aqueous solution of 54.0 g, distilled water of 125.7 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 11.9%, a pH of 7.01, a viscosity of 6.9 cp and a weight-average molecular weight of 13,800.

Example 29

A four neck flask of 300 ml equipped with a stirrer, a reflux condenser, a nitrogen introducing tube and a feed tube was charged with a 10 % aqueous solution of L-$C_{12}$-PSA-DA obtained in Example 11 of 90.0 g, distilled water of 29.1 g and sodium hypophosphite of 0.90 g, and heated to 80° C. while stirring under nitrogen flow. A mixed solution (cooled by an ice bath) of a 50% acrylamide aqueous solution of 54.0 g, distilled water of 125.7 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 13.0%, a pH of 7.28, a viscosity of 6.3 cp and a weight-average molecular weight of 9,400.

L-$C_{24}$-BSA-MA/PAM

Example 30

A four neck flask of 300 ml equipped with a stirrer, a reflux condenser, a nitrogen introducing tube and a feed tube was charged with a 10% aqueous solution of L-$C_{24}$-BSA-MA obtained in Example 12 of 30.0 g, distilled water of 29.7 g and sodium hypophosphite of 0.30 g, and heated to 80° C. while stirring under nitrogen flow. A mixed solution (cooled by an ice bath) of a 50% acrylamide aqueous solution of 54.0 g, distilled water of 185.7 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.5%, a pH of 7.19, a viscosity of 8.4 cp and a weight-average molecular weight of 30,300.

Example 31

A four neck flask of 300 ml equipped with a stirrer, a reflux condenser, a nitrogen introducing tube and a feed tube was charged with a 10 % aqueous solution of L-$C_{24}$-BSA-MA obtained in Example 12 of 60.0 g and sodium hypophosphite of 0.60 g, and heated to 80° C. while stirring under nitrogen flow. A mixed solution (cooled by an ice bath) of a 50% acrylamide aqueous solution of 48.0 g, distilled water of 191.1 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.7% a pH of 7.72, a viscosity of 5.3 cp and a weight-average molecular weight of 35,000.

Example 32

A four neck flask of 300 ml equipped with a stirrer, a reflux condenser, a nitrogen introducing tube and a feed tube was charged with a 10% aqueous solution of L-$C_{24}$-BSA-MA obtained in Example 12 of 90.0 g and sodium hypophosphite of 0.90 g, and heated to 80° C. while stirring under nitrogen flow. A mixed solution (cooled by an ice bath) of a 50% acrylamide aqueous solution of 42.0 g, distilled water of 166.8 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.8%, a pH of 7.91, a viscosity of 3.7 cp and a weight-average molecular weight of 30,400.

L-$C_{24}$-BSA-DA/PAM

Example 33

A four neck flask of 300 ml equipped with a stirrer, a reflux condenser, a nitrogen introducing tube and a feed tube was charged with a 10% aqueous solution of L-$C_{24}$-BSA-DA obtained in Example 13 of 30.0 g, distilled water of 29.7 g, and sodium hypophosphite of 0.30 g, and heated to 80° C. while stirring under nitrogen flow. A mixed solution (cooled by an ice bath) of a 50% acrylamide aqueous solution of 54.0 g, distilled water of 185.7 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.7%, a pH of 7.06, a viscosity of 7.28 cp and a weight-average molecular weight of 29,000.

Example 34

A four neck flask of 300 ml equipped with a stirrer, a reflux condenser, a nitrogen introducing tube and a feed tube was charged with a 10% aqueous solution of L-C$_{24}$-BSA-DA obtained in Example 13 of 60.0 g and sodium hypophosphite of 0.60 g, and heated to 80° C. while stirring under nitrogen flow. A mixed solution (cooled by an ice bath) of a 50% acrylamide aqueous solution of 48.0 g, distilled water of 191.1 g, and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.6%, a pH of 7.50, a viscosity of 5.0 cp and a weight-average molecular weight of 49,600.

Example 35

A four neck flask of 300 ml equipped with a stirrer, a reflux condenser, a nitrogen introducing tube and a feed tube was charged with a 10% aqueous solution of L-C$_{24}$-BSA-DA obtained in Example 13 of 90.0 g and sodium hypophosphite of 0.90 g, and heated to 80° C. while stirring under nitrogen flow. A mixed solution (cooled by an ice bath) of a 50% acrylamide aqueous solution of 42.0 g, distilled water of 166.8 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.8%, a pH of 7.76, a viscosity of 4.4 cp and a weight-average molecular weight of 29,500.

B-C$_{16}$-ESA-AL/PAM

Example 36

A four neck flask of 300 ml equipped with a stirrer, a reflux condenser, a nitrogen introducing tube and a feed tube was charged with a 10% aqueous solution of B-C$_{16}$-ESA-AL obtained in Reference Example 1 of 30.0 g, distilled water of 29.9 g and sodium hypophosphite of 0.15 g, and heated to 80° C. while stirring under nitrogen flow. A mixed solution (cooled by an ice bath) of a 50% acrylamide aqueous solution of 54.0 g, distilled water of 185.7 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 478 cp and a weight-average molecular weight of 215,700.

Example 37

A four neck flask of 300 ml equipped with a stirrer, a reflux condenser, a nitrogen-introducing tube and a feed tube was charged with a 10% aqueous solution of B-C$_{16}$-ESA-AL obtained in Reference Example 1 of 60.0 g and sodium hypophosphite of 0.225 g, and heated to 80° C. while stirring under nitrogen flow. A mixed solution (cooled by an ice ice bath) of a 50% acrylamide aqueous solution of 48.0 g, distilled water of 191.5 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 8,190 cp and a weight-average molecular weight of 152,100.

Example 38

A four neck flask of 300 ml equipped with a stirrer, a reflux condenser, a nitrogen introducing tube and a feed tube was charged with a 10% aqueous solution of B-C$_{16}$-ESA-AL obtained in Reference Example 1 of 90.0 g and sodium hypophosphite of 0.45 g, and heated to 80° C. while stirring under nitrogen flow. A mixed solution (cooled by an ice ice bath) of a 50% acrylamide aqueous solution of 42.0 g, distilled water of 167.3 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a viscosity of 16.2 cp and a weight-average molecular weight of 30,400.

L-C$_{12}$-PSA-AL/PAM

Example 39

A four neck flask of 300 ml equipped with a stirrer, a reflux condenser, a nitrogen introducing tube and a feed tube was charged with a 10% aqueous solution of L-C$_{12}$-PSA-AL obtained in Reference Example 3 of 30.0 g, distilled water of 29.9 g and sodium hypophosphite of 0.15 g, and heated to 80° C. while stirring under nitrogen flow. A mixed solution (cooled by an ice ice bath) of a 50% acrylamide aqueous solution of 54.0 g, distilled water of 185.7 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.6%, a pH of 7.10, a viscosity of 166 cp and a weight-average molecular weight of 32,000.

Example 40

A four neck flask of 300 ml equipped with a stirrer, a reflux condenser, a nitrogen introducing tube and a feed tube was charged with a 10% aqueous solution of L-C$_{12}$-PSA-AL obtained in Reference Example 3 of 60.0 g and sodium hypophosphite of 0.30 g, and heated to 80° C. while stirring under nitrogen flow. A mixed solution (cooled by an ice ice bath) of a 50° C. acrylamide aqueous solution of 48.0 g, distilled water of 191.4 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.7%, a pH of 7.42, a viscosity of 51.0 cp and a weight-average molecular weight of 12,300.

Example 41

A four neck flask of 300 ml equipped with a stirrer, a reflux condenser, a nitrogen introducing tube and a feed tube was charged with a 10% aqueous solution of L-C$_{12}$-PSA-AL obtained in Reference Example 3 of 90.0 g and sodium hypophosphite of 0.38 g, and heated to 80° C. while stirring under nitrogen flow. A mixed solution (cooled by an ice ice bath) of a 50% acrylamide aqueous solution of 42.0 g, distilled water of 167.3 g and APS of 0.30 g was added dropwise to this solution with the microtube pump in 120 minutes. Further, stirring was continued at 80° C. for 180 minutes to obtain a homogeneous pale yellow aqueous solution. The aqueous solution thus obtained had a non-volatile content of 10.8%, a pH of 7.49, a viscosity of 60.2 cp and a weight-average molecular weight of 7,700.

L-C$_{24}$-BSA-AL/PAM

Example 42

A four neck flask of 300 ml equipped with a stirrer, a reflux condenser, a nitrogen introducing tube and a feed tube was charged with a 10% aqueous solution of L-C$_{24}$-BSA-AL obtained in Reference Example 4 of 30.0 g, distilled water of 29.9 g and sodium hypophosphite of 0.15 g, and heated to 80° C. while stirring under nitrogen flow. A mixed solution (cooled by an ice ice bath) of a 50% acrylamide aqueous solution of 54.0 g, distilled water of 185.7 g and APS of 0.30 g was added dropwise to this solution with the microtube pump in 120 minutes. Further, stirring was continued at 80° C. for 180 minutes to obtain an aqueous solution which was colored to pale yellow and slightly turbid. The aqueous solution thus obtained had a non-volatile content of 10.7%, a pH of 6.90, a viscosity of 17.3 cp and a weight-average molecular weight of 152,700.

Example 43

A four neck flask of 300 ml equipped with a stirrer, a reflux condenser, a nitrogen introducing tube and a feed tube was charged with a 10% aqueous solution of L-$C_{24}$-BSA-AL obtained in Reference Example 4 of 60.0 g and sodium hypophosphite of 0.30 g, and heated to 80° C. while stirring under nitrogen flow. A mixed solution (cooled by an ice ice bath) of a 50% acrylamide aqueous solution of 48.0 g, distilled water of 191.4 g and APS of 0.30 g was added dropwise to this solution with the microtube pump in 120 minutes. Further, stirring was continued at 80° C. for 180 minutes to obtain an aqueous solution which was colored to pale yellow and slightly turbid. The aqueous solution thus obtained had a non-volatile content of 10.7%, a pH of 7.32, a viscosity of 7.7 cp and a weight-average molecular weight of 163,500.

Example 44

A four neck flask of 300 ml equipped with a stirrer, a reflux condenser, a nitrogen introducing tube and a feed tube was charged with a 10% aqueous solution of L-$C_{24}$-BSA-AL obtained in Reference Example 4 of 90.0 g and sodium hypophosphite of 0.38 g, and heated to 80° C. while stirring under nitrogen flow. A mixed solution (cooled by an ice ice bath) of a 50% acrylamide aqueous solution of 42.0 g, distilled water of 167.3 g and APS of 0.30 g was added dropwise to this solution with the microtube pump in 120 minutes. Further, stirring was continued at 80° C. for 180 minutes to obtain a homogeneous aqueous solution which was colored to pale yellow and slightly turbid. The aqueous solution thus obtained had a non-volatile content of 10.8%, a pH of 7.58, a viscosity of 7.1 cp and a weight-average molecular weight of 34,900.

B-$C_{16}$-ESA-HM/PAM

Example 45

A four neck flask of 300 ml equipped with a stirrer, a reflux condenser, a nitrogen introducing tube and a feed tube was charged with a 10% aqueous solution of B-$C_{16}$-ESA-HM obtained in Example 14 of 15.0 g, a 50% acrylamide aqueous solution of 57.0 g, distilled water of 221.4 g, sodium hydrogensulfite of 0.30 g and sodium hypophosphite of 0.30 g, and heated to 30° C. while stirring under nitrogen flow. A 10% APS aqueous solution of 6.0 g was added to this solution. After continuing stirring at 30° C. for 180 minutes, a 10% APS aqueous solution and a 10% sodium hydrogensulfite aqueous solution of each 0.9 g were added, and stirring was further continued for 120 minutes to obtain an aqueous solution which was slightly opaque. The aqueous solution thus obtained had a non-volatile content of 10.8%, a pH of 8.43, a viscosity of 176.2 cp and a weight-average molecular weight of 418,600.

Example 46

A four neck flask of 300 ml equipped with a stirrer, a reflux condenser, a nitrogen introducing tube and a feed tube was charged with a 10% aqueous solution of B-$C_{16}$-ESA-HM obtained in Example 14 of 30.0 g, a 50% acrylamide aqueous solution of 54.0 g, distilled water of 209.1 g, sodium hydrogensulfite of 0.30 g and sodium hypophosphite of 0.60 g, and heated to 30° C. while stirring under nitrogen flow. A 10% APS aqueous solution of 6.0 g was added to this solution. After continuing stirring at 30° C. for 180 minutes, a 10% APS aqueous solution and a 10% sodium hydrogensulfite aqueous solution of each 0.9 g were added, and stirring was further continued for 120 minutes to obtain an aqueous solution which was slightly opaque. The aqueous solution thus obtained had a non-volatile content of 10.9%, a pH of 8.64, a viscosity of 448.0 cp and a weight-average molecular weight of 186,100.

Example 47

A four neck flask of 300 ml equipped with a stirrer, a reflux condenser, a nitrogen introducing tube and a feed tube was charged with a 10% aqueous solution of B-$C_{16}$-ESA-HM obtained in Example 14 of 45.0 g, a 50% acrylamide aqueous solution of 51.0 g, distilled water of 196.2 g, sodium hydrogensulfite of 0.30 g and sodium hypophosphite of 1.50 g, and heated to 30° C. while stirring under nitrogen flow. A 10% APS aqueous solution of 6.0 g was added to this solution. After continuing stirring at 30° C. for 180 minutes, a 10% APS aqueous solution and a 10% sodium hydrogensulfite aqueous solution of each 0.9 g was added, and stirring was further continued for 120 minutes to obtain an aqueous solution which were slightly opaque. The aqueous solution thus obtained had a non-volatile content of 11.1%, a pH of 8.78, a viscosity of 65.9 cp and a weight-average molecular weight of 85,400.

Comparative Example 1

A four neck flask of 300 ml equipped with a stirrer, a reflux condenser, a nitrogen introducing tube and a feed tube was charged with distilled water of 60.0 g and sodium hypophosphite of 0.05 g, and heated to 80° C. while stirring under nitrogen flow. A mixed solution (cooled by an ice ice bath) of a 40% acrylamide aqueous solution of 150.0 g, distilled water of 89.7 g and APS of 0.30 g was added dropwise to this solution with the microtube pump in 120 minutes. Further, stirring was continued at 80° C. for 180 minutes to obtain a transparent, homogeneous aqueous solution. The aqueous solution thus obtained had a viscosity of 2,680 cp and a weight-average molecular weight of 189,000.

All the following coating examples and coating comparative examples were carried out using a base paper (basis weight 50 g/m$^2$) for newspaper. A sizing degree was determined according to a Stockigt sizing test method of JIS P8122; a surface strength was determined by measuring an RI pick with model RI-3 (Akira Mfg. Co., Ltd.) (relative evaluation by a ten point system; the higher the point, the higher the surface strength); and a Z axis strength was determined with an internal bond tester (Kumagaya Riki Ind. Co., Ltd.).

Coating Examples 1 to 16

Base papers for coating were immersed in the polymer solutions obtained in Examples 20 to 35 for one second and squeezed between two rolls. Then, the amounts of the solution absorbed were weighed to determine the coated amounts. The concentrations of the coating solutions were adjusted in advance so that the coated amounts in terms of non-volatile matters of the polymer were 1.0 g/m$^2$ in the case of Coating Examples 1 to 4, 0.8 g/m$^2$ in the case of Coating Examples 5 to 10 and 1.2 g/m$^2$ in the case of Coating Examples 11 to 16. The pH values of the coating solutions were adjusted to 7.8 to 8.2. Immediately after coating, the coated paper was dried for 50 seconds in a drum drier in which the surface temperature was set at 120° C., and after subjecting the dried paper to humidity conditioning for 24 hours in a constant temperature and humidity chamber (20° C., humidity 65%), the sizing degrees and the paper strength were determined. The results thereof are shown in Table 2.

Coating Examples 17 to 19

The polymer solutions obtained in Examples 45 to 47 were used to carry out the coating test in the same manner as in Coating Examples 1 to 16. The concentrations of the coating solutions were adjusted in advance so that the coated amount in terms of non-volatile matters of the polymer was 1.0 g/m². The results thereof are shown in Table 2.

Coating Examples 20 to 34

Coated papers were prepared in the same manner as in Coating Examples 1 to 16 to determine the sizing degrees and the paper strength, except that the pH in coating was changed to 3.0 to 5.0. There were used the polymer solutions obtained in Examples 20 to 23 for Coating Examples 20 to 23 and those obtained in Examples 36 to 44 for Coating Examples 24 to 32. The concentrations of the coating solutions were adjusted in advance so that the coated amount in terms of non-volatile matters of the polymer was 1.0 g/m². The results thereof are shown in Table 3. On the pH condition of the present coating examples, ASA-MA, ASA-AL and ASA-HM decreased in solubility in water to turn into emulsions, but the polymers prepared by copolymerizing with acrylamide were transparent viscous aqueous solutions.

TABLE 2

Coating Test Result

| Coating Example | | Polymerization rate wt % | Coated amount g/m² | Coating solution pH | Steckigt sizing degree (sec.) | RI pick | Z axis strength kg-cm |
|---|---|---|---|---|---|---|---|
| Blank | — | — | — | 6.90 | 1.0 | 4.5 | 1.09 |
| 1 (Inv.) | B-$C_{16}$-ESA-MA | 10 | 1.0 | 7.81 | 32.6 | 9.0 | 1.78 |
| 2 (Inv.) | B-$C_{16}$-ESA-MA | 20 | 1.0 | 8.21 | 37.2 | 8.0 | 1.62 |
| 3 (Inv.) | B-$C_{16}$-ESA-DA | 10 | 1.0 | 7.85 | 33.5 | 8.5 | 1.71 |
| 4 (Inv.) | B-$C_{16}$-ESA-DA | 20 | 1.0 | 8.10 | 34.1 | 8.0 | 1.63 |
| 5 (Inv.) | L-$C_{12}$-PSA-MA | 10 | 0.8 | 8.02 | 24.7 | 8.5 | 1.74 |
| 6 (Inv.) | L-$C_{12}$-PSA-MA | 18 | 0.8 | 8.15 | 27.6 | 8.5 | 1.70 |
| 7 (Inv.) | L-$C_{12}$-PSA-MA | 25 | 0.8 | 8.16 | 28.2 | 8.0 | 1.64 |
| 8 (Inv.) | L-$C_{12}$-PSA-DA | 10 | 0.8 | 7.87 | 25.1 | 8.5 | 1.72 |
| 9 (Inv.) | L-$C_{12}$-PSA-DA | 18 | 0.8 | 7.95 | 27.0 | 8.0 | 1.71 |
| 10 (Inv.) | L-$C_{12}$-PSA-DA | 25 | 0.8 | 8.04 | 25.5 | 8.0 | 1.63 |
| 11 (Inv.) | L-$C_{24}$-BSA-MA | 10 | 1.2 | 7.35 | 29.6 | 9.0 | 1.85 |
| 12 (Inv.) | L-$C_{24}$-BSA-MA | 20 | 1.2 | 7.42 | 34.2 | 8.5 | 1.78 |
| 13 (Inv.) | L-$C_{24}$-BSA-MA | 30 | 1.2 | 7.48 | 32.5 | 8.0 | 1.74 |
| 14 (Inv.) | L-$C_{24}$-BSA-DA | 10 | 1.2 | 7.36 | 27.1 | 8.5 | 1.82 |
| 15 (Inv.) | L-$C_{24}$-BSA-DA | 20 | 1.2 | 7.45 | 29.8 | 8.5 | 1.77 |
| 16 (Inv.) | L-$C_{24}$-BSA-DA | 30 | 1.2 | 7.45 | 28.9 | 8.0 | 1.75 |
| 17 (Inv.) | B-$C_{16}$-ESA-HM | 5 | 1.0 | 7.63 | 25.5 | 8.5 | 1.83 |
| 18 (Inv.) | B-$C_{16}$-ESA-HM | 10 | 1.0 | 7.92 | 26.8 | 8.5 | 1.79 |
| 19 (Inv.) | B-$C_{16}$-ESA-HM | 15 | 1.0 | 7.95 | 26.7 | 8.0 | 1.76 |
| 1 (Comp.) | — | — | 0.8 | 6.85 | 1.5 | 8.0 | 1.63 |
| | — | — | 1.0 | 6.85 | 1.5 | 8.0 | 1.63 |
| | — | — | 1.2 | 7.35 | 1.2 | 8.0 | 1.73 |

RI pick conditions: Toyo Ink, ink tack 25, ink amount 0.4 ml, 60 rpm

TABLE 3

Coating Test Result

| Coating Example | | Polymerization rate wt % | Coated amount g/m² | Coating solution pH | Steckigt sizing degree (sec.) | RI pick | Z axis strength kg-cm |
|---|---|---|---|---|---|---|---|
| Blank | — | — | — | 4.88 | 1.0 | 4.5 | 1.02 |
| 20 (Inv.) | B-$C_{16}$-ESA-MA | 10 | 1.0 | 3.02 | 30.6 | 8.5 | 1.74 |
| 21 (Inv.) | B-$C_{16}$-ESA-MA | 20 | 1.0 | 4.01 | 32.5 | 8.0 | 1.71 |
| 22 (Inv.) | B-$C_{16}$-ESA-DA | 10 | 1.0 | 3.93 | 30.7 | 8.5 | 1.70 |
| 23 (Inv.) | B-$C_{16}$-ESA-DA | 20 | 1.0 | 3.80 | 32.8 | 8.5 | 1.64 |
| 24 (Inv.) | B-$C_{16}$-ESA-AL | 10 | 1.0 | 4.52 | 29.8 | 8.5 | 1.79 |
| 25 (Inv.) | B-$C_{16}$-ESA-AL | 20 | 1.0 | 4.79 | 30.4 | 8.0 | 1.73 |
| 26 (Inv.) | B-$C_{16}$-ESA-AL | 30 | 1.0 | 4.96 | 27.5 | 8.0 | 1.70 |
| 27 (Inv.) | L-$C_{12}$-PSA-AL | 10 | 1.0 | 4.60 | 26.5 | 8.5 | 1.78 |
| 28 (Inv.) | L-$C_{12}$-PSA-AL | 20 | 1.0 | 4.82 | 29.3 | 8.0 | 1.72 |
| 29 (Inv.) | L-$C_{12}$-PSA-AL | 30 | 1.0 | 4.89 | 27.7 | 8.0 | 1.66 |
| 30 (Inv.) | L-$C_{24}$-BSA-AL | 10 | 1.0 | 4.55 | 25.5 | 8.5 | 1.79 |

TABLE 3-continued

| | | Coating Test Result | | | | | |
|---|---|---|---|---|---|---|---|
| Coating Example | | Polymerization rate wt % | Coated amount g/m$^2$ | Coating solution pH | Steckigt sizing degree (sec.) | RI pick | Z axis strength kg-cm |
| 31 (Inv.) | L-C$_{24}$-BSA-AL | 20 | 1.0 | 4.78 | 31.8 | 8.0 | 1.68 |
| 32 (Inv.) | L-C$_{24}$-BSA-AL | 30 | 1.0 | 4.95 | 30.4 | 8.0 | 1.64 |

RI pick conditions: Toyo Ink, ink tack 25, ink amount 0.4 ml, 60 rpm

Coating Comparative Example 1

A coated paper was prepared in the same manner as in Coating Examples 1 to 16 to determine a sizing degree and a paper strength, except that the polymer was changed to one produced in Comparative Example 1. The results thereof are shown in Table 2.

As apparent from the examples, the amphipathic compound of the present invention used as a copolymerizable component for acrylamide polymers provides compounds which are useful as paper making additives having not only an excellent paper reinforcing performance but also a good sizing performance. The actions thereof are not necessarily clarified, but it is considered that an amide group of the copolymer forms a hydrogen bond with cellulose fiber in a drying step after coating and this improves the paper strength to a large extent and that the alkenyl groups are coagulated to be oriented on the surface of the paper, whereby the sizing performance is exhibited.

Amphipathic High Molecular Compound (III)

The amphipathic compound (III) of the present invention shall be explained in detail but the present invention shall not be restricted to these examples. In the following examples, percentage is based on weight, and viscosity is a value determined with a B type viscometer at 25° C.

Example 48

A 20 wt % aqueous solution of B-C$_{16}$-ESA-MA obtained in Example 1 of 50.0 g, sodium hypophosphite monohydrate of 0.25 g and distilled water of 469.8 g were blended homogeneously in a flask, and then the pH was adjusted to 9.0. After substituting the air in the flask with nitrogen, the mixed solution contained in the flask was heated to 80° C., and then an aqueous solution prepared by blending homogeneously a 50% acrylamide aqueous solution of 161.2 g, DM of 9.4 g, 35% hydrochloric acid of 6.2 g, distilled water of 302.7 g and APS of 0.5 g, and then adjusting the pH to 4.5 with a 10% sodium hydroxide aqueous solution was added through the feed tube with the microtube pump in 120 minutes. One hour after finishing the addition, a 2.5% APS aqueous solution of 10 ml and a 2.5% sodium sulfite (SBS) aqueous solution of 10 ml were added, and stirring was further continued at 80° C. for 2 hours, whereby a bluish white aqueous solution was obtained. The aqueous solution thus obtained had a solid concentration of 10.7%, a viscosity of 20.1 cp and a pH of 6.70.

Examples 49 to 52

The polymerization was carried out in the same manner as in Example 48, except that the compositions were changed as shown in Table 4. The results thereof are shown in Table 4.

Examples 53 to 55

The polymerization was carried out in the same manner as in Examples 48–50 to obtain a transparent viscous liquid, except that the amounts of sodium hypophosphite (chain transfer agent) and APS (polymerization initiator) are changed as shown in Table 4. The results are shown in Table 4.

Example 56

A four neck flask of 1 l equipped with a stirrer, a reflux condenser, a nitrogen introducing tube and a feed tube was charged with a 80 wt % aqueous solution of B-C$_{18}$-ESA-MA produced in Example 3 of 25.0 g, sodium hypophosphite monohydrate of 0.75 g and distilled water of 494.3 g to blend them homogeneously, and then the pH was adjusted to 9.0. After substituting the air in the flask with nitrogen, the mixed solution contained in the flask was heated to 80° C., and then an aqueous solution prepared by blending homogeneously a 50% acrylamide aqueous solution of 160.0 g, 35% hydrochloric acid of 2.9 g, distilled water of 316.6 g and APS of 0.50 g was added through the feed tube with the microtube pump in 120 minutes. One hour after finishing the addition, a 2.5% APS aqueous solution of 10 ml and a 2.5% SBS aqueous solution of 10 ml were added, and stirring was further continued at 80° C. for 2 hours, whereby a slightly opaque aqueous solution was obtained. The aqueous solution thus obtained had a solid concentration of 10.3%, a viscosity of 19.0 cp, and a pH of 7.35.

Examples 57 to 61

The polymerization was carried out in the same manner as in Example 56, except that the compositions were changed as shown in Table 4. The results are shown in Table 4.

TABLE 4

Polymerization Results

| Example No. | Copolymerization composition | | | | | Polymerization initiator Ammonium persulfate wt %[3] | Chain Transfer agent Sodium hypo- phosphite wt %[3] | Concen- tration wt % | pH | Viscos- ity cp | Average molecular weight MW |
|---|---|---|---|---|---|---|---|---|---|---|---|
| | AAM wt % | ASA-MA[1] Kind | wt % | Colloidizing agent Kind | mol %[2] | | | | | | |
| 48 | 90 | B-C$_{16}$ | 10 | DM hydrochloride | 230 | 0.50 | 0.25 | 10.3 | 6.70 | 20.1 | 289,000 |
| 49 | 80 | B-C$_{16}$ | 20 | DM hydrochloride | 100 | 0.50 | 0.50 | 10.4 | 7.42 | 67.4 | 265,800 |
| 50 | 70 | B-C$_{16}$ | 30 | DM hydrochloride | 60 | 0.50 | 1.00 | 10.3 | 7.71 | 892 | 196,000 |
| 51 | 90 | B-C$_{16}$ | 10 | Itaconic acid | 48 | 0.50 | 0.50 | 10.9 | 6.43 | 226 | 223,000 |
| 52 | 90 | B-C$_{16}$ | 10 | Hydrochloric acid | 48 | 0.50 | 0.50 | 10.9 | 7.13 | 28.2 | 307,000 |
| 53 | 90 | B-C$_{16}$ | — | — | — | 1.00 | 1.00 | 10.6 | 7.62 | 19.7 | 8,700 |
| 54 | 80 | B-C$_{16}$ | 20 | — | — | 1.50 | 1.50 | 10.6 | 7.68 | 14.1 | 4,900 |
| 55 | 70 | B-C$_{16}$ | 30 | — | — | 2.00 | 2.00 | 10.5 | 7.92 | 7.6 | 3,200 |
| 56 | 80 | B-C$_{18}$ | 20 | Hydrochloric acid | 53 | 0.50 | 0.75 | 10.3 | 7.35 | 19.0 | 357,000 |
| 57 | 70 | B-C$_{18}$ | 30 | Hydrochloric acid | 50 | 0.50 | 1.00 | 10.3 | 7.56 | 12.7 | 268,000 |
| 58 | 80 | B-C$_{18}$ | 20 | DM hydrochloride | 120 | 0.50 | 0.50 | 10.2 | 7.62 | 40.0 | 218,000 |
| 59 | 70 | B-C$_{18}$ | 30 | DM hydrochloride | 70 | 0.50 | 1.00 | 10.5 | 7.87 | 36.0 | 172,000 |
| 60 | 80 | B-C$_{18}$ | 20 | Itaconic acid | 50 | 0.50 | 0.50 | 10.4 | 7.55 | 66.9 | 451,000 |
| 61 | 70 | B-C$_{18}$ | 30 | Itaconic acid | 30 | 0.50 | 0.70 | 10.1 | 8.04 | 55.6 | 241,000 |

[1] Concentration as sodium salts;
[2] value based on ASA-MA;
[3] value based on solid content of total monomers Comparative Examples 2 to 7

The polymerization was carried out in the same manners and the same compositions as in Examples 48 to 52, except that distilled water was substituted for DM and 35% hydrochloric acid, and the whole solution was solidified in a gel form in the middle of the addition, which made it impossible to continue the polymerization in a homogeneous system. Accordingly, the polymerization was stopped.

Comparative Examples 8 to 12

The polymerization was carried out in the same manners and the same compositions as in Examples 56 to 61, except that distilled water was substituted for DM and 35% hydrochloric acid, and the whole solution was solidified in a gel form in the middle of the addition, which made it impossible to continue the polymerization in a homogeneous system. Accordingly, the polymerization was stopped.

Water Dispersible Resin Composition (IV)

The amphipathic compound (IV) of the present invention shall be explained in detail but the present invention shall not be restricted to these examples. In the following examples, percentage is based on weight, and viscosity is a value determined with a B type viscometer at 25° C. In emulsion aqueous solutions, viscosity is a value determined by fixing the revolution to 30 rpm since the emulsion aqueous solutions show thixotropy.

Example 62

A four neck flask of 300 ml equipped with a stirrer, a reflux condenser, a nitrogen introducing tube and a feed tube was charged with an aqueous solution prepared by blending homogeneously a 20 wt % aqueous solution of B-C$_{16}$-ESA-MA produced in Example 1 of 15.0 g, distilled water of 134.6 g, and sodium hypophosphite monohydrate of 0.075 g, and heated to 80° C. while stirring after substituted the air in the flask with nitrogen. A solution prepared by blending homogeneously a 50% acrylamide aqueous solution of 48.4 g, DM of 2.8 g, distilled water of 66.9 g and APS of 0.15 g and then adjusting the pH to 6.0 with 35% hydrochloric acid of 1.8 g was added to the above solution through the feed tube in 2 hours. Stirring was continued for one hour after finishing the addition, whereby a slightly opaque aqueous solution was obtained. Subsequently, a mixed solution of styrene of 30.0 g and benzoyl peroxide (BPO) of 0.3 g was added dropwise to this aqueous solution through the feed tube in 20 minutes, and stirring was further continued at 80° C. for 3 hours, whereby an opal emulsion solution was obtained. The emulsion aqueous solution thus obtained had a solid concentration of 20.3%, a pH of 6.22 and a viscosity of 96.0 cp.

Examples 63 to 64

The polymerization was carried out in the same manner as that in Example 62, except that the monomer compositions were changed as shown in Table 5. Provided that styrene was added dropwise in 30 minutes in Example 63 and in 40 minutes in Example 64 to obtain opal emulsions in both cases. The results thereof are summarized in Table 5.

Examples 65 to 67

The polymerization was carried out in the same manner as in Examples 62 to 64, except that the hydrophobic monomer was changed from styrene to methyl methacrylate (MMA), whereby opal emulsions were obtained.

Example 68

A four neck flask of 300 ml equipped with a stirrer, a reflux condenser, a nitrogen introducing tube and a feed tube was charged with an aqueous solution prepared by blending homogeneously a 20 wt % aqueous solution of B-C$_{16}$-ESA-MA produced in Example 1 of 50.0 g, distilled water of 469.8 g, and sodium hypophosphite monohydrate of 0.25 g, and heated to 80° C. while stirring after substituted the air in the flask with nitrogen. A solution prepared by blending homogeneously a 50% acrylamide aqueous solution of 161.2 g, DM of 9.4 g, distilled water of 303.0 g, and APS of 0.50 g and then adjusting the pH to 4.5 with 35% hydrochloric acid of 5.9 g was added to the above solution through the feed tube in 2 hours. One hour after finishing the addition, a 2.5% APS aqueous solution of 10 ml and a 2.5% SBS aqueous solution of 10 ml were added, and stirring was further continued at 80° C. for 2 hours, whereby a slightly opaque aqueous solution was obtained. This solution had a solid concentration of 10.5%, a pH of 6.86 and a viscosity of 24.5 cp. This high molecular surfactant aqueous solution is designated as PD-1.

A four neck flask of 300 ml equipped with a stirrer, a reflux condenser, a nitrogen-introducing tube and a feed tube was charged with an aqueous solution prepared by dissolving homogeneously PD-1 of 142.5 g, distilled water of 7.35 g and potassium persulfate (KPS) of 0.15 g, and heated up to 60° C. while stirring after substituted the air in the flask with nitrogen. A mixed solution of MMA of 27.0 g and 2-ethylhexyl acrylate (2EHA) of 3.0 g was added dropwise through the feed tube in 60 minutes, and stirring was further continued at 60° C. for 7 hours, whereby an opal emulsion solution was obtained. The emulsion solution had a solid concentration of 24.3%, a pH of 5.71 and a viscosity of 640 cp.

Examples 69 to 73

The polymerization was carried out in the same manner as in Example 68, except that the composition of the hydrophobic monomer was changed as shown in Table 5. The results thereof are summarized in Table 5.

Coagulations are formed during the emulsion-polymerization of the hydrophobic monomers in the presence of the polymers in which ASA-MA is not copolymerized, and therefore the emulsifiers are essential for forming the emulsions. It is supposed, however, that since emulsion particles have a weak interaction with water soluble polymers in principle, the most part of the polymers can not stay on particle surfaces even with emulsifiers. According to the present invention, emulsions having excellent stability can be prepared in the presence of the high molecular surfactant of the present invention. Further, the high molecular surfactant has an ability to form colloid particles by itself, and the copolymerized amount of hydrophobic monomers exceeding a fixed amount (about 10%) increases the particles in whole. Accordingly, it is judged that hydrophilic polymers free from the particles are scarcely present.

Water dispersible Resin Composition (II)

The water dispersible resin composition (II) of the present invention shall be explained but the present invention shall not be restricted to these examples. In the following examples, percentage is based on weight, and viscosity is a value determined with a B type viscometer at 25° C.

TABLE 5

Emulsion Polymerization, Result

| Example No. | A:B[1] (composition Ratio) | Hydrophobic monomer[2] | | | Polymerization initiator[3] | | Emulsion polymerization result | | | |
|---|---|---|---|---|---|---|---|---|---|---|
| | | Styrene wt % | MMA wt % | 2 EHA wt % | BPO wt % | KPS wt % | Concentration wt % | pH | Viscosity cp | Particle diameter[4] nm |
| 62 | 50:50 | 100 | — | — | 1 | — | 20.3 | 6.22 | 96.0 | 208 |
| 63 | 40:60 | 100 | — | — | 1 | — | 24.7 | 5.84 | 161 | 341 |
| 64 | 33:67 | 100 | — | — | 1 | — | 28.9 | 5.55 | 320 | 457 |
| 65 | 50:50 | — | 100 | — | 1 | — | 19.6 | 6.25 | 68.0 | 216 |
| 66 | 40:60 | — | 100 | — | 1 | — | 23.5 | 5.88 | 220 | 274 |
| 67 | 33:67 | — | 100 | — | 1 | — | 28.5 | 6.17 | 256 | 330 |
| 68 | 33:67 | — | 90 | 10 | — | 1 | 24.3 | 5.71 | 640 | 249 |
| 69 | 33:67 | — | 80 | 20 | — | 1 | 25.6 | 5.65 | 519 | 266 |
| 70 | 33:67 | — | 70 | 30 | — | 1 | 25.1 | 5.76 | 295 | 241 |
| 71 | 33:67 | 90 | — | 10 | — | 1 | 25.0 | 5.64 | 351 | 450 |
| 72 | 33:67 | 80 | — | 20 | — | 1 | 25.1 | 5.63 | 334 | 437 |
| 73 | 33:67 | 70 | — | 30 | — | 1 | 24.7 | 5.70 | 270 | 546 |
| PD-1 | — | — | — | — | — | — | 10.5 | 6.86 | 24.5 | 214 |

[1]High molecular surfactant (A): hydrophobic monomer (B) in terms of a solid weight ratio.
[2]Composition ratio of the hydrophobic monomers.
[3]Addition amount (wt %) based on the total amounts of the hydrophobic monomers.
[4]Value in the aqueous solution of pH 5.5.

Comparative Examples 13 to 18

The polymerization was carried out in the same manners as in Examples 62 to 67 without using B-$C_{16}$-ESA-MA. The solutions were coagulated during the polymerization of the hydrophobic monomers, and therefore emulsions could not be obtained.

Particle Diameter Measuring Examples 1 to 6

The particle diameters of the emulsions obtained in Examples 62 to 67 were determined in the aqueous solutions with a Coal Tar N4 type submicron particle analyzer manufactured by Coal Tar Co., Ltd. in scattered light of 90°. The results thereof are summarized in Table 5. Further, the particle diameter of the high molecular surfactant alone before adding the hydrophobic monomer was shown together.

Example 74

Styrene of 100.0 g was added dropwise to an aqueous solution prepared by dissolving homogeneously a 80 wt % aqueous solution of B-$C_{18}$-ESA-MA produced in Example 3 of 6.53 g in distilled water of 53.5 g in 30 minutes while stirring vigorously with a magnetic stirrer to prepare an opal monomer emulsion. A four neck flask of 300 ml equipped with a stirrer, a reflux condenser, a nitrogen introducing tube and a dropping funnel was charged with distilled water of 98.3 g, and heated to 80° C. after substituting the air in the flask with nitrogen, followed by adding a 10% potassium persulfate aqueous solution of 5.0 g. Then, a monomer emulsion prepared in advance was continuously added dropwise from the dropping funnel in 2 hours. After finishing the addition, ripening was carried out for 2 hours to obtain an opal stable emulsion free of coagulations. This emulsion had a pH of 8.20, a solid concentration of 40.5% and a viscosity of 8.5 cp. The results thereof are summarized in Table 6.

Examples 75 to 77

The polymerization was carried out in the same manner as in Example 74, except that the monomer compositions were changed as shown in Table 6, and opal, good emulsions were obtained in all examples. The results are summarized in Table 6.

Example 78

Styrene of 100.0 g was added dropwise to an aqueous solution prepared by dissolving homogeneously a 80 wt % aqueous solution of B-$C_{18}$-ESA-MA produced in Example 3 of 6.55 g in distilled water of 53.5 g in 30 minutes while stirring vigorously with a magnetic stirrer to prepare an opal monomer emulsion. A four neck flask of 300 ml equipped with a stirrer, a reflux condenser, a nitrogen introducing tube and a dropping funnel was charged with distilled water of 98.3 g, and heated to 80° C. after substituting the air in the flask with nitrogen, followed by adding a 10% potassium persulfate aqueous solution of 5.0 g. Then, a monomer emulsion prepared in advance was continuously added dropwise from the dropping funnel in 2 hours. After finishing the addition, ripening was carried out for 2 hours to obtain an opal stable emulsion free of coagulations. This emulsion had a pH of 8.35, a solid concentration of 41.3% and a viscosity of 10.6 cp. The results thereof are summarized in Table 6.

Comparative Example 19

The polymerization was carried out in the same manner as in Example 74, except that sodium alkylbenzenesulfonate was substituted for ESA-MA, and the same amount of distilled water was substituted for 40% sodium hydroxide, whereby an opal emulsion was obtained. The results are summarized in Table 6.

[Evaluation of Films]

The emulsion solutions obtained in Examples 74 to 78 and Comparative Example 19 were dried at room temperatures by a cast method to prepare films of 0.25 mm. After the dried films were immersed in a 1.0% hydrochloric acid aqueous solution for 30 minutes, water droplets remaining on film surfaces were wiped off with filter papers, and then the films were subjected to heat treatment in a constant temperature drier of 100° C. for one hour. A waterproof test was carried out by a method in which the films were immersed in distilled water at room temperatures to determine a water absorption amount. A water absorption rate (%) was represented by a weight percentage (%) of the water absorption amount per polymer film. The same test was carried out as well in Comparative Example 19, and the results are shown in Table 7.

TABLE 6

Emulsion Polymerization Results

| Example No. | Emulsifier | Monomer composition St (wt%) | Monomer composition MMA (wt%) | pH | Polymerization result Solid content (wt%) | Polymerization result Viscosity (cp) |
|---|---|---|---|---|---|---|
| 74 (Inv.) | B—$C_{18}$-ESA-MA | 100 | — | 8.20 | 40.5 | 8.5 |
| 75 (Inv.) | B—$C_{18}$-ESA-MA | 70 | 30 | 8.25 | 40.3 | 11.3 |
| 76 (Inv.) | B—$C_{18}$-ESA-MA | 60 | 40 | 8.22 | 40.5 | 7.3 |
| 77 (Inv.) | B—$C_{18}$-ESA-MA | 50 | 50 | 8.35 | 40.6 | 7.0 |
| 78 (Inv.) | B—$C_{18}$-ESA-MA | 100 | — | 8.15 | 40.2 | 5.1 |
| 19 (Comp.) | ABS | 100 | — | 7.02 | 40.6 | 10.5 |

St: styrene,
MMA: methyl methacrylate,
ABS: sodium alkylbenzenesulfonate

TABLE 7

Waterproof Test Results

| Example No. | Water absorption rate (%) Immersing time 1 hour | 2 hours | 4 hours | 8 hours |
|---|---|---|---|---|
| 74 (Inv.) | 0 | 0 | 1 | 1 |
| 75 (Inv.) | 0 | 1 | 1 | 2 |
| 76 (Inv.) | 1 | 1 | 2 | 3 |
| 77 (Inv.) | 1 | 1 | 2 | 4 |
| 78 (Inv.) | 1 | 1 | 2 | 4 |
| 19 (Comp.) | 5 | 8 | 10 | 25 |

Heat resistance was evaluated by determining a Tg (glass transition temperature) by a transition temperature measuring method with DSC (DSC-50: manufactured by Shimadzu Mfg. Co., Ltd.) according to JIS K-7121-1987. A standard sample (standard pellet manufactured by Scientific Polymer Products, INC.) of polystyrene had a Tg of 104° C.; a film produced from the emulsion obtained in Example 74, which was not subjected to acid treatment, had a Tg of 102° C., and the film sample which was subjected to heat treatment after the acid treatment had a Tg of 106° C.; and the film prepared in Comparative Example 19 had a Tg of 100° C.

The water dispersible resin composition of the present invention is a stable emulsion, and as apparent from the examples, a polymer film obtained from the emulsion is excellent in water resistance and heat resistance as compared with films produced by using conventional surfactants as emulsifiers. The actions thereof are not necessarily clarified, but the excellent water resistance and heat resistance described above are considered to originate in the fact that since the succinic acid allylamide type reactive surfactant is highly copolymerizable, free monomers are scarcely found after the polymerization. Further, it is considered that in the polymer films having a succinic acid monoallylamide structure, succinamide brings about cyclodehydration by subjecting the polymer films to acid and heat treatment to form an imide structure and therefore the various performances are further improved.

What is claimed is:

1. A high molecular compound obtained by copolymerizing 0.1 to 90.0 weight % of an amphipathic compound having a succinic acid skeleton represented by any of the following Formulas (18) to (19) or a mixture thereof with 10.0 to 99.9 weight % of a copolymerizable ethylenically unsaturated compound:

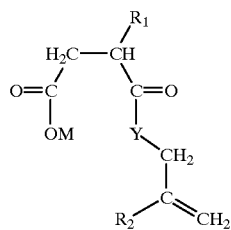
(18)

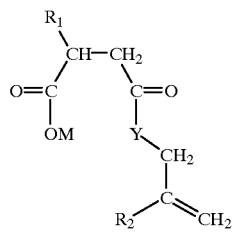
(19)

wherein $R_1$ is a linear or branched, saturated hydrocarbon group having 6 to 48 carbon atoms, or a linear or branched, unsaturated hydrocarbon group containing 1 to 12 unsaturated double bond and having 6 to 48 carbon atoms; $R_2$ is a hydrogen atom or a methyl group; M is hydrogen atom, alkali metal, or an ammonium group; and Y is NH or N—($CH_2$—CH=$CH_2$).

2. A water soluble or dispersible amphipathic high molecular compound obtained by copolymerizing 0.1 to 90.0 weight % of the compound represented by any of the following Formulas (18) to (21) or a mixture thereof with 10.0 to 99.9 weight % of a hydrophilic ethylenically unsaturated compound:

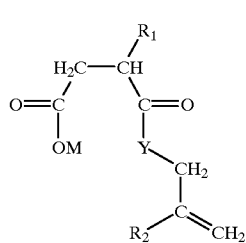
(18)

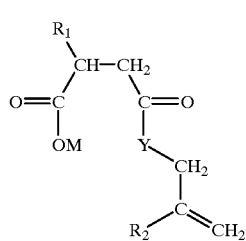
(19)

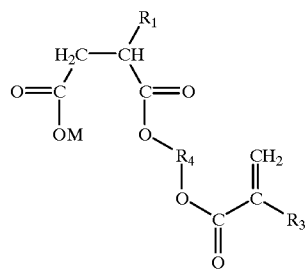
(20)

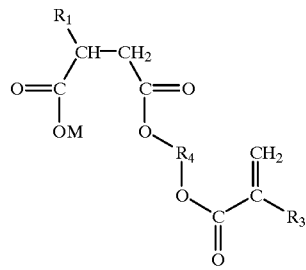
(21)

wherein $R_1$ is a linear or branched, saturated hydrocarbon group having 6 to 48 carbon atoms, or a linear or branched, unsaturated hydrocarbon group containing 1 to 12 unsaturated doble bonds and having 6 to 48 carbon atoms; $R_2$ and $R_3$ are independently a hydrogen atom or a methyl group; $R_4$ is a linear or branched, saturated hydrocarbon group having 2 to 6 carbon atoms; M is a hydrogen atom, alkali metal, or an ammonium group; and Y is NH, N—($CH_2$—CH=$CH_2$), or O.

3. A paper making additive containing the water soluble or dispersible amphipathic high molecular compound as described in claim 2 as an active ingredient.

4. A process for producing an amphipathic high molecular compound comprising copolymerizing a reactive surfactant with a hydrophilic, nonionic unsaturated compound in an aqueous medium in the presence of a colloidizing agent wherein the reactive surfactant is represented by any of Formulas (18) to (19):

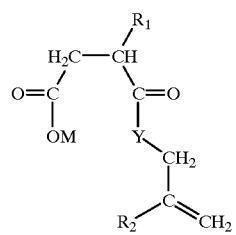
(18)

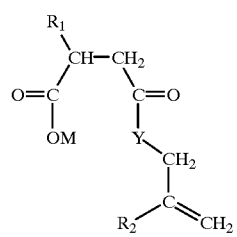
(19)

wherein $R_1$ is a linear or branched, saturated hydrocarbon group having 6 to 48 carbon atoms, or a linear or branched, unsaturated hydrocarbon group containing 1 to 12 unsaturated double bonds and having 6 to 48 carbon atoms; $R_2$ is a hydrogen atom or a methyl group; M is a hydrogen atom, alkali metal, or an ammonium group; and Y is NH or N—($CH_2$—CH=$CH_2$).

5. A process for producing an amphipathic high molecular compound as described in claim 4, wherein 0.1 to 90 weight % of the reactive surfactant is copolymerized with 10 to 99.9 weight % of the hydrophilic, nonionic ethylenically unsaturated compound in the aqueous medium in the presence of the colloidizing agent in an amount of 0.1 to 10 moles per mole of the reactive surfactant.

6. A process for producing an amphipathic high molecular compound as described in claim 5, wherein the colloidizing agent comprises at least one or a combination selected from an inorganic acid, an organic acid, an inorganic base, and an organic base.

7. A process for producing an amphipathic high molecular compound as described in claim 4, wherein the colloidizing agent comprises at least one or a combination selected from an inorganic acid, an organic acid, an inorganic base, and an organic base.

8. A process for producing an amphipathic high molecular compound as described in claim 4, wherein the reactive surfactant has at least one carboxyl group in the molecule.

9. A process for producing an amphipathic high molecular compound as described in claim 8, wherein 10 to 99.9 weight % of the hydrophilic, nonionic ethylenically unsaturated compound is copolymerized with 0.1 to 90 weight % of the reactive surfactant having at least one carboxyl group in the molecule in an aqueous medium in the presence of the colloidizing agent in an amount of 0.1 to 10 moles per mole of the reactive surfactant.

10. A process for producing an amphipathic high molecular compound as described in claim 9, wherein the colloidizing agent comprises at least one or a combination selected from an inorganic acid, an organic acid, an inorganic base, and an organic base.

* * * * *